(12) United States Patent
Deutsch et al.

(10) Patent No.: US 9,200,245 B2
(45) Date of Patent: Dec. 1, 2015

(54) MULTIWELL PLATE

(75) Inventors: Mordechai Deutsch, Moshav Olesh (IL); Max Herzberg, Moshav Sitria (IL); Reuven Tirosh, Kfar-Saba (IL); Assaf Deutsch, Tzfaria (IL)

(73) Assignee: Seng Enterprises Ltd., Larnaca (CY)

( * ) Notice: Subject to any disclaimer, the term of this patent is extended or adjusted under 35 U.S.C. 154(b) by 1661 days.

(21) Appl. No.: 10/565,240

(22) PCT Filed: Jul. 20, 2004

(86) PCT No.: PCT/IL2004/000661
§ 371 (c)(1),
(2), (4) Date: May 3, 2007

(87) PCT Pub. No.: WO2005/007796
PCT Pub. Date: Jan. 27, 2005

(65) Prior Publication Data
US 2007/0292837 A1    Dec. 20, 2007

Related U.S. Application Data

(63) Continuation-in-part of application No. PCT/IL2004/000571, filed on Jun. 27, 2004, which is a continuation-in-part of application No. 10/561,839, filed as application No. PCT/IL2004/000571 on Jun. 27, 2004, now abandoned.

(Continued)

(51) Int. Cl.
*C12M 3/00* (2006.01)
*C12M 1/32* (2006.01)
(Continued)

(52) U.S. Cl.
CPC .............. *C12M 23/12* (2013.01); *B01L 3/5085* (2013.01); *C12N 11/04* (2013.01);
(Continued)

(58) Field of Classification Search
CPC ..... C12M 23/12; C12M 23/20; B01L 3/5085; B01L 2200/0668; B01L 2300/0829; B01L 3/0893; B01L 3/0896; B01L 2200/12; C12N 11/04
USPC ................................ 435/288.4, 305.2, 305.3
See application file for complete search history.

(56) References Cited

U.S. PATENT DOCUMENTS

| | | |
|---|---|---|
| 655,365 A | 8/1900 | Johnson |
| 3,558,387 A | 1/1971 | Bassemir et al. |

(Continued)

FOREIGN PATENT DOCUMENTS

| | | |
|---|---|---|
| DE | 4132379 | 4/1993 |
| EP | 0059297 | 9/1982 |

(Continued)

OTHER PUBLICATIONS

Invitation Pursuant to Article 94(3) and Rule 71(1) EPC Dated Jun. 25, 2013 From the European Patent Office Re. Application No. 04744911.1.

(Continued)

*Primary Examiner* — William H Beisner

(57) ABSTRACT

A mulitwell plate having a plurality of picowells on the bottom of the wells of the plate as well as methods of producing the mulitwell plate are provided. Provided is also a method of handling living cells by providing an ordered array of living cells immobilized in a non-fluid matrix, contacting the living cells with a stimulus; and detecting a response to the stimulus. The present invention is also of a method of producing an ordered array of living cells.

58 Claims, 20 Drawing Sheets

Related U.S. Application Data

(60) Provisional application No. 60/488,408, filed on Jul. 21, 2003, provisional application No. 60/488,409, filed on Jul. 21, 2003, provisional application No. 60/517,073, filed on Nov. 5, 2003, provisional application No. 60/517,084, filed on Nov. 5, 2003, provisional application No. 60/544,356, filed on Feb. 17, 2004, provisional application No. 60/544,357, filed on Feb. 17, 2004, provisional application No. 60/482,437, filed on Jun. 26, 2003.

(51) Int. Cl.
*B01L 3/00* (2006.01)
*C12N 11/04* (2006.01)
*G01N 33/50* (2006.01)
*C12M 1/00* (2006.01)

(52) U.S. Cl.
CPC .... *G01N 33/5008* (2013.01); *B01L 2200/0668* (2013.01); *B01L 2200/12* (2013.01); *B01L 2300/04* (2013.01); *B01L 2300/069* (2013.01); *B01L 2300/0819* (2013.01); *B01L 2300/0829* (2013.01); *B01L 2300/0893* (2013.01); *B01L 2300/0896* (2013.01); *B01L 2400/0409* (2013.01); *B01L 2400/0454* (2013.01); *B01L 2400/0457* (2013.01); *B01L 2400/0487* (2013.01); *C12M 23/20* (2013.01); *Y10T 29/49* (2015.01)

(56) References Cited

U.S. PATENT DOCUMENTS

| | | | |
|---|---|---|---|
| 4,072,578 A | 2/1978 | Cady et al. | |
| 4,207,554 A | 6/1980 | Resnick et al. | |
| 4,308,351 A * | 12/1981 | Leighton et al. | 435/297.5 |
| 4,684,538 A | 8/1987 | Klemarczyk | |
| 4,716,101 A * | 12/1987 | Thompson et al. | 435/4 |
| 4,729,949 A | 3/1988 | Weinreb et al. | |
| 4,756,884 A | 7/1988 | Hillman et al. | |
| 4,839,280 A | 6/1989 | Banes | |
| 4,894,343 A | 1/1990 | Tanaka et al. | |
| 4,895,805 A | 1/1990 | Sato et al. | |
| 5,043,082 A | 8/1991 | Hermann, Jr. et al. | |
| 5,059,266 A | 10/1991 | Yamane et al. | |
| 5,153,136 A | 10/1992 | Vandenburgh | |
| 5,204,055 A | 4/1993 | Sachs et al. | |
| 5,272,081 A | 12/1993 | Weinreb et al. | |
| 5,324,591 A | 6/1994 | Georger et al. | |
| 5,395,588 A | 3/1995 | North, Jr. et al. | |
| 5,428,451 A | 6/1995 | Lea et al. | |
| 5,506,141 A | 4/1996 | Weinreb et al. | |
| 5,525,800 A | 6/1996 | Sanghera et al. | |
| 5,612,184 A | 3/1997 | Rosson | |
| 5,627,045 A | 5/1997 | Bochner et al. | |
| 5,650,323 A | 7/1997 | Root et al. | |
| 5,707,869 A | 1/1998 | Wolf et al. | |
| 5,744,366 A | 4/1998 | Kricka et al. | |
| 5,854,684 A | 12/1998 | Stabile et al. | |
| 5,905,031 A | 5/1999 | Kuylen et al. | |
| 5,910,287 A | 6/1999 | Cassin et al. | |
| 6,025,129 A | 2/2000 | Nova et al. | |
| 6,027,695 A | 2/2000 | Oldenburg et al. | |
| 6,037,168 A | 3/2000 | Brown | |
| 6,046,426 A | 4/2000 | Jeantette et al. | |
| 6,048,723 A | 4/2000 | Banes | |
| 6,066,285 A | 5/2000 | Kumar | |
| 6,103,479 A | 8/2000 | Taylor | |
| 6,117,612 A | 9/2000 | Halloran et al. | |
| 6,206,672 B1 | 3/2001 | Grenda | |
| 6,228,437 B1 | 5/2001 | Schmidt | |
| 6,238,614 B1 | 5/2001 | Yang et al. | |
| 6,315,940 B1 | 11/2001 | Nisch et al. | |
| 6,329,195 B1 | 12/2001 | Pfaller | |
| 6,333,192 B1 | 12/2001 | Petitte et al. | |
| 6,338,964 B1 | 1/2002 | Matanguihan et al. | |
| 6,342,384 B1 | 1/2002 | Chung et al. | |
| 6,344,354 B1 | 2/2002 | Webster et al. | |
| 6,345,115 B1 | 2/2002 | Ramm et al. | |
| 6,372,494 B1 | 4/2002 | Naughton et al. | |
| 6,376,148 B1 | 4/2002 | Liu et al. | |
| 6,377,721 B1 | 4/2002 | Walt et al. | |
| 6,378,527 B1 | 4/2002 | Hungerford et al. | |
| 6,383,810 B2 | 5/2002 | Fike et al. | |
| 6,403,369 B1 | 6/2002 | Wood | |
| 6,410,309 B1 | 6/2002 | Barbera-Guillem et al. | |
| 6,413,680 B1 | 7/2002 | Watanabe et al. | |
| 6,413,744 B1 | 7/2002 | Morris et al. | |
| 6,413,746 B1 | 7/2002 | Field | |
| 6,416,642 B1 | 7/2002 | Alajoki et al. | |
| 6,455,310 B1 | 9/2002 | Barbera-Guillem et al. | |
| 6,465,000 B1 | 10/2002 | Kim | |
| 6,465,205 B2 | 10/2002 | Hicks, Jr. | |
| 6,468,788 B1 | 10/2002 | Marotzki | |
| 6,479,252 B1 | 11/2002 | Barbera-Guillem et al. | |
| 6,485,690 B1 | 11/2002 | Pfost et al. | |
| 6,489,144 B1 | 12/2002 | Lau | |
| 6,492,148 B1 | 12/2002 | van Loon et al. | |
| 6,492,163 B1 | 12/2002 | Yoo et al. | |
| 6,495,340 B2 | 12/2002 | Huberman et al. | |
| 6,506,598 B1 | 1/2003 | Andersen et al. | |
| 6,511,430 B1 | 1/2003 | Sherar et al. | |
| 6,521,182 B1 | 2/2003 | Shartle et al. | |
| 6,528,286 B1 | 3/2003 | Ryll | |
| 6,544,788 B2 | 4/2003 | Singh | |
| 6,555,365 B2 | 4/2003 | Barbera-Guillem et al. | |
| 6,569,422 B1 | 5/2003 | van Loon et al. | |
| 6,588,586 B2 | 7/2003 | Abasolo et al. | |
| 6,589,765 B1 | 7/2003 | Choi et al. | |
| 6,593,101 B2 | 7/2003 | Richards-Kortum et al. | |
| 6,593,140 B1 | 7/2003 | Field | |
| 6,610,516 B1 | 8/2003 | Andersen et al. | |
| 6,627,426 B2 | 9/2003 | Biddle et al. | |
| 6,632,619 B1 | 10/2003 | Harrison et al. | |
| 6,635,448 B2 | 10/2003 | Bucciarelli et al. | |
| 6,642,050 B1 | 11/2003 | Goto et al. | |
| 6,645,757 B1 | 11/2003 | Okandan et al. | |
| 6,649,408 B2 | 11/2003 | Bailey et al. | |
| 6,653,124 B1 | 11/2003 | Freeman | |
| 6,660,501 B2 | 12/2003 | Field | |
| 6,667,034 B2 | 12/2003 | Palsson et al. | |
| 6,670,180 B2 | 12/2003 | Block | |
| 6,670,184 B2 | 12/2003 | Chiarello et al. | |
| 6,673,591 B2 | 1/2004 | Lau | |
| 6,686,190 B2 | 2/2004 | Lau | |
| 6,689,594 B1 | 2/2004 | Hänni et al. | |
| 6,692,961 B1 | 2/2004 | Judd et al. | |
| 6,695,765 B1 | 2/2004 | Beebe et al. | |
| 6,699,665 B1 * | 3/2004 | Kim et al. | 506/13 |
| 6,706,519 B1 * | 3/2004 | Kellogg et al. | 435/287.2 |
| 7,118,910 B2 | 10/2006 | Unger et al. | |
| 7,139,415 B2 | 11/2006 | Finkbeiner | |
| 7,169,578 B2 | 1/2007 | Wang et al. | |
| 7,285,412 B2 | 10/2007 | Casagrande et al. | |
| 7,323,305 B2 | 1/2008 | Leamon et al. | |
| 7,354,733 B2 | 4/2008 | Bukshpan et al. | |
| 7,403,647 B2 | 7/2008 | Deutsch et al. | |
| 7,405,071 B2 | 7/2008 | Deutsch | |
| 7,888,110 B2 | 2/2011 | Deutsch et al. | |
| 8,003,377 B2 | 8/2011 | Deutsch et al. | |
| 2002/0001856 A1 | 1/2002 | Chow et al. | |
| 2002/0052003 A1 | 5/2002 | Alberte et al. | |
| 2002/0064885 A1 | 5/2002 | Bedingham et al. | |
| 2002/0106715 A1 | 8/2002 | Huberman et al. | |
| 2002/0127604 A1 | 9/2002 | Allbritton et al. | |
| 2002/0150909 A1 | 10/2002 | Stuelpnagel et al. | |
| 2002/0173033 A1 | 11/2002 | Hammerick et al. | |
| 2002/0182627 A1 | 12/2002 | Wang et al. | |
| 2002/0187074 A1 | 12/2002 | O'Connor et al. | |
| 2002/0189374 A1 | 12/2002 | DeSilets et al. | |
| 2003/0017079 A1 | 1/2003 | Hahn et al. | |

(56) References Cited

U.S. PATENT DOCUMENTS

| | | |
|---|---|---|
| 2003/0030184 A1 | 2/2003 | Kim et al. |
| 2003/0032048 A1 | 2/2003 | Kim et al. |
| 2003/0032204 A1 | 2/2003 | Walt et al. |
| 2003/0036188 A1* | 2/2003 | Kim et al. ................... 435/288.4 |
| 2003/0059764 A1 | 3/2003 | Ravkin et al. |
| 2003/0082632 A1 | 5/2003 | Shumate |
| 2003/0082818 A1 | 5/2003 | Bahnson et al. |
| 2003/0087292 A1 | 5/2003 | Chen et al. |
| 2003/0104494 A1 | 6/2003 | Ravkin et al. |
| 2003/0113833 A1 | 6/2003 | Oka et al. |
| 2003/0124716 A1 | 7/2003 | Hess et al. |
| 2003/0162284 A1 | 8/2003 | Dordick et al. |
| 2003/0189850 A1 | 10/2003 | Sasaki et al. |
| 2003/0211458 A1 | 11/2003 | Sunray et al. |
| 2004/0053354 A1 | 3/2004 | Ikawa et al. |
| 2004/0091397 A1 | 5/2004 | Picard |
| 2004/0118757 A1 | 6/2004 | Terstappen et al. |
| 2004/0216835 A1 | 11/2004 | Tanner et al. |
| 2004/0235143 A1 | 11/2004 | Sasaki et al. |
| 2004/0241783 A1 | 12/2004 | Papkovsky et al. |
| 2004/0262210 A1 | 12/2004 | Westervelt et al. |
| 2005/0014201 A1 | 1/2005 | Deuthsch |
| 2005/0026299 A1 | 2/2005 | Bhattacharjee et al. |
| 2005/0064524 A1 | 3/2005 | Deutsch et al. |
| 2005/0074869 A1 | 4/2005 | Yoshida et al. |
| 2005/0089993 A1 | 4/2005 | Boccazzi et al. |
| 2005/0105077 A1 | 5/2005 | Padmanabhan et al. |
| 2005/0106714 A1 | 5/2005 | Zarur et al. |
| 2005/0158845 A1 | 7/2005 | Wikswo et al. |
| 2005/0170498 A1 | 8/2005 | Dolley et al. |
| 2005/0230272 A1 | 10/2005 | Lee et al. |
| 2005/0277125 A1 | 12/2005 | Benn et al. |
| 2006/0041384 A1 | 2/2006 | Kermani et al. |
| 2006/0057557 A1 | 3/2006 | Deutsch et al. |
| 2006/0154233 A1 | 7/2006 | Deutsch |
| 2006/0240548 A1 | 10/2006 | Deutsch et al. |
| 2007/0105089 A1 | 5/2007 | Deutsch |
| 2007/0141555 A1 | 6/2007 | Deutsch |
| 2007/0154357 A1 | 7/2007 | Szlosek |
| 2007/0178607 A1 | 8/2007 | Prober et al. |
| 2007/0292312 A1 | 12/2007 | Bachman et al. |
| 2007/0292837 A1 | 12/2007 | Deutsch et al. |
| 2008/0003142 A1 | 1/2008 | Link et al. |
| 2008/0009051 A1 | 1/2008 | Deutsch et al. |
| 2008/0063251 A1 | 3/2008 | Deutsch |
| 2008/0063572 A1 | 3/2008 | Deutsch et al. |
| 2008/0241874 A1 | 10/2008 | Deutsch |
| 2009/0105095 A1 | 4/2009 | Deutsch |
| 2009/0111141 A1 | 4/2009 | Deutsch |
| 2011/0014688 A1 | 1/2011 | Deutsch et al. |
| 2013/0071914 A1 | 3/2013 | Deutsch |

FOREIGN PATENT DOCUMENTS

| | | |
|---|---|---|
| EP | 0094193 | 11/1983 |
| EP | 0602416 | 6/1994 |
| EP | 1262764 | 12/2002 |
| EP | 1566635 | 8/2005 |
| EP | 1691196 | 8/2006 |
| FR | 2890975 | 3/2007 |
| JP | 62-171687 | 7/1987 |
| JP | 06-221988 | 8/1994 |
| JP | 06-237753 | 8/1994 |
| JP | 10-276763 | 10/1998 |
| JP | 11-507724 | 7/1999 |
| JP | 2005-102628 | 4/2005 |
| WO | WO 96/31548 | 10/1996 |
| WO | WO 96/41153 | 12/1996 |
| WO | WO 98/15356 | 4/1998 |
| WO | WO 98/35223 | 8/1998 |
| WO | WO 99/45357 | 9/1999 |
| WO | WO 99/47922 | 9/1999 |
| WO | WO 99/66329 | 12/1999 |
| WO | WO 00/20554 | 4/2000 |
| WO | WO 0102539 A1 * | 1/2001 |
| WO | WO 01/35071 | 5/2001 |
| WO | WO 01/49824 | 7/2001 |
| WO | WO 01/88176 | 11/2001 |
| WO | WO 01/88185 | 11/2001 |
| WO | WO 02/08748 | 1/2002 |
| WO | WO 02/26114 | 4/2002 |
| WO | WO 02/48676 | 6/2002 |
| WO | WO 02/055653 | 7/2002 |
| WO | WO 02/058847 | 8/2002 |
| WO | WO 02/063034 | 8/2002 |
| WO | WO 02/064728 | 8/2002 |
| WO | WO 02/081662 | 10/2002 |
| WO | WO 02/097398 | 12/2002 |
| WO | WO 03/002750 | 1/2003 |
| WO | WO 03/035824 | 1/2003 |
| WO | WO 03/011451 | 2/2003 |
| WO | WO 03/020871 | 3/2003 |
| WO | WO 03/046508 | 6/2003 |
| WO | WO 03/052375 | 6/2003 |
| WO | WO 03/056330 | 7/2003 |
| WO | WO 03/056345 | 7/2003 |
| WO | WO 2004/077009 | 9/2004 |
| WO | WO 2004/113492 | 12/2004 |
| WO | WO 2005/007796 | 1/2005 |
| WO | WO 2005/069001 | 7/2005 |
| WO | WO 2005/103691 | 11/2005 |
| WO | WO 2006/003664 | 1/2006 |
| WO | WO 2006/021959 | 3/2006 |
| WO | WO 2006/043267 | 4/2006 |
| WO | WO 2006/080000 | 8/2006 |
| WO | WO 2007/052245 | 5/2007 |
| WO | WO 2007/074449 | 7/2007 |
| WO | WO 2009/063462 | 5/2009 |
| WO | WO 2009/081409 | 7/2009 |

OTHER PUBLICATIONS

Official Action Dated Jun. 20, 2013 From the US Patent and Trademark Office Re. U.S. Appl. No. 12/155,643.
Gelest "Optical Materials", 'Gelest', Enabling Your Technology, Downloaded from Internet, 36 P., 2007.
Applicant-Initiated Interview Summary Dated Aug. 16, 2013 From the US Patent and Trademark Office Re. U.S. Appl. No. 12/810,868.
Official Action Dated Sep. 27, 2013 From the US Patent and Trademark Office Re. U.S. Appl. No. 13/651,522.
Official Action Dated Sep. 30, 2013 From the US Patent and Trademark Office Re. U.S. Appl. No. 10/561,839.
Notice of Allowance Dated Jul. 22, 2013 From the US Patent and Trademark Office Re. U.S. Appl. No. 12/742,730.
Official Action Dated Jul. 15, 2013 From the US Patent and Trademark Office Re. U.S. Appl. No. 12/810,868.
Official Action Dated Jul. 29, 2013 From the US Patent and Trademark Office Re. U.S. Appl. No. 12/712,232.
Official Action Dated Nov. 18, 2014 From the US Patent and Trademark Office Re. U.S. Appl. No. 12/810,868.
International Search Report Dated Sep. 10, 2009 From the International Searching Authority Re.: Application No. PCT/IL2008/001678.
International Search Report Dated Nov. 15, 2005 From the International Searching Authority Re.: PCT/IL2005/000719.
Official Action Dated Mar. 23, 2005 From the US Patent and Trademark Office Re.: U.S. Appl. No. 10/276,080.
Response Dated Dec. 14, 2009 to Office Action of Jul. 14, 2009 From the Israel Patent Office Re.: Application No. 172724.
Supplementary European Search Report Dated Oct. 22, 2009 From the European Patent Office Re.: Application No. 04744911.1.
Supplementary European Search Report Dated Oct. 22, 2009 From the European Patent Office Re.: Application No. 04745001.0.
Written Opinion Dated Sep. 10, 2009 From the International Searching Authority Re.: Application No. PCT/IL2008/001678.
Communication Pursuant to Article 94(3) EPC Dated Aug. 5, 2010 From the European Patent Office Re. Application No. 05757567.2.
Notice of Allowance Dated Jun. 15, 2010 From the US Patent and Trademark Office Re. U.S. Appl. No. 11/940,996.

(56) References Cited

OTHER PUBLICATIONS

Translation of Notice of Reason for Rejection Dated Jul. 23, 2010 From the Japanese Patent Office Re.: Application No. 2006-502647.
Dolbeare "Fluorescent Staining of Enzymes for Flow Cytometry", Methods Cell Biol., 33(Chap.8): 81-88, 1990.
Klingel et al. "Flow Cytometric Determination of Serine Proteinase Activities in Living Cells With Rhodamine 110 Substrates", Methods Cell Biol., 41(Chap.29): 449-460, 1994.
Malin-Berdel et al. "Flow Cytometric Determination of Esterase and Phosphatase Activities and Kinetics in Hematopoietic Cells With Fluorogenic Substrates", Cytometry, 1(3): 222-228, 1980.
Nooter et al. "On-Line Flow Cytometry. A Versatile Method for Kinetic Measurement", Methods Cell Biol., 41(Chap.32): 509-526, 1994.
Turek et al. "Leucine Aminopeptidase Activity by Flow Cytometry", Methods Cell Biol., 41(Chap.30): 461-468, 1994.
Watson et al. "Enzyme Kinetics", Methods Cell Biol., 41: 469-508, 1994.
Bedner et al. "Enzyme Kinetic Reactions and Fluorochrome Uptake Rates Measured in Individual Cells by Laser Scanning Cytometry", Cytometry, 33(1): 1-9, 1998. Abstract, p. 2, col. 1, §4-col. 2, §1, p. 8, col. 2, §2.
Sunray et al. "Cell Activation Influences Cell Staining Kinetics", Spectrochimica Part A, 53: 1645-1653, 1997.
Eisenthal et al. "Infection of K562 Cells With Influenza A Virus Increases Their Susceptibility to Natural Killer Lysis", Pathobiology, 65: 331-340, 1997.
Deutsch et al. "Apparatus for High-Precision Repetitive Sequential Optical Measurement of Living Cells", Cytometry, 16: 214-226, 1994.
Sunray et al. "Determination of the Michaelis-Menten Constant (Km) of Intracellular Enzymatic Reaction for Individual Live Lymphocytes", Cytometry Supplement, 10: 68-69, & The XX Congress of the International Society for Analytical Cytology, Montpellier, F, 2000.
Darzynkiewicz et al. "Laser-Scanning Cytometry: A New Instrumentation With Many Applications", Experimental Cell Research, 249(1): 1-12, 1999. Abstract, p. 2, col. 2, §4-p. 4, col. 2, §2, p. 8, col. 1, §1-col. 2, §2.
Sunray et al. "The Trace and Subgrouping of Lymphocyte Activation by Dynamic Fluorescence Intensity and Polarization Measurements", Biochemical and Biophysical Research Communications, 261(3): 712-719, 1999. Abstract, p. 713, col. 1, §5, col. 2, §7-p. 714, col. 2, §1.
Sunray et al. "Determination of Individual Cell Michaelis-Menten Constants", Cytometry, 47(1): 8-16, 2002.
Dive et al. Cytometry Journal of Society for Analytical Cytology, 8(6): 552-561, 1987. Abstract.
Koh et al. "Poly(Ethylene Glycol) Hydrogel Microstructures Encapsulating Living Cells", Langmuir, 18(7): 2459-2462, 2002.
Lansing Taylor et al. "Real-Time Molecular and Cellular Analysis: The New Frontier of Drug Discovery", Current Opinion in Biotechnology, 12: 75-81, 2001.
Aplin et al. "Protein-Derivatised Glass Coverslips for the Study of Cell-to- Substratum Adhesion", Analytical Biochemistry, 113: 144-148, 1981.
Burlage et al. "Living Biosensors for the Management and Manipulation of Microbial Consortia",Annual. Rev. Microbiol., 48: 291-309, 1994.
Mrksich et al. "Using Self-Assembled Monolayers to Understand the Interactions of Man-Made Surfaces With Proteins and Cells", Annual Reviews in Biophysics and Biomolecular Structure, 25: 55-78, 1996.
Singhvi et al. "Engineering Cell Shape and Function", Science, 264: 696-698, 1994.
Riedel et al. "Arxula Adeninivorans Based Sensor for the Estimation of Bod", Analytical Letters, 31(1): 1-12, 1998.
Simonian et al. "Microbial Biosensors Based on Potentiometric Detection", Methods in Biotechnology,6, chapter 17: 237-248, 1998.
Arikawa et al. "Microbial Biosensors Based on Respiratory Inhibition", Methos in Biotehnology,6, chapter 16: 225-235, 1998.

Communication Pursuant to Article 94(3) EPC Dated Feb. 13, 2009 From the European Patent Office Re.: Application No. 05763452.9.
Kiguchi et al. "Induction of Urokinase-Type Plasminogen Activator by the Anthracycline Antibiotic in Human RC-K8 Lymphoma and H69 Lung-Carcinoma Cells", International Journal of Cancer, 93: 792-797, 2001.
Schroeder et al. "Coordination of Cell Growth in Cocultures by A Genetic Proliferation Control System", Biotechnology and Bioengineering, 78(3): 346-352, 2002.
Baruch et al. "Enzyme Activity—It's All About Image", Trends in Cell Biology, 14(1): 29-35, 2004.
Hestbjerg Hansen et al. "Quantification of Bioavailable Chlortetracycline in Pig Feces Using A Bacterial Whole-Cell Biosensor", Veterinary Microbiology, 87: 51-57, 2002.
Kovacic et al. "Mechanisms of Carcinogenesis: Focus on Oxidative Stress and Electron Transfer", Current Medicinal Chemistry, 8: 773-796, 2001.
Suehiro et al. "The Dielectrophoretic Movement and Positioning of a Biological Cell Using a Three-Dimensional Grid Electrode System", J. Phys. D. Appl. Phys, vol. 31 p. 3298-3305, 1998.
Yamamura et al. "Single-Cell Microarray for Analyzing Cellular Response", Analytical Chemistry, 77(24): 8050-8056, 2005.
International Search Report Dated Mar. 2, 2005 From the International Searching Authority Re.: Application No. PCT/IL04/00661.
International Search Report Dated Feb. 7 2006 From the International Searching Authority Re.: Application No. PCT/IL2005/001078.
International Search Report Dated Nov. 7, 2005 From the International Searching Authority Re.: PCT/IL2005/000801.
International Search Report Dated Nov. 9, 2004 From the International Searching Authority Re.: Application No. PCT/IL04/00571.
International Search Report Dated Sep. 11, 2006 From the International Seaching Authority Re.: Application No. PCT/IL2006/000483.
International Search Report Dated Feb. 16, 2005 From the International Searching Authority Re.: PCT/IL04/00194.
International Search Report Dated Jan. 17, 2003 From the International Searching Authority Re.: Application No. PCT/IL01/00992.
International Search Report Dated Feb. 21, 2006 From the International Searching Authority Re.: Application No. PCT/IL2005/000914.
International Search Report Dated Sep. 21, 2007 From the International Searching Authority Re.: PCT/IL2006/001487.
International Search Report Dated Dec. 27, 2001 From the International Searching Authority Re.: Application No. PCT/IL01/00443.
Official Action Dated Mar. 5, 2010 From the US Patent and Trademark Office Re.: U.S. Appl. No. 10/561,839.
Supplementary European Search Report Dated Oct. 26, 2004 From the European Patent Office Re.: Application No. EP 01934272.
Written Opinion Dated Nov. 15, 2005 From the International Searching Authority Re.: Application No. PCT/IL2005/000719.
Deutsch et al. "Microplate Cell-Retaining Methodology for High-Content Analysis of Individual Non-Adherent Unanchored Cells in A Population", Biomedical Microdevices, 8: 361-374, 2006.
Seahorse Bioscience "Designed for Scientists by Scienctists. How the XF24 Extracellular Flux Analyzer Works", Product Description, Seahorse Bioscience, 4 P., 2008.
Seahorse Bioscience "XF24 Extracellular Flux Analyzer", Product Description, Seahorse Bioscience, 3 P., 2008.
Final OA of Nov. 14, 2008.
Final OA of Sep. 20, 2007.
OA Missing Parts Nov. 14, 2006.
OA of Dec. 14, 2007.
OA of Dec. 18, 2006.
OA of Feb. 19, 2008.
OA of Jan. 25, 2007.
OA of Feb. 5, 2007.
Office Action of Mar. 23, 2005.
Communication Pursuant to Article 94(3) EPC Dated Feb. 29, 2008 From the European Patent Office Re.: 05763452.9.
International Preliminary Report on Patentability Dated Feb. 2, 2006 From the International Bureau of WIPO Re.: Application No. PCT/IL2004/000661.

(56) References Cited

OTHER PUBLICATIONS

International Preliminary Report on Patentability Dated May 3, 2007From the International Bureau of WIPO Re.: Application No. PCT/IL2005/001078.
International Preliminary Report on Patentability Dated Mar. 8, 2007 From the International Bureau of WIPO Re.: Application No. PCT/IL2005/000914.
International Preliminary Report on Patentability Dated Jul. 10, 2008 From the International Bureau of WIPO Re.: Application No. PCT/IL2006/001487.
International Preliminary Report on Patentability Dated Jan. 18, 2007 From the International Bureau of WIPO Re.: Application No. PCT/IL2005/000719.
International Preliminary Report on Patentability Dated Nov. 28, 2007 From the International Bureau of WIPO Re.: Application No. PCT/IL2006/000483.
International Preliminary Report on Patentability Dated Aug. 9, 2007 From the International Bureau of WIPO Re.: Application No. PCT/IL2005/000801.
Invitation to Pay Additional Fees Dated Mar. 3, 2009 From the International Searching Authority Re.: Application No. PCT/IL 08/01492.
Notice of Allowance Dated Mar. 4, 2008 From the US Patent and Trademark Office Re.: U.S. Appl. No. 10/546,784.
Office Action Dated May 15, 2008 From the Israeli Patent Office Re.: U.S. Appl. No. 10/916,380.
Office Action Dated Mar. 8, 2006 From the Israeli Patent Office Re.: Application No. 138314.
Office Action Dated Jul. 19, 2006 From the Israeli Patent Office Re.: Application No. 138314.
Office Action Dated Mar. 22, 2009 From the Israeli Patent Office Re.: Application No. 170492 and Its Translation Into English.
Office Action Dated Sep. 29, 2003 From the Israeli Patent Office Re.: Application No. 136232.
Official Action Dated Feb. 5, 2007 From the US Patent and Trademark Office Re.: U.S. Appl. No. 10/916,380.
Official Action Dated Dec. 14, 2007 From the US Patent and Trademark Office Re.: U.S. Appl. No. 10/916,380.
Official Action Dated Nov. 14, 2008 From the US Patent and Trademark Office Re.: U.S. Appl. No. 10/492,531.
Official Action Dated Oct. 16, 2006 From the US Patent and Trademark Office Re.: U.S. Appl. No. 10/492,531.
Official Action Dated Dec. 18, 2006 From the US Patent and Trademark Office Re.: U.S. Appl. No. 10/276,080.
Official Action Dated Sep. 20, 2007 From the US Patent and Trademark Office Re.: U.S. Appl. No. 10/492,531.
Official Action Dated Aug. 25, 2006 From the US Patent and Trademark Office Re.: U.S. Appl. No. 10/276,080.
Official Action Dated Jan. 25, 2007 From the US Patent and Trademark Office Re.: U.S. Appl. No. 10/492,531.
Official Action Dated Aug. 28, 2007 From the US Patent and Trademark Office Re.: U.S. Appl. No. 10/916,380.
Response Dated Apr. 29, 2005 to Communication Pursuant to Article 96(2) EPC of Dec. 23, 2004 From the European Patent Office Re.: Application No. 01934272.4.
Supplementary Partial European Search Report Dated Feb. 20, 2006 From the European Patent Office Re.: Application No. 04714873.9.
Translation of Notice of Reason for Rejection Dated Nov. 27, 2007 From Japanese Patent Office Re.: Application No. 2003-538325.
International Preliminary Report on Patentability Dated May 27, 2010 From the International Bureau of WIPO Re.: Application No. PCT/IL2008/001492.
International Preliminary Report on Patentability Dated May 27, 2010 From the International Preliminary Examining Authority Re.: Application No. PCT/IL2008/001678.
Response Dated May 25, 2010 to Official Action of Jan. 28, 2010 From the US Patent and Trademark Office Re.: U.S. Appl. No. 10/492,531.

Response Dated Jun. 15, 2010 to Notice of Reason for Rejection of Mar. 30, 2010 From the Japanese Patent Office Re. Application No. 2006-502647.
Response Dated Jun. 7, 2010 to Official Action of Mar. 5, 2010 From the US Patent and Trademark Office Re.: U.S. Appl. No. 10/561,839.
Communication Relating to the Results of the Partial International Search Dated May 20, 2009 From the International Searching Authority Re.: Application No. PCT/IL2008/001678.
International Search Report Dated May 13, 2009 From the International Searching Authority Re.: Application No. PCT/IL08/01492.
Written Opinion Dated May 13, 2009 From the International Searching Authority Re.: Application No. PCT/IL08/01492.
Ducrée "Polymer Prototyping von mikrofluidischen Strukturen. Projekt", Insitut für Mikrosystemtechnik, Albert-Ludwigs-Universität Freiburg i. Br., IMTEK, 4 P., 2004. Retrieved From the Internet: http://images.google.com/imgres?imgurl=http://www.imtek.de/anwendungen/content/upload/vorlesung/133/133-03-14__prototyping_hydrophobic.jpg&imgrefurl=http://www.imtek.de/content/projekte.php%3F1s%3D3%26nr%3D133&h=299&w=429&.
Craighead et al. Textured Surfaces: Optical Storage and Other Applications,Journal of Vacuum Science and Technology 20 (3): 316, 1982. Abstract.
Communication Pursuant to Article 94(3) EPC Dated Aug. 9, 2010 From the European Patent Office Re. Application No. 01982673.4.
Communication Pursuant to Article 94(3) EPC Dated Aug. 6, 2010 From the European Patent Office Re.: Application No. 04714873.9.
Office Action Dated Jul. 1, 2010 From the Israeli Patent Office Re.: Application No. 172724 and Its Translation Into English.
Official Action Dated Aug. 17, 2010 From the US Patent and Trademark Office Re.: U.S. Appl. No. 10/561,839.
Response Dated Aug. 30, 2010 to Official Action of Jul. 13, 2009 From the US Patent and Trademark Office Re.: U.S. Appl. No. 11/660,783.
Response Dated Aug. 30, 2010 to Official Action of Feb. 23, 2010 From the US Patent and Trademark Office Re.: U.S. Appl. No. 12/084,462.
Official Action Dated Sep. 10, 2010 From the US Patent and Trademark Office Re.: U.S. Appl. No. 11/646,317.
Communication Pursuant to Rules 161(1) and 162 EPC Dated Aug. 25, 2010 From the European Patent Office Re. Application No. 08865081.7.
Official Action Dated Sep. 14, 2010 From the US Patent and Trademark Office Re.: U.S. Appl. No. 11/631,737.
Response Dated Sep. 21, 2010 to Communication Pursuant to Rules 161(1) and 162 EPC of Aug. 25, 2010 From the European Patent Office Re. Application No. 08865081.7.
Communication Pursuant to Article 94(3) EPC Dated Jun. 16, 2009 From the European Patent Office Re.: Application No. 04714873.9.
Office Action Dated Jul. 14, 2009 From the Israeli Patent Office Re.: Application No. 172724 and Its Translation Into English.
Official Action Dated Jul. 13, 2009 From the US Patent and Trademark Office Re.: U.S. Appl. No. 11/660,783.
Official Action Dated Jun. 29, 2009 From the US Patent and Trademark Office Re.: U.S. Appl. No. 10/492,531.
Stevens et al. "Quorum Sensing in Vibrio Fischeri: Essential Elements for Activation of the Luminescence Genes", Journal of Bacteriology, 179(2): 557-562, Jan. 1997.
Official Action Dated Sep. 29, 2010 From the US Patent and Trademark Office Re.: U.S. Appl. No. 11/883,028.
Office Action Dated Oct. 5, 2010 From the Israel Patent Office Re. Application No. 184818 and Its Translation Into English.
Response Dated Oct. 10, 2010 to Notice of Reason for Rejection of Jul. 23, 2010 From the Japanese Patent Office Re.: Application No. 2006-502647.
Official Action Dated Sep. 23, 2010 From the US Patent and Trademark Office Re.: U.S. Appl. No. 10/492,531.
Official Action Dated Sep. 23, 2010 From the US Patent and Trademark Office Re.: U.S. Appl. No. 11/646,294.
Supplementary European Search Report Dated Feb. 20, 2006 From the European Patent Office Re.: Application No. 04714873.9.
Arikawa et al. "Microbial Biosensors Based on Respiratory Inhibition", Methos in Biotechnology, 6(Chap.16): 225-235, 1998.

(56) References Cited

OTHER PUBLICATIONS

Burlage et al. "Living Biosensors for the Management and Manipulation of Microbial Consortia", Annual Reviews in Microbiology, 48: 291-309, 1994.
Dive et al. "Improved Methodology for Intracellular Enzyme Reaction and Inhibition Kinetics by Flow Cytometry", Cytometry Journal of Society for Analytical Cytology, 8(6): 552-561, 1987.
Dolbeare "Fluorescent Staining of Enzymes for Flow Cytometry", Methods in Cell Biology, 33(Chap.8): 81-88, 1990.
Ducrée "Polymer Prototyping von mikrofluidischen Strukturen. Projekt", Insitut für Mikrosystemtechnik, Albert-Ludwigs-Universität Freiburg i. Br., IMTEK, 4 P., 2004. Rretrieved from the Internet: http://images.google.com/imgres?imgurl=http://www.imtek.de/anwendungen/content/upload/vorlesung/133/133-03-14_prototyping_hydrophobic.jpg&imgrefurl=http://www.imtek.de/content/projekte.php%3F1s%3D3%26nr%3D133&h=299&w=429&.
Klingel et al. "Flow Cytometric Determination of Serine Proteinase Activities in Living Cells With Rhodamine 110 Substrates", Methods in Cell Biology, 41(Chap.29): 449-460, 1994.
Nooter et al. "On-Line Flow Cytometry. A Versatile Method for Kinetic Measurement", Methods in Cell Biology, 41(Chap.32): 509-526, 1994.
Simonian et al. "Microbial Biosensors Based on Potentiometric Detection", Methods in Biotechnology, 6(Chap.17): 237-248, 1998.
Tixier et al. Catching and Attaching Cells Using an Array of Microholes, Abstract of the 2nd Conference of the Society for Chemistry and Micro Systems, p. 60, 2000.
Turek et al. "Leucine Aminopeptidase Activity by Flow Cytometry", Methods in Cell Biology, 41(Chap.30): 461-468, 1994.
Watson et al. "Enzyme Kinetics", Methods in Cell Biology, 41: 469-508, 1994.
Translation of Notice of Reason for Rejection Dated Nov. 27, 2007 From Japanes Patent Office Re.: Application No. 2003-538325.
Craighead et al. "Textured Surfaces: Optical Storage and Other Applications", Journal of Vacuum Science and Technology 20 (3): 316, 1982. Abstract.
Ducrée "Polymer Prototyping von mikrofluidischen Strukturen. Projekt", Insitut für Mikrosystemtechnik, Albert-Ludwigs-Universität Freiburg i. Br., IMTEK, 4 P., 2004. Retrieved From the Internet: http://images.google.com/imgres?imgurl=http://www.imtek.de/anwendungen/content/upload/vorlesung/133/133-03-14_prototyping_hydrophobic.jpg&imgrefurl=http://www.imtek.de/content/projekt.php%3F1s%3D3%26nr%3D133&h=299&w=429&.
Hansen et al. "Quantification of Bioavailable Chlortetracycline in Pig Feces Using a Bacterial Whole-Cell Biosensor", Veterinary Microbiology, 87: 51-57, 2002.
Tixier et al. Catching and Attaching Cells Using an Array of Microholes, Abstract of the 2nd Conference of the Society for Chemistry and Mirco Systems, p. 60, 2000.
Interview Summary Dated Feb. 11, 2011 From the US Patent and Trademark Office Re.: U.S. Appl. No. 11/883,028.
Response Dated Jan. 20, 2011 to Official Action of Oct. 27, 2010 From the US Patent and Trademark Office Re.: U.S. Appl. No. 12/890,668.
Official Action Dated Feb. 1, 2011 From the US Patent and Trademark Office Re.: U.S. Appl. No. 11/631,737.
Office Action Dated Feb. 28, 2011 From the Israel Patent Office Re. Application No. 180568 and Its Translation Into English.
Official Action Dated Mar. 9, 2011 From the US Patent and Trademark Office Re.: U.S. Appl. No. 11/660,783.
Response Dated Mar. 22, 2011 to Official Action of Dec. 22, 2010 From the US Patent and Trademark Office Re.: U.S. Appl. No. 11/883,028.
Response Dated Feb. 23, 2011 to Official Action of Jan. 19, 2011 From the US Patent and Trademark Office Re.: U.S. Appl. No. 11/646,317.
Invitation Pursuant to Article 94(3) and Rule 71(1) EPC Dated Apr. 8, 2011 From the European Patent Office Re. Application No. 01982673.4.
Notice of Allowance Dated Mar. 31, 2011 From the US Patent and Trademark Office Re.: U.S. Appl. No. 12/890,668.
Official Action Dated Mar. 31, 2011 From the US Patent and Trademark Office Re.: U.S. Appl. No. 10/492,531.
European Search Report and the European Search Opinion Dated Aug. 1, 2011 From the European Patent Office Re. Application No. 10183774.8.
Office Action Dated Apr. 12, 2011 From the Israel Patent Office Re.: Application No. 173170 and Its Translation Into English.
Gonzalez et al. "Cell-Based Assays and Instrumentation for Screening Ion-Channels Targets", Drug Discovery Today, DDT, XP001026838, 4(9): 431-439, Sep. 1, 1999.
Communication Pursuant to Rules 70(2) and 70a(2) EPC and Reference to Rule 39(1) EPC Dated Sep. 5, 2011 From the European Patent Office Re. Application No. 10183774.8.
Official Action Dated Oct. 18, 2011 From the US Patent and Trademark Office Re.: U.S. Appl. No. 12/084,462.
Official Action Dated Oct. 19, 2011 From the US Patent and Trademark Office Re. U.S. Appl. No. 12/155,643.
Communication Pursuant to Article 94(3) EPC Dated Nov. 16, 2011 From the European Patent Office Re. Application No. 04744911.1.
Response Dated Nov. 1, 2011 to Official Action of Oct. 19, 2011 From the US Patent and Trademark Office Re. U.S. Appl. No. 12/155,643.
Response Dated Nov. 21, 2011 to Communication Pursuant to Article 94(3) EPC of Aug. 4, 2011 From the European Patent Office Re. Application No. 08865081.7.
Response Dated Nov. 30, 2011 to Office Action of Jul. 1, 2010 From the Israeli Patent Office Re.: Application No. 172724.
Response Dated Oct. 31, 2011 to Official Action of Jul. 21, 2011 From the US Patent and Trademark Office Re. U.S. Appl. No. 12/712,232.
Communication Pursuant to Article 94(3) EPC Dated Aug. 4, 2011 From the European Patent Office Re. Application No. 08865081.7.
Notice of Allowance Dated Jun. 9, 2011 From the US Patent and Trademark Office Re.: U.S. Appl. No. 11/883,028.
Response Dated Jun. 29, 2011 to Official Action of Mar. 31, 2011 From the US Patent and Trademark Office Re.: U.S. Appl. No. 10/492,531.
Official Action Dated Oct. 27, 2010 From the US Patent and Trademark Office Re.: U.S. Appl. No. 12/890,668.
Official Action Dated Jan. 19, 2011 From the US Patent and Trademark Office Re.: U.S. Appl. No. 11/646,317.
Response Dated Jan. 24, 2011 to Official Action of Sep. 23, 2010 From the US Patent and Trademark Office Re.: U.S. Appl. No. 11/646,294.
Official Action Dated Nov. 1, 2010 From the US Patent and Trademark Office Re.: U.S. Appl. No. 11/883,028.
Response Dated Nov. 8, 2010 to Official Action of Sep. 10, 2010 From the US Patent and Trademark Office Re.: U.S. Appl. No. 11/646,317.
Response Dated Nov. 15, 2010 to Official Action Dated Sep. 14, 2010 From the US Patent and Trademark Office Re.: U.S. Appl. No. 11/631,737.
Response Dated Nov. 15, 2010 to Official Action of Nov. 1, 2010 From the US Patent and Trademark Office Re.: U.S. Appl. No. 11/883,028.
Response Dated Dec. 16, 2010 to Official Action of Aug. 17, 2010 From the US Patent and Trademark Office Re.: U.S. Appl. No. 10/561,839.
Response Dated Dec. 20, 2010 to Official Action of Sep. 23, 2010 From the US Patent and Trademark Office Re.: U.S. Appl. No. 10/492,531.
Response Dated Nov. 30, 2010 to Communication Pursuant to Article 94(3) EPC of Aug. 5, 2010 From the European Patent Office Re. Application No. 05757567.2.
Response Dated Jul. 11, 2011 to Official Action of Mar. 16, 2011 From the US Patent and Trademark Office Re. U.S. Appl. No. 10/561,839.

(56) References Cited

OTHER PUBLICATIONS

Response Dated Jun. 28, 2011 to Invitation Pursuant to Rule 63(1) EPC of May 3, 2011 From the European Patent Office Re. Application No. 10183774.8.
Official Action Dated Jul. 21, 2011 From the US Patent and Trademark Office Re. U.S. Appl. No. 12/712,232.
Communication Pursuant to Article 94(3) EPC Dated Aug. 29, 2011 From the European Patent Office Re. Application No. 04745001.0.
Official Action Dated Aug. 31, 2011 From the US Patent and Trademark Office Re.: U.S. Appl. No. 11/660,783.
Response Dated Sep. 19, 2011 to Notice of Non-Compliant Amendment of Aug. 18, 2011 From the US Patent and Trademark Office Re.: U.S. Appl. No. 12/084,462.
Partial European Search Report Dated Oct. 27, 2011 From the European Patent Office Re. Application No. 11170000.1.
Official Action Dated Sep. 22, 2011 From the US Patent and Trademark Office Re.: U.S. Appl. No. 11/646,294.
Official Action Dated Dec. 19, 2011 From the US Patent and Trademark Office Re.: U.S. Appl. No. 10/492,531.
Official Action Dated Nov. 22, 2011 From the US Patent and Trademark Office Re.: U.S. Appl. No. 11/646,317.
Official Action Dated Nov. 23, 2011 From the US Patent and Trademark Office Re.: U.S. Appl. No. 10/561,839.
Communication Pursuant to Rule 58 EPC or Rule 159 EPC Dated Nov. 24, 2010 From the European Patent Office Re. Application No. 10183774.8.
Response Dated Jan. 3, 2011 to Communication Pursuant to Rule 58 EPC or Rule 159 EPC of Nov. 24, 2010 From the European Patent Office Re. Application No. 10183774.8.
Response Dated Feb. 7, 2011 to Communication Pursuant to Article 94(3) EPC of Aug. 6, 2010 From the European Patent Office Re.: Application No. 04714873.9.
Notice of Non-Compliant Amendment Dated Aug. 18, 2011 From the US Patent and Trademark Office Re.: U.S. Appl. No. 12/084,462.
Reponse Dated Aug. 4, 2011 to Official Action of Apr. 15, 2011 From the US Patent and Trademark Office Re.: U.S. Appl. No. 12/084,462.
Response Dated Aug. 4, 2011 to Official Action of May 23, 2011 From the US Patent and Trademark Office Re.: U.S. Appl. No. 11/646,317.
Response Dated Aug. 17, 2011 to Office Action of Apr. 12, 2011 From the Israel Patent Office Re.: Application No. 173170.
Response Dated Aug. 22, 2011 to Official Action of Apr. 22, 2011 From the US Patent and Trademark Office Re.: U.S. Appl. No. 11/646,294.
Notification of European Publication Number and Information on the Applicaiton of Article 67(3) EPC Dated May 18, 2011 From the European Patent Office Re. Application No. 10183774.8.
Official Action Dated May 23, 2011 From the US Patent and Trademark Office Re.: U.S. Appl. No. 11/646,317.
Response Dated May 31, 2011 to Invitation Pursuant to Article 94(3) and Rule 71(1) EPC of Apr. 8, 2011 From the European Patent Office Re. Application No. 01982673.4.
Response Dated Jan. 12, 2011 to Office Action of Oct. 5, 2010 From the Israel Patent Office Re. Application No. 184818.
Official Action Dated Mar. 16, 2011 From the US Patent and Trademark Office Re. U.S. Appl. No. 10/561,839.
Response Dated Feb. 17, 2011 to Communication Pursuant to Article 94(3) EPC of Aug. 9, 2010 From the European Patent Office Re. Application No. 01982673.4.
Cornell University "All About Birds: Optical Quality", Cornell University, 2 P., Oct. 3, 2010.
Invitation Pursuant to Rule 63(1) EPC Dated May 3, 2011 From the European Patent Office Re. Application No. 10183774.8.
Official Action Dated Apr. 15, 2011 From the US Patent and Trademark Office Re.: U.S. Appl. No. 12/084,462.
Official Action Dated Apr. 22, 2011 From the US Patent and Trademark Office Re.: U.S. Appl. No. 11/646,294.
Official Action Dated Dec. 22, 2010 From the US Patent and Trademark Office Re.: U.S. Appl. No. 11/883,028.

Proceeding Further With the European Patent Application Pursuant to Rule 70(2) EPC Dated Nov. 10, 2009 From the European Patent Office Re. Application No. 04745001.0.
Response Dated Jan. 2, 2011 to Proceeding Further With the European Patent Application Pursuant to Rule 70(2) EPC of Nov. 10, 2009 From the European Patent Office Re. Application No. 04745001.0.
Response Dated Jun. 1, 2011 to Official Action of Feb. 1, 2011 From the US Patent and Trademark Office Re.: U.S. Appl. No. 11/631,737.
Response Dated Jun. 9, 2011 to Official Action of Mar. 9, 2011 From the US Patent and Trademark Office Re.: U.S. Appl. No. 11/660,783.
Applicant-Initiated Interview Summary Dated Dec. 19, 2012 From the US Patent and Trademark Office Re. U.S. Appl. No. 12/742,730.
Applicant-Initiated Interview Summary Dated Dec. 20, 2012 From the US Patent and Trademark Office Re. U.S. Appl. No. 13/184,631.
Office Action Dated Dec. 17, 2012 From the Israel Patent Office Re. Application No. 205769 and Its Translation Into English.
European Search Report and the European Search Opinion Dated Mar. 13, 2012 From the European Patent Office Re. Application No. 11170000.1.
Office Action Dated Feb. 2, 2012 From the Israel Patent Office Re.: Application No. 173170 and Its Translation Into English.
Official Action Dated Mar. 1, 2012 From the US Patent and Trademark Office Re.: U.S. Appl. No. 12/084,462.
Official Action Dated Mar. 6, 2012 From the US Patent and Trademark Office Re. U.S. Appl. No. 12/155,643.
Official Action Dated Oct. 18, 2011 From the US Patent and Trademark Office Re.: U.S. Appl. No. 11/631,737.
Ducree "Polymer Prototyping von mikrofluidischen Strukturen. Projekt", Insitut f?r Mikrosystemtechnik, Albert-Ludwigs-Universit?t Freiburg i. Br., IMTEK, 4 P., 2004. Retrieved From the Internet: http://images.google.com/imgres?imgurl=http://www.imtek.de/anwendungen/content/upload/vorlesung/133/133-03-14_prototyping_hydrophobic.jpg&imgrefurl=http://www.imtek.de/content/projekte.php%3F1s%3D3%26nr%3D133&h=299&w=429&.
Suehiro et al. "The Dielectrophoretic Movement and Positioning of a Biological Cell Using a Three-Dimensional Grid Electrode System", Journal of Physics D: Applied Physics, 31: 3298-3305, 1998.
Communication Pursuant to Article 94(3) EPC Dated Apr. 11, 2012 From the European Patent Office Re. Application No. 10183774.8.
Communication Pursuant to Rules 70(2) and 70a(2) EPC and Reference to Rule 39(1) EPC Dated Apr. 16, 2012 From the European Patent Office Re. Application No. 11170000.1.
Communication Pursuant to Article 94(3) EPC Dated Sep. 26, 2012 From the European Patent Office Re. Application No. 04714873.9.
Official Action Dated Jul. 30, 2012 From the US Patent and Trademark Office Re. U.S. Appl. No. 12/155,643.
Official Action Dated Aug. 2, 2012 From the US Patent and Trademark Office Re. U.S. Appl. No. 12/712,232.
Communication Pursuant to Article 94(3) EPC Dated May 22, 2012 From the European Patent Office Re.: Application No. 04714873.9.
Communication Pursuant to Rules 70(2) and 70a(2) EPC Dated Aug. 20, 2012 From the European Patent Office Re. Application No. 08848869.7.
Office Action Dated Aug. 12, 2012 From the Israeli Patent Office Re.: Application No. 172724 and Its Translation Into English.
Supplementary European Search Report and the European Search Opinion Dated Aug. 1, 2012 From the European Patent Office Re. Application No. 08848869.7.
Communication Pursuant to Article 94(3) EPC Dated Sep. 6, 2012 From the European Patent Office Re. Application No. 10183774.8.
Communication Pursuant to Article 94(3) EPC Dated Jun. 25, 2012 From the European Patent Office Re. Application No. 04745001.0.
Official Action Dated Jun. 21, 2012 From the US Patent and Trademark Office Re.: U.S. Appl. No. 10/492,531.
Communication Pursuant to Article 94(3) EPC Dated Jun. 25, 2012 From the European Patent Office Re. Application No. 04744911.1.
Official Action Dated Jun. 22, 2012 From the US Patent and Trademark Office Re. U.S. Appl. No. 13/019,320.
Lee et al. "An Equibiaxial Strain System for Cultured Cells", The American Journal of Physiology, XP008152868, 271(4): C1400-C1408, Oct. 1996.

(56) References Cited

OTHER PUBLICATIONS

Tschumperlin et al. "Equibiaxial Deformation-Induced Injury of Alveolar Epithelial Cells In Vitro", American Journal of Physiology, 275(6/Pt.1): L1173-L1183, Jan. 1, 1998.
Official Action Dated Nov. 14, 2012 From the US Patent and Trademark Office Re. U.S. Appl. No. 13/184,631.
Official Action Dated Nov. 16, 2012 From the US Patent and Trademark Office Re. U.S. Appl. No. 12/742,730.
Restriction Official Action Dated Nov. 15, 2012 From the US Patent and Trademark Office Re. U.S. Appl. No. 12/810,868.
Communication Pursuant to Article 94(3) EPC Dated Nov. 23, 2012 From the European Patent Office Re. Application No. 01982673.4.
Office Action Dated Sep. 20, 2012 From the Israel Patent Office Re. Application No. 138314.
Official Action Dated Sep. 28, 2012 From the US Patent and Trademark Office Re. U.S. Appl. No. 10/561,839.
Translation of Office Action Dated Sep. 20, 2012 From the Israel Patent Office Re. Application No. 138314.
Office Action Dated Dec. 31, 2012 From the Israel Patent Office Re. Application No. 206588 and Its Translation Into English.
Official Action Dated Dec. 16, 2012 From the US Patent and Trademark Office Re. U.S. Appl. No. 13/019,320.
Official Action Dated Feb. 11, 2013 From the US Patent and Trademark Office Re. U.S. Appl. No. 12/742,730.
Official Action Dated Feb. 13, 2013 From the US Patent and Trademark Office Re. U.S. Appl. No. 12/810,868.
Official Action Dated Mar. 15, 2013 From the US Patent and Trademark Office Re. U.S. Appl. No. 13/019,320.
Advisory Action Before the Filing of an Appeal Brief Dated Aug. 29, 2013 From the US Patent and Trademark Office Re. U.S. Appl. No. 13/019,320.
Summons to Attend Oral Proceedings Pursuant to Rule 115(1) EPC Dated Aug. 14, 2013 From the European Patent Office Re. Application No. 01982673.4.
Summons to Attend Oral Proceedings Pursuant to Rule 115(1) EPC Dated Aug. 14, 2013 From the European Patent Office Re. Application No. 10183774.8.
Official Action Dated Mar. 13, 2013 From the US Patent and Trademark Office Re.: U.S. Appl. No. 10/492,531.
Restriction Official Action Dated Apr. 25, 2013 From the US Patent and Trademark Office Re. U.S. Appl. No. 13/651,522.
Notice of Allowance Dated Apr. 1, 2013 From the US Patent and Trademark Office Re. U.S. Appl. No. 13/184,631.
Communication Pursuant to Article 94(3) EPC Dated Oct. 4, 2013 From the European Patent Office Re. Application No. 04745001.0.
Office Action Dated May 16, 2013 From the Israel Patent Office Re. Application No. 173170 and Its Translation Into English.
Official Action Dated May 14, 2013 From the US Patent and Trademark Office Re. U.S. Appl. No. 12/742,730.
Office Action Dated Apr. 12, 2011 From the Israel Patent Office Re. Application No. 173170 and Its Translation Into English.
Notice of Allowance Dated Jan. 7, 2008 From the US Patent and Trademark Office Re.: U.S. Appl. No. 10/938,951.
Office Action Dated Apr. 12, 2007 From the Israeli Patent Office Re.: Application No. 138314.
Official Action Dated Feb. 19, 2008 From the US Patent and Trademark Office Re.: U.S. Appl. No. 10/492,531.
Official Action Dated Oct. 22, 2007 From the US Patent and Trademark Office Re.: U.S. Appl. No. 11/492,531.
Official Action Dated Feb. 23, 2010 From the US Patent and Trademark Office Re.: U.S. Appl. No. 12/084,462.
Official Action Dated Jan. 28, 2010 From the US Patent and Trademark Office Re.: U.S. Appl. No. 10/492,531.
Response Dated Dec. 29, 2009 to Office Action of Sep. 2, 2009 From the Israel Patent Office Re.: Application No. 200559.
Translation of Notice of Reason for Rejection Dated Mar. 30, 2010 From the Japanese Patent Office Re.: Application No. 2006-502647.
Tixicr et al. Catching and Attaching Cells Using An Array of Microholes, 2nd Conference of the Society for Chemistry and Micro Systems, p. 60, 2000. Abstract.

* cited by examiner

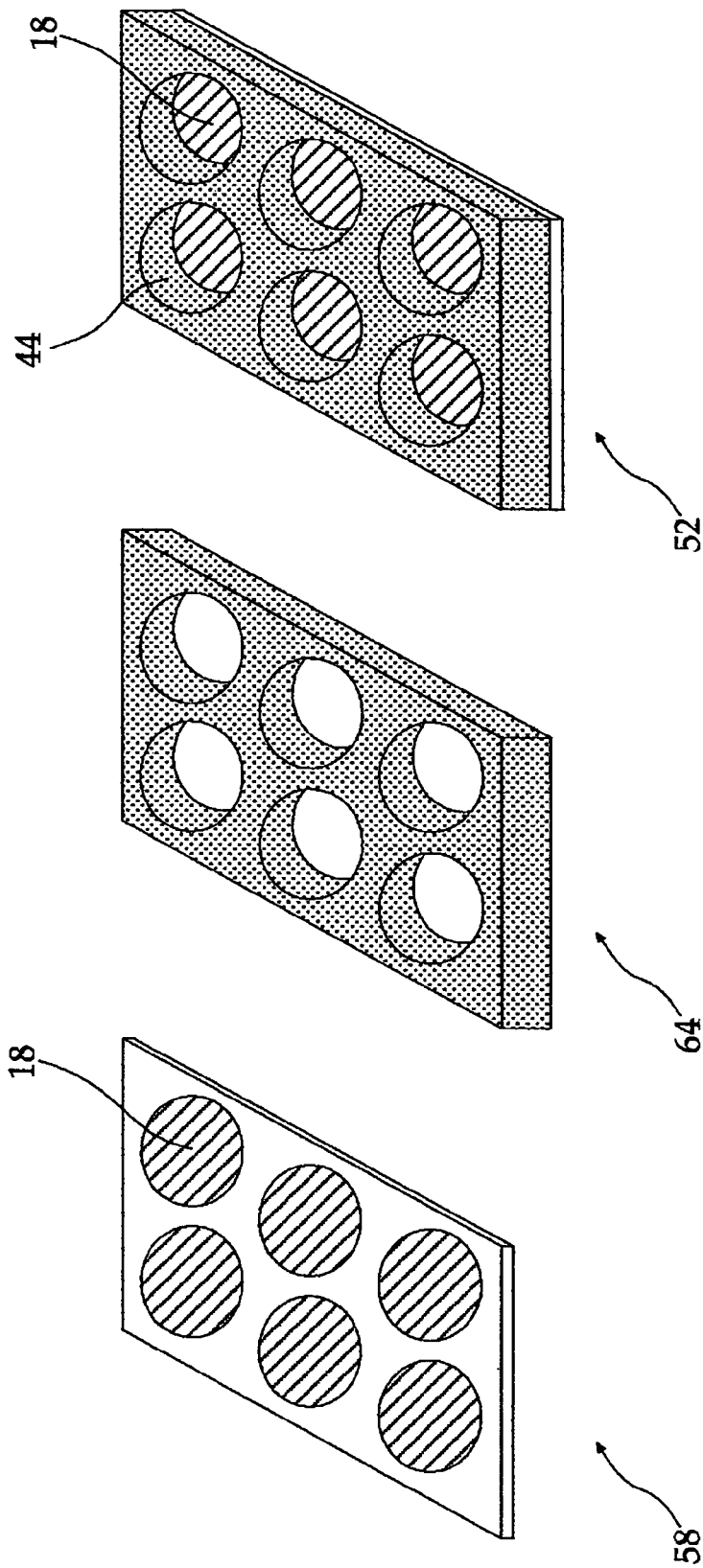

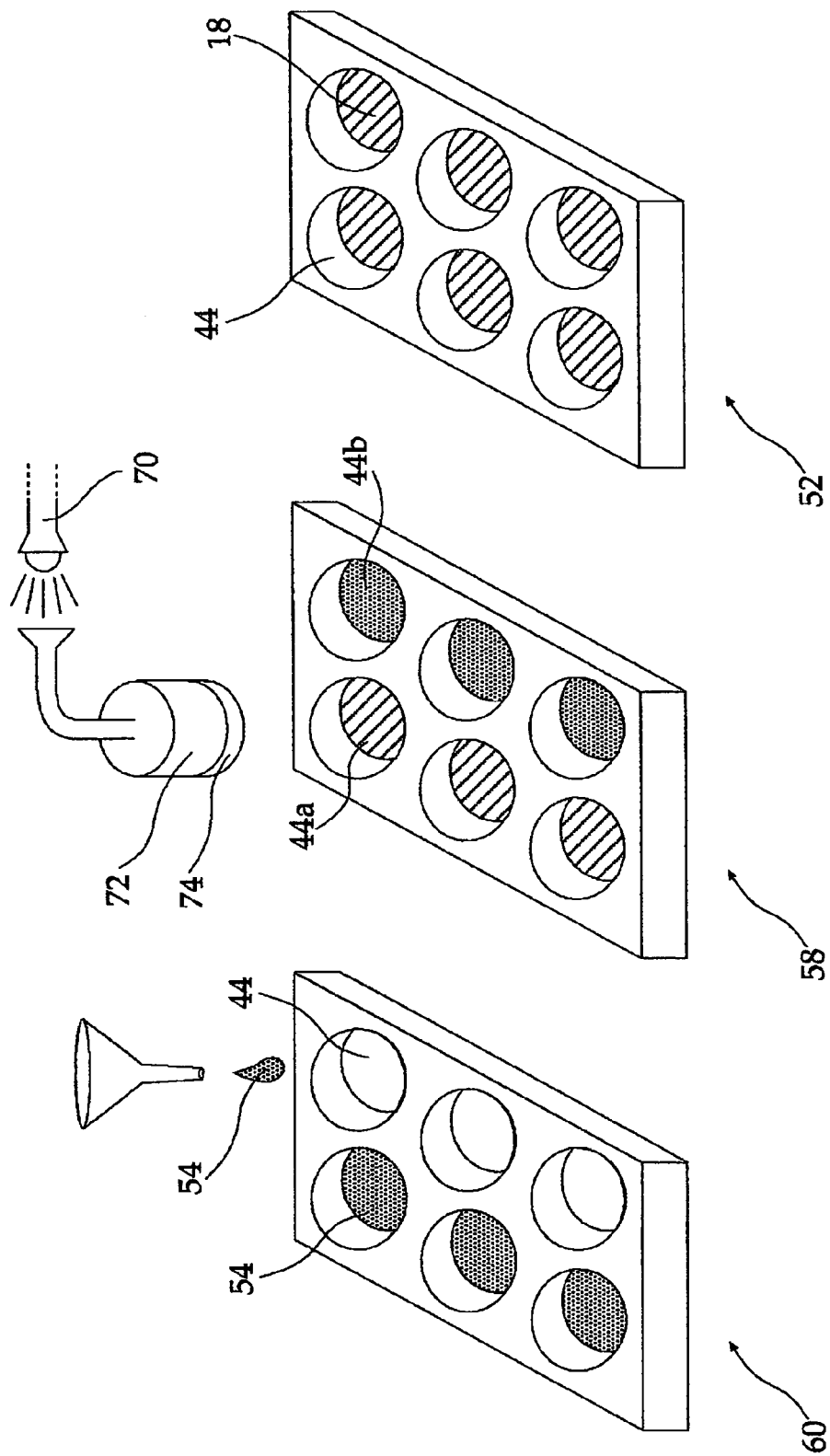

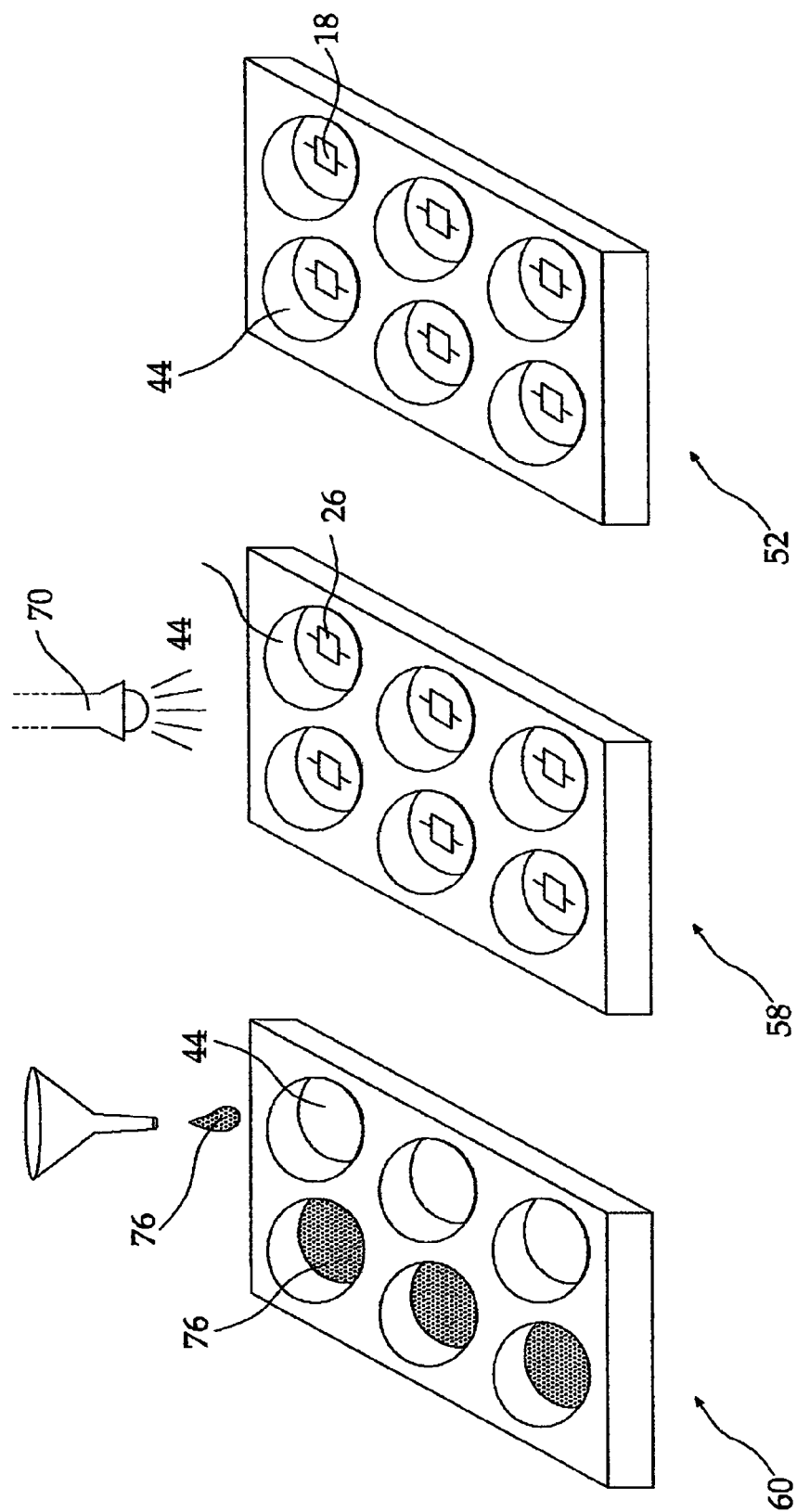

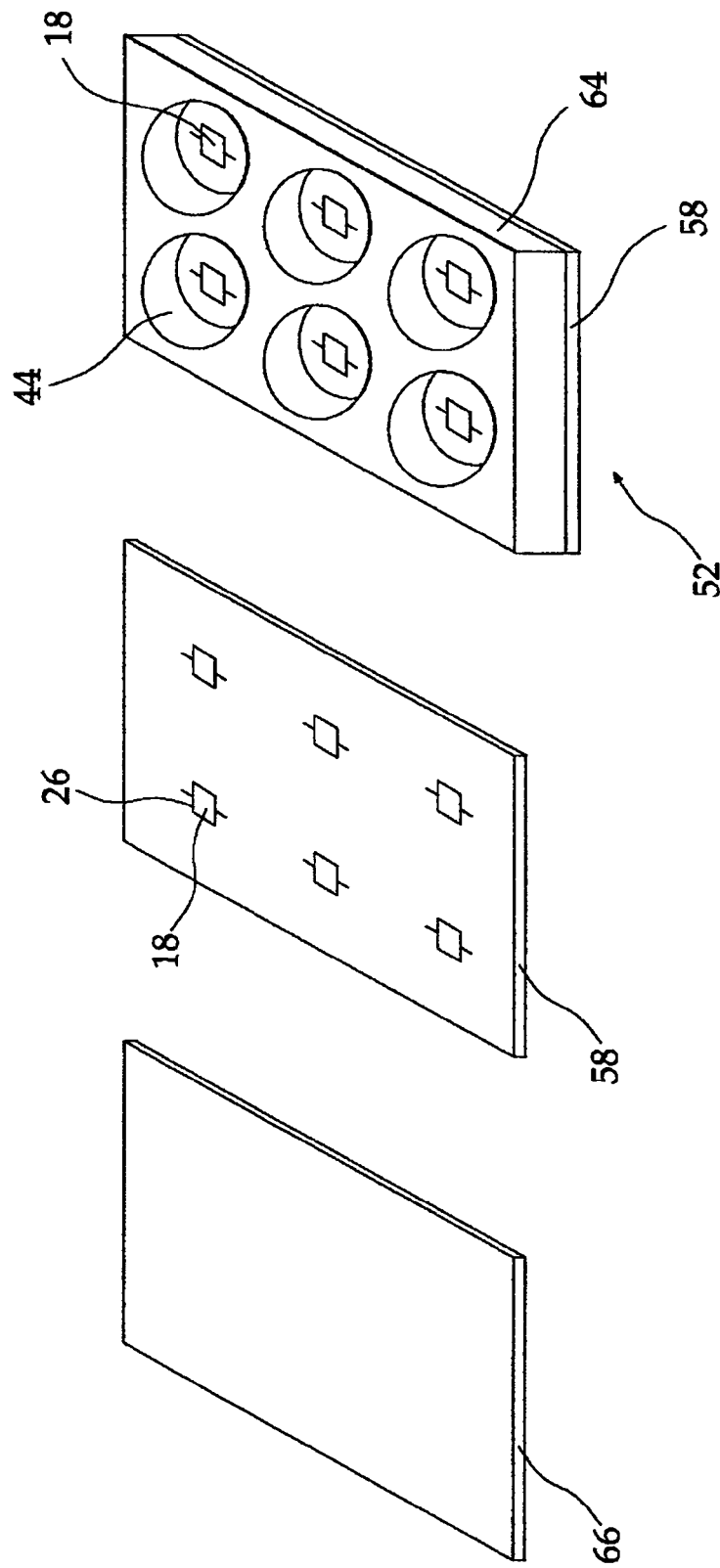

MULTIWELL PLATE

RELATED APPLICATIONS

This application is a National Phase Application of PCT Application No. PCT/IL2004/000661 having International Filing Date of Jul. 20, 2004, which claims the benefit of priority from U.S. Provisional Patent Application No. 60/488,408, filed on Jul. 21, 2003, U.S. Provisional Patent Application No. 60/488,409, filed on Jul. 21, 2003, U.S. Provisional Patent Application No. 60/517,073, filed on Nov. 5, 2003, U.S. Provisional Patent Application No. 60/517,084, filed on Nov. 5, 2003, U.S. Provisional Patent Application No. 60/544,356, filed on Feb. 17, 2004, U.S. Provisional Patent Application No. 60/544,357 filed on Feb. 17, 2004, and is also a Continuation-In-Part (CIP) of PCT Application No. PCT/IL2004/000571, filed on Jun. 27, 2004.

This application is also a Continuation-In-Part (CIP) of U.S. application Ser. No. 10/561,839, filed on Jun. 5, 2006, now abandoned, which is a National Phase of PCT Patent Application No. PCT/IL2004/000571, filed on Jun. 27, 2004, which claims the benefit of priority from U.S. Provisional Patent Application No. 60/482,437, filed on Jun. 26, 2003, U.S. Provisional Patent Application No. 60/488,408, filed on Jul. 21, 2003, U.S. Provisional Patent Application No. 60/517,073, filed on Nov. 5, 2003, U.S. Provisional Patent Application No. 60/517,084, filed on Nov. 5, 2003, U.S. Provisional Patent Application No. 60/544,356, filed on Feb. 17, 2004, and U.S. Provisional Patent Application No. 60/544,357, filed on Feb. 17, 2004.

FIELD AND BACKGROUND OF THE INVENTION

The present invention relates to the field of cellular biology and more particularly, to an improved device and method for the study of cells. Specifically, the present invention is of an improved multiwell plate and methods for making the same that allows the use of automatised sample handling methods for the study of single living cells. Further, the present invention is of a device substantially being an ordered array of living cells.

Combinatorial methods in chemistry, cellular biology and biochemistry are essential for the near simultaneous preparation of multitudes of active entities such as molecules. Once such a multitude of molecules is prepared, it is necessary to study the effect of each one of the active entities on a living organism.

The study of the effects of stimuli, such as exposure to active entities, on living organisms is preferably initially performed on living cells. Since, cell-functions include many interrelated pathways, cycles and chemical reactions, the study of an aggregate of cells, whether a homogenous or a heterogeneous aggregate, does not provide sufficiently detailed or interpretable results: rather a comprehensive study of the biological activity of an active entity may be advantageously performed by examining the effect of the active entity on a single isolated living cells. Thus, the use of single-cell assays is one of the most important tools for understanding biological systems and the influence thereupon of various stimuli such as exposure to active entities.

The combinatorial preparation of a multitudes of active entities coupled with the necessity of studying the effect of each one of the active entities on living organisms using a single-cell assay, requires the development of high-throughput single live cell assays.

In the art, various different methods for studying living cells are known.

Multiwell plates having 6, 12, 48, 96, 384 or even 1536 wells on a standard ca. 8.5 cm by ca. 12.5 cm footprint are well known in the art. Such multiwell plates are provided with an 2n by 3n array of rectangular packed wells, n being an integer. The diameter of the wells of a plate depends on the number of wells and is generally greater than about 250 microns (for a 1536 well plate). The volume of the wells depends on the number of wells and the depth thereof but generally is greater than $5 \times 10^{-6}$ liter (for a 1536 well plate).

Multiwell plates are commercially available from many different suppliers. Multiwell plates made from many different materials are available, including but not limited to glass, plastics, quartz and silicon. Multiwell plates having wells where the inside surface is coated with various materials, such as active entities, are known.

The standardization of the formats of multiwell plates is a great advantage for researchers as the standardization allows the production of standardized products including robotic handling devices, automated sample handlers, sample dispensers, plate readers, observation devices, plate washers, software and such accessories as multifilters.

Although exceptionally useful for the study of large groups of cells, multiwell plates are not suitable for the study of individual cells or even small groups of cells due to the large, relative to the cellular scale, size of the wells. Cells held in such wells either float about a solution or adhere to a well surface. When cells float about in a well, specific individual cells are not easily found for observation. When cells adhere to a well surface, the cells adhere to any location in the well, including anywhere on the bottom of the well and on the walls of the well. Such variability in location makes high-throughput imaging (for example for morphological studies) challenging as acquiring an individual cell and focusing thereon is extremely difficult. Such variability in location also makes high-throughput signal processing (for example, detection of light emitted by a single cell through fluorescent processes) challenging as light must be gathered from the entire area of the well, decreasing the signal to noise ratio. Further, a cell held in a well of a multiwell plate well can be physically or chemically manipulated (for example, isolation or movement of a single selected cell or single type of cell, changing media or introducing drugs) only with difficulty. Further, the density of cells held singly in the wells of a multiwell plate is very low (about 1536 cells in 65 cm$^2$, or 24 cells cm$^{-2}$) Thus, multiwell plates are in general only suitable for the study of homogenous or heterogenous aggregates of cells as a group.

An additional disadvantage of multiwell plates is during the study of cells undergoing apoptosis. One method of studying cells is by exposing cells in a monolayer of cells adhered to the bottom of the well of a multiwell plate to a stimulus. As is known to one skilled in the art, one of the most important processes that a cell potentially undergoes is apoptosis and it is highly desirable to observe a cell throughout the apoptosis process. However, once a cell begins the apoptosis process, the adhesion of the cell to the bottom of the well is no longer sufficient: the cell detaches from the bottom and is carried away by incidental fluid currents in the well. The cell is no longer observable and its identity lost.

In the art, a number of method and devices have been developed for the study of individual cells or a small number of cells as a group. Many such methods are based on using picowell-bearing devices. A picowell-bearing device is a device for the study of cells that has at least one picowell-bearing component for study of cells. A picowell-bearing component is a component having at least one, but generally a plurality of picowells, each picowell configured to hold at least one cell. The term "picowell" is general and includes such features as dimples, depressions, tubes and enclosures. Since cells range in size from about 1 microns to about 100 (or even more) microns diameter there is no single picowell size that is appropriate for holding a single cell of any type. That said, the dimensions of the typical individual picowell in the picowell-bearing components known in the art have dimensions of between about 1 microns up to about 200 microns, depending on the exact implementation. For example, a device designed for the study of single isolated 20 micron cells typically has picowells of dimensions of about 20 microns. In other cases, larger picowells are used to study the interactions of a few cells held together in one picowell. For example, a 200 micron picowell is recognized as being useful for the study of the interactions of two or three cells, see PCT patent application IL01/00992 published as WO 03/035824.

One feature that increases the utility of a picowell-bearing device is that each individual picowell is individually addressable. By individual addressability is meant that each picowell can be registered, found or studied without continuous observation. For example, while cells are held in picowells of a picowell-bearing component, each cell is characterized and the respective picowell where each cell is held is noted. When desired, the observation component of the picowell-bearing device is directed to the location of the picowell where a specific cell is held. One method of implementing individual addressability is by the use of fiducial points or other features (such as signs or labels), generally on the picowell-bearing component. Another method of implementing individual addressability is by arranging the picowells in a picowell-array and finding a specific desired picowell by counting. Another method of implementing individual addressability is by providing a dedicated observation component for each picowell.

In the art, the picowell-bearing component of picowell-bearing devices is often a chip, a plate or other substantially planar component. Herein such a component is termed a "carrier". In the art, there also exist non-carrier picowell-bearing components of picowell-bearing devices, for example, bundles of fibers or bundles of tubes.

Mrksich and Whitesides, *Ann. Rev. Biophys. Biomol. Struct.* 1996, 25, 55-78; Craighead et al., *J. Vac. Sci. Technol.* 1982, 20, 316; Singhvi et al., *Science* 1994, 264, 696-698; Aplin and Hughes, *Analyt. Biochem.* 1981, 113, 144-148 and U.S. Pat. No. 5,324,591 all teach of devices including arrays of spots of cell-attracting or cell-binding entities on a plate. In such devices, the spots serve as picowells, binding to cells through a variety of chemical bonds. In such devices, the plate is the picowell-bearing component of the device. Due to the size of the spots, each such picowell generally holds more than one cell. To reduce interaction between cells held at different picowells, the spots must be spaced relatively far apart, reducing loading as expressed in terms of picowells per unit area. Even with generous spacing, in such picowell-bearing components held cells are not entirely isolated from mutual interaction, nor can cells be subject to individual manipulation. The fact that the cells are not free-floating but are bound to the plate through some interaction necessarily compromises the results of experiments performed.

In U.S. Pat. No. 6,103,479, the picowell-bearing component is a transparent carrier provided with a non-uniform array of picowells, each well functionalized with chemical entities that bind to cells specifically or non-specifically. Each picowell is of approximately 200 to 1000 micron diameter and is configured to hold a plurality of cells. The inter picowell areas are hydrophobic so as not to attract cells. In addition to the carrier, a device of U.S. Pat. No. 6,103,479 is provided with a glass, plastic or silicon chamber-bearing plate in which individually addressable microfluidic channels are etched that mates with the carrier. When brought together, the carrier and chamber-bearing plate constitute a cassette in which each cell is bound to the carrier and isolated in a chamber provided with an individual fluid delivery system. Reagents are provided through the fluid delivery system and observed by the detection of fluorescence. In order to provide space for the walls of the chambers, the inter picowell areas of the carrier are relatively large, reducing loading as expressed in terms of picowells per unit area. Subsequent to study, the cassette is separated into the two parts and the micro-patterned array of cells processed further. In some embodiments, the chamber-bearing plate is made of polytetrafluoroethylene, polydimethylsiloxane or an elastomer. As held cells do not make contact with the chamber-bearing plate it is not clear what advantages are to be had when providing a chamber-bearing plate of such esoteric materials.

In U.S. Pat. No. 4,729,949, a device is taught for trapping individual cells in a picowell-bearing carrier, the carrier being substantially a plate having a plurality of picowells that are individually-addressable tapered apertures of a size to hold individual cells. Suction applied from the bottom surface of the plate where the picowells are narrow creates a force that draws cells suspended in a fluid above the carrier into the wide end of the picowells on the surface of the carrier to be held therein. Using the teachings of U.S. Pat. No. 4,729,949 a specific group of cells (having dimensions similar to that of the wide end of the picowells) can be selected from amongst a group of cells and held in the carrier. Although the cells are subjected to common stimuli, the fact that the picowells are individually addressable allows the effect of a stimulus on an individual cell to be observed. A carrier of U.S. Pat. No. 4,729,949, is generally made of metal such as nickel and prepared using standard photoresist and electroplating techniques. In a carrier of U.S. Pat. No. 4,729,949, the inter picowell areas of the carrier are relatively large, leading to a low loading as expressed in terms of picowells per unit area. Further, the suction required to hold cells in picowells of a carrier of U.S. Pat. No. 4,729,949 deforms held cells and makes a significant portion of the cell membranes unavailable for contact, both factors that potentially compromise experimental results. Study of cells with non-fluorescence based methods generally gives poor results due to reflections of light from the carrier.

In PCT patent application US99/04473 published as WO 99/45357 is taught a picowell-bearing device produced by etching the ends of a bundle of optical fibers (apparently of glass) while leaving the cladding intact to form a picowell-bearing component that is a bundle of tubes. The size of the hexagonal picowells is demonstrated to be as small as 7 micron wide, 5 micron deep and having a volume of $1.45 \times 10^{-13}$ liter. The inter picowell area is quite large due to the thickness of the cladding of the optical fibers. Cells held in each picowell are independently observable through a respective optical fiber. In some embodiments, the inside surface of the picowells is coated with a film of materials such as collagen, fibronectin, polylysine, polyethylene glycol, polystyrene, fluorophores, chromophores, dyes or a metal. Loading the picowell-bearing component of PCT patent application US99/04473 includes dipping the optical fiber bundle in a cell suspension so that cells adhere to the picowells. There are a number of disadvantages to the teachings of PCT patent application US99/04473. The fact that the cells are studied only subsequent to adhesion to the picowells necessarily influences the results of experiments performed. Since cell proliferation generally begins soon after adhesion, it is never clear if a signal detected results from a single cell or a plurality of cells. It is not clear where exactly in a picowell a cell is held and therefore what percentage of light emitted from a cell travels to a detector. The fact that emitted light travels through an optical fiber leads to loss of time-dependent and phase information.

In unpublished copending PCT patent application IL04/00192 of the Applicant filed 27 Jun. 2004 is taught a picowell-bearing device produced by bundling together glass capillaries, each glass capillary attached to an independent fluid flow generator such as a pump. A cell held in a first picowell is transferred to a second picowell by the simultaneous application of an outwards flow from the first picowell and an inwards flow into the second picowell.

A preferred device for the study of cells is described in PCT patent application IL10/00992 published as WO 03/035824. The device 10, depicted in FIG. 1, is provided with a transparent carrier 12 as a picowell-bearing component. Carrier 12 is substantially a sheet of transparent material (such as glass or polystyrene) on the surface of which features such as inlet connectors 14, fluid channels 16, picowells (in FIG. 1a well-array 18), a fluid reservoir 20 and an outlet connector 22. Carrier 12 is immovably held in a holder 24 having a cutout window of a size and shape to accept carrier 12. Other components of device 10 not depicted include flow generators, observation components, external tubing and the like. When a cover slip (not depicted) is placed or integrally formed with carrier 12, fluid channels 16, picowell-array 18 and reservoir 20 are sealed forming channels that allow transport of fluids and reagents to cells held in picowell-array 18. The picowells are configured to hold a predetermined number of cells (one or more) of a certain size and are preferably individually addressable both for examination and manipulation.

FIG. 2 is a reproduction of a photograph of a different carrier 26 held in a holder 24. A first syringe 28 as an inlet flow generator is in communication with an inlet connector 14 by a capillary tube 30. Inlet connector 14 is in communication with picowell-array 18 through a fluid passage 16. Picowell-array 18 is in communication with outlet connector 22 through a fluid passage 16. A second syringe 32 as an outlet flow generator is in communication with outlet connector 22 through capillary tube 34.

PCT patent application IL01/00992 also teaches methods of physically manipulating cells held in a picowell-bearing device using, for example, individually addressable microelectrodes (found in the picowells or in the cover slip) or optical tweezers. Typical physical manipulations include moving cells into or out of picowells. One useful method that is implemented using a device of PCT patent application IL01/00992 is that cells, each held alone in a respective picowell, are examined (either in the presence or absence of reagents) and based on the results of the examination, cells with a certain characteristic are selected to remain in a respective picowell while cells without the certain characteristic are removed from a respective picowell and ejected by the application of a flow in parallel to the surface of the carrier, generated by a flow generator.

An additional feature of the teachings of PCT patent application IL01/00992 is that, in some embodiments, the picowells are juxtaposed, that is, the area occupied by a picowell-array is substantially entirely made up of picowells with little or no inter picowell area, see FIG. 3. FIG. 3 is a reproduction of a photograph of part of a picowell-array 18 from the top of a carrier 12 of PCT patent application IL01/00992. In FIG. 3 is seen a plurality of hexagonal picowells 36, some populated with living cells 38. It is seen that the inter picowell areas 40 make up only a minor percentage of the total area of picowell-array 18. This feature allows near tissue-density packing of cells, especially in single-cell picowell configurations. For example, a typical device of PCT patent application IL01/00992 having a 2 mm by 2 mm picowell-array of hexagonally-packed juxtaposed picowells of 10 micron diameter and no inter picowell area includes about 61600 picowells. This feature also allows simple picowell loading: a fluid containing suspended cells is introduced in the volume above the picowells. Since there is little inter picowell area, cells settle in the picowells.

Despite the utility of the device taught in PCT patent applications IL01/00992, the use of the device is too labor intensive for certain high-throughput implementations. Amongst other reasons the large amount of labor is required because there exist no commercially available robotic systems optimized for use with the devices.

It would be highly advantageous to have a device for the study of cells not having at least some of the disadvantages of the prior art.

SUMMARY OF THE INVENTION

The present invention successfully addresses at least some of the shortcomings of the prior art by providing an improved multiwell plate and a new device, a method for producing the improved multiwell plate and the new device and new methods for handling living cells.

According to the teachings of the present invention there is provided a multiwell plate comprising a plurality of wells wherein at the bottom surface of at least one well of the plurality of wells is a plurality of picowells. Preferably, a plate of the present invention has a footprint of a standard multiwell plate. Preferably, the plurality of wells of a plate of the present invention comprises 6n wells arranged in a 2n by 3n array, where n is an integer greater than 0, the wells preferably being arranged in rectangular packing. Preferred pluralities of wells are the commonly known pluralities of well such as 6, 24, 96, 384 and 1536 wells. Most preferred are plates of 96 wells and 384 wells as these formats are most popular and have many available accessories including fluid-handling accessories such as fluid-handling robots.

In an embodiment of the present invention, the plurality of picowells comprises individually addressable picowells. In an embodiment of the present invention, the bottoms of all picowells in a given well of a plate of the present invention are substantially coplanar. In an embodiment of the present invention, the bottoms of all picowells of a plate of the present invention are substantially coplanar.

In an embodiment of the present invention, the picowells of a plurality of picowells in a given well are juxtaposed. By juxtaposed is meant that in an area where picowells are found, most of the area is picowell area and little of the area is inter picowell area. According to a feature of the present invention, by juxtaposed is meant that the inter picowell area between two picowells is less than or equal to 0.35, 0.25, 0.15, 0.10 or even 0.06 of the sum of the areas of the two picowells. In certain embodiments of the present invention it is preferred that the inter picowell area be substantially zero, that is that the rims of picowells are substantially knife-edged.

The dimensions of picowells of a multiwell plate of the present invention, depending on the specific embodiment, are less than about 200 microns, less than about 100 microns, less than about 50 microns, less than about 25 microns or even less than about 10 microns. In an embodiment of the present invention, picowells are configured to hold no more than one living cell of a certain size at any one time. In an embodiment of the present invention, picowells are configured to hold no more than a predetermined number of living cells of a certain size at any one time.

In an embodiment of the present invention, the picowells are enclosures of dimensions such that substantially at least one entire cell of a certain size is containable within such an enclosure, each enclosure having an opening at the surface of the carrier, the opening defined by a first cross section of a size allowing passage of a cell of the certain size. Depending on the embodiment, the volume of such an enclosure is typically less than about $1\times10^{-11}$ liter, less than about $1\times10^{-12}$ liter, less than about $1\times10^{-13}$ liter, less than about $1\times10^{-14}$ liter or even less than about $1\times10^{-5}$ liter. Depending on the embodiment, the area of the first cross section of such an enclosure is typically less than about 40000 micron$^2$, less than about 10000 micron$^2$, less than about 2500 micron$^2$, less than about 625 micron$^2$ or even less than about 100 micron$^2$. In an embodiment of the present invention, picowells enclosures are configured to hold no more than one living cell of a certain size at any one time. In an embodiment of the present invention, picowells enclosures are configured to hold no more than a predetermined number of living cells of a certain size at any one time.

In an embodiment of the present invention, the plurality of picowells comprises picowells, wherein all picowells of the plate are substantially identical in size.

In another embodiment of the present invention, a first well of a plate of the present invention includes a first plurality of picowells and a second well of a plate includes a second plurality of picowells, wherein the first plurality of picowells and the second plurality of picowells are substantially different. For example, in an embodiment of the present invention the size of the picowells of the first plurality is substantially different from the size of picowells of the second plurality of picowells.

A multiwell plate of the present invention is made of any suitable material. Suitable materials include but are not limited to ceramics, elastomers, epoxies, glasses, glass-ceramics, metals, plastics, polycarbonates, polydimethylsiloxane, polyurethane, polyethylenterephtalate glycol, polymers, polymethyl methacrylate, polystyrene, polyvinyl chloride, rubber, silicon, silicon oxide and silicon rubber.

In an embodiment of the present invention, the bottom surface of the wells is made of any suitable material. Suitable materials include but are not limited to ceramics, elastomers, epoxies, glasses, glass-ceramics, metals, plastics, polycarbonates, polydimethylsiloxane, polyethylenterephtalate glycol, polymers, polymethyl methacrylate, polystyrene, polyurethane, polyvinyl chloride, rubber, silicon, silicon oxide and silicon rubber.

In embodiments of the present invention, an entire plate of the present invention and all components thereof are made of one material. In other embodiments, a plate of the present invention is made up of a number of different materials, for example, as a plurality of layers or as a coated structure.

In an embodiment of the present invention, the walls of wells of the plurality of wells are integrally formed with the bottom surface of the wells.

In other embodiments, a plate of the present invention comprises at least one distinct well-wall component attached to the bottom surface. Such a distinct well-wall component is made of any suitable material. Suitable materials include but are not limited to ceramics, elastomers, epoxies, glasses, glass-ceramics, metals, plastics, polycarbonates, polydimethylsiloxane, polyethylenerephtalate glycol, polymers, polyurethane, polymethyl methacrylate, polystyrene, polyvinyl chloride, rubber, silicon, silicon oxide and silicon rubber.

In an embodiment of the present invention, a plurality of picowells are integrally formed with the bottom surface.

In an embodiment of the present invention, a plate of the present invention comprises at least one distinct picowell-bearing component bearing a plurality of picowells, the component attached to the bottom surface of a respective well or simply resting within a respective well.

A suitable distinct picowell-bearing component is a carrier comprising a plurality of picowells disposed on a surface, such as a carrier described in PCT patent application IL01/00992 or in unpublished copending PCT patent application IL04/00571 of the Applicant filed 27 Jun. 2004 (vide infra). Picowell-bearing components are made of any suitable material, including reversibly deformable materials and irreversibly deformable materials. Suitable materials include but are not limited to gels, hydrogels, waxes, hydrocarbon waxes, crystalline waxes, paraffins, ceramics, elastomers, epoxies, glasses, glass-ceramics, metals, plastics, polycarbonates, polydimethylsiloxane, polyethylenterephtalate glycol, polymers, polymethyl methacrylate, polystyrene, polyurethane, polyvinyl chloride, rubber, silicon, silicon oxide and silicon rubber.

In an embodiment of the multiwell plate of the present invention, the picowell-bearing component comprises a gel, preferably a transparent gel, preferably a hydrogel.

Gels suitable for use in making a picowell-bearing component of a plate of the present invention include but are not limited to agar gels, agarose gels, gelatins, low melting temperature agarose gels, alginate gels, room-temperature $Ca^{2+}$-induced alginate gels and polysaccharide gels. Depending on the embodiment, a suitable gel has a water content of greater than about 80% by weight, greater than about 92% by weight, greater than about 95% by weight, greater than about 97% by weight and even greater than about 98% by weight. In an embodiment of the present invention, the gel includes an active entity. Suitable active entities include, but are not limited to antibodies, antigens, biological materials, chemical materials, chromatogenic compounds, drugs, enzymes, fluorescent probes, immunogenes, indicators, ligands, nucleic acids, nutrients, peptides, physiological media, proteins, receptors, selective toxins and toxins.

In an embodiment of the present invention, picowells have a bottom surface made of a first material and borders, such as the borders delineating the picowells, made of a second material, the second material being substantially different from the first material. In an embodiment of the present invention the first material is substantially the material from which the bottom of the well is made, for example when the bottom surface of the picowell is substantially the bottom surface of the well. In an embodiment of the present invention, the second material is a fixed photoresist material.

In an embodiment of the plate of the present invention, the plurality of picowells comprises picowells having an inside surface configured to delay proliferation of cells held therein, for example, by delaying adhesion of living cells thereto. In an embodiment of the plate of the present invention, the inside of a picowell comprises a material that delays adhesion of living cells thereto, that is the picowell is substantially fashioned from the adhesion-delaying material or the inside of the picowell is coated with the adhesion-delaying material. A suitable material to coat the inside of a picowell or from which to make a picowell comprises polydimethylsiloxane, is substantially polydimethylsiloxane or is substantially pure polydimethylsiloxane.

In an embodiment of the present invention bottom surfaces of picowells making up a plurality of picowells of a plate comprise a material having an index of refraction similar to that of water. In a preferred embodiment of a plate of the present invention, the index of refraction of the bottom surfaces is less than about 1.4, less than about 1.38, less than about 1.36, less than about 1.35, less than about 1.34 or substantially equal to that of water.

In an embodiment of the present invention, the plurality of picowells comprises picowells having an inner surface coated with a layer of a material. Suitable materials for coating an inner surface of a picowell of a plate of the present invention include but are not limited to gels, hydrogels, polydimethylsiloxane, elastomers, polymerized para-xylylene molecules, polymerized derivatives of para-xylylene molecules, rubber and silicon rubber.

In an embodiment of the present invention, a plate of the present invention further comprises a gel cover covering a plurality of the picowells, the cover made of a gel. Suitable gels are as described hereinabove.

In an embodiment of the present invention, substantially the entire bottom surface of a well is covered by a respective plurality of picowells.

In an embodiment of the present invention, a plate further comprises at least one additional feature functionally associated with the plurality of picowells, especially microfluidic features. Suitable microfluidic features include but are not limited to channels, coupling elements, drains, fluid channels, fluid reservoirs, input ports, membranes, microreactors, microvalves, output ports, passages, plumbing routes, protruberances, pumps, transport channels and valves. Other suitable features include but are not limited to light sources, magnetizable elements, optical components, optical fibers, optical filters, protuberances, fiducial points and walls.

In an embodiment of the present invention, a plate further comprises a cover slip, the cover slip and a plurality of picowells in a well configured so as to allow the cover slip to rest above the plurality of picowells substantially in parallel to the bottom surface of the well.

According to the teachings of the present invention, there is provided a method of making a multiwell plate of the present invention, comprising: (a) contacting a precursor material with a template including a negative of features of the plate so as to create the features in the precursor material, the features including the plurality of picowells; (b) fixing the features in the precursor material so as to fashion an incipient plate; and (c) processing the incipient plate so as to fashion the multiwell plate of the present invention.

Depending on the embodiment and the nature of the precursor material, fixing includes such methods a heating the precursor material, cooling the precursor material, polymerizing the precursor material, cross-linking the precursor material, curing the precursor material, irradiating the precursor material, illuminating the precursor material, gelling the precursor material, exposing the precursor material to a fixative and waiting a period of time.

The template is generally made of a material that is rigid compared to the precursor material. Suitable materials include but are not limited to reversibly deformable materials, irreversibly deformable materials, ceramics, epoxies, glasses, glass-ceramics, metals, plastics, polycarbonates, polydimethylsiloxane, polyethylenterephtalate glycol, polymers, polymethyl methacrylate, paraffins, polystyrene, polyurethanes, polyvinyl chloride, silicon, silicon oxide, silicon rubbers and wax.

Features created in the precursor material in addition to the plurality of picowells include such features as channels, coupling elements, drains, fluid channels, fluid reservoirs, input ports, light sources, magnetizable elements, membranes, microreactors, microvalves, passages, optical components, optical fibers, optical filters, output ports, plumbing routes, protruberances, pumps, transport channels, valves, walls and fiducial points. In an embodiment of the present invention, the features created in the precursor material in addition to the plurality of picowells include the plurality of wells.

In an embodiment of the present invention, prior to contacting the template with the precursor material, the precursor material is placed in a well of a preexisting multiwell plate.

In an embodiment of the present invention, subsequent to the fixing of the features, walls of the plurality of wells are attached to the incipient plate. Attaching includes the use of methods employing adhesives or surface treatments such as plasma treatments.

In an embodiment of the present invention the precursor material is an irreversibly deformable material (vide infra) such as a wax, a paraffin, plastic or polymer, and fixing the features simply includes separating the template from the precursor material.

In an embodiment of the present invention the precursor material is a reversibly deformable material (vide infra) such as a gellable fluid, a polymerizable material, a powder, a fluid or a thermoplastic material.

In an embodiment of the present invention, the reversibly deformable precursor material is a thermoplastic material at plastic temperature and fixing the features includes cooling the thermoplastic material.

In an embodiment of the present invention, the reversibly deformable precursor material is a polymerizable material and fixing the features includes polymerizing the polymerizable material. Suitable polymerizable materials include but are not limited to monomer solutions, crosslinkable polymers, vulcanizable polymers, polymerizable fluid and thermosetting resins.

In a preferred embodiment, the polymerizable material is a polydimethylsiloxane precursor mixture and fixing the features includes polymerizing the polydimethylsiloxane precursor mixture so as to produce polydimethylsiloxane. In another preferred embodiment, the polymerizable material includes urethane and fixing the features includes polymerizing the urethane to produce polyurethane.

In an embodiment of the present invention, the reversibly deformable precursor material is a gellable fluid and fixing the features includes gelling the gellable fluid. Depending on the nature of the gellable fluid used, preferred methods of gelling the gellable fluid include of heating the gellable fluid, cooling the gellable fluid, irradiating the gellable fluid, illuminating the gellable fluid, contacting the gellable fluid with a gelling reagent and waiting a period of time for the gellable fluid to gel. Suitable gellable fluids include but are not limited to agars, agaroses, gelatins, low melting temperature agaroses, alginates, proteins, protein polysaccharides, room-temperature $Ca^{2+}$-inducable alginates and polysaccharides. A preferred gellable fluid is an alginate solution where gelling the gellable fluid includes contacting the gellable fluid with a gelling reagent, such as a gelling reagent including $Ca^{2+}$ ions. An additional preferred gellable fluid is a low melting temperature agarose solution and gelling the gellable fluid includes cooling the gellable fluid.

In an embodiment of the present invention, processing the incipient plate comprises coating an inside surface of picowells of the plurality of picowells with a layer of a coating material.

According to the teachings of the present invention there is provided an additional method of making a multiwell plate of the present invention, comprising (a) placing a photoresist material on a precursor plate; and (b) fixing a plurality of picowells in the photoresist material. Preferably, the fixing of the plurality of picowells comprises irradiating the photoresist material through a mask. A precursor plate is made of a suitable material. Suitable materials include but are not limited to ceramics, epoxies, glasses, glass-ceramics, metals, plastics, polycarbonates, polydimethylsiloxane, polymers, polyethylenterephtalate glycol, polymethyl methacrylate, polystyrene, polyurethanes, polyvinyl chloride, silicon and silicon oxide.

In an embodiment of the method of the present invention the precursor plate comprises a multiwell plate. The photoresist material is placed in a well of the precursor plate and the photoresist material irradiated inside the well.

In an embodiment of the present invention, subsequent to the fixing of the features, walls of the plurality of wells are attached to the precursor plate. Attaching includes the use of methods employing adhesives or surface treatments such as plasma treatments.

In an embodiment of the present invention, subsequent to fixing the picowells in the photoresist material, the inside surface of picowell of the plurality of picowells is coated with a layer of a coating material.

According to the teachings of the present invention, there is provided an additional method for making a multiwell plate of the present invention by placing a picowell-bearing component on a precursor plate. In a preferred embodiment, the picowell-bearing component is attached to the precursor plate. Attaching includes the use of methods employing adhesives or surface treatments such as plasma treatments. A suitable picowell-bearing component includes a carrier comprising a plurality of picowells disposed on a surface, such as a carrier described in PCT patent application IL01/00992 or in unpublished copending PCT patent application IL04/00571 of the Applicant filed 27 Jun. 2004 (vide infra).

In an embodiment of the method of the present invention the precursor plate comprises a multiwell plate and the picowell-bearing component is placed in a respective well.

In an embodiment of the present invention, subsequent to the placing of the picowells-bearing component on the precursor plate, walls of the plurality of wells are attached to the precursor plate. Attaching includes the use of methods employing adhesives or surface treatments such as plasma treatments.

In an embodiment of the present invention, subsequent to placing the picowells on the precursor plate, the inside surface of picowells of the plurality of picowells are coated with a layer of a coating material.

As noted above, whatever method is used for making a multiwell plate of the present invention, it is often desired to coat the plurality of picowells, especially the inside surface of picowells with some material. Coating the inside surface of a picowell allows modification of the properties of the picowell, for example to reduce cytotoxicity, to change physical properties such as solvent resistance or permeability or to delay proliferation of cells held in a respective picowell. In an embodiment of the method of the present invention, coating the inside surface of picowells comprises (i) applying a precursor fluid to inside surfaces of the picowells; and (ii) solidifying the precursor fluid so as to form the layer. Suitable methods of solidifying include but are not limited to heating the precursor fluid, cooling the precursor fluid, polymerizing the precursor fluid, cross-linking the precursor fluid, curing the precursor fluid, irradiating the precursor fluid, illuminating the precursor fluid, gelling the precursor fluid, exposing the precursor fluid to a fixative and waiting a period of time.

In another embodiment of the method of the present invention, coating the inside of the wells comprises (i) depositing a vapor of the coating material onto the inside surface of the picowells thereby forming the layer of coating material.

In another embodiment of the present invention, coating the inside surface of the wells comprises (i) depositing a vapor of a coating precursor material onto the inside surface of the picowells; and (ii) solidifying the coating precursor material thereby forming the layer of the coating material. Suitable methods of solidifying the coating precursor material depend on the details of the specific embodiment and include but are not limited to heating the coating precursor material, cooling the coating precursor material, polymerizing the coating precursor material, cross-linking the coating precursor material, curing the coating precursor material, irradiating the coating precursor material, illuminating the coating precursor material, gelling the coating precursor material, exposing the coating precursor material to a fixative and waiting a period of time. In a preferred embodiment, the vapor of coating precursor material is a vapor of para-xylylene molecules or derivatives thereof and the layer comprises the polymerized para-xylylene molecules (or derivatives thereof). By para-xylylene derivatives is meant a a molecule that is substantially a para-xylylene molecules having any additional substituent on either or both aromatic rings.

According to the teachings of the present invention there is also provided a device comprising an array of living cells held in a non-fluid matrix, where the matrix is configured to maintain cell viability. Preferably, the living cells are physically held in pockets in the matrix and there is substantially no bond between the living cells and the matrix. In a preferred embodiment, the array is substantially planar having an upper surface and a lower surface. In a preferred embodiment, one or both of the two surfaces is transparent to at least one wavelength of light or range of wavelengths of light in the ultraviolet, visible or infrared light spectrum.

In a preferred embodiment of the present invention, the matrix is configured to substantially delay the proliferation of living cells held therein.

In an embodiment of the device of the present invention the matrix comprises a material having an index of refraction similar to that of water. In a preferred embodiment of the device present invention, the index of refraction of the matrix is less than about 1.4, less than about 1.38, less than about 1.36, less than about 1.35, less than about 1.34 or substantially equal to that of water.

One material from which a matrix is preferably made that generally has at least some of the preferred properties described above is a gel, especially a hydrogel. Suitable gels are as described above for gel picowells of a multiwell plate of the present invention.

In a preferred embodiment of the present invention, the matrix further comprises an active entity. A preferred active entity is an indicator, especially an indicator configured to indicate a cell response to a stimulus, such as the release of a second active entity.

According to the teachings of the present invention there is also provided a method for handling living cells, comprising: (a) providing an ordered array of living cells immobilized in a non-fluid matrix, the matrix configured to maintain cell viability; (b) contacting the living cells with a stimulus; and (c) detecting a response of the cells to the stimulus. The method of handling living cells of the present invention is preferably implemented using the device of the present invention.

In an embodiment of the present invention, the matrix further comprises an active entity. A preferred active entity is an indicator, especially an indicator configured to indicate a cell response to a stimulus, such as the release of a second active entity.

In an embodiment of the present invention, part of the detecting a response comprises contacting the matrix with an active entity. A preferred active entity is an indicator, especially an indicator configured to indicate a cell response to a stimulus, such as the release of a second active entity. In some embodiments, it is required to wait a period of time so as to allow the contacted active entity to reach proximity with the cells, for example by diffusion through the matrix.

In an embodiment of the present invention, detecting comprises detecting emitted light, for example light emitted by a cell or from an indicator, for example by fluorescence. In an embodiment of the present invention, detecting comprises detecting light, for example light reflected, diffracted, passing through or passing by a cell or an indicator.

According to the teachings of the present invention there is provided a method for producing an ordered array of living cells in a non-fluid matrix, comprising: (a) providing a multiwell plate provided with a plurality of wells, the multiwell plate including a plurality of picowells at the bottom of at least one well, the plurality of picowells including picowells; (b) placing a suspension of a plurality of living cells in a gellable fluid in the at least one well; (c) causing the living cells to settle into the picowells so as to be held in respective picowells; and (d) gelling the gellable fluid so as to make a gel cover, trapping the living cells between the picowells and the gel cover. In an embodiment of the present invention, the picowells are made of a material comprising a gel.

Generally, causing the living cells to settle into the picowells includes applying a force to the cells, typical forces including gravitation, centrifugal forces, forces resulting from the impact of photons on the cells (e.g., laser tweezers, application of a non-focussed laser (see, for example, P.A.L.M. Microlaser Technologies AG, Bernried, Germany)), or forces resulting from a pressure wave (such as produced by an ultrasonic transponder).

In a preferred embodiment, prior to gelling the gellable fluid, it is ensured that each picowell holds no more than one living cell. In another preferred embodiment, prior to gelling the gellable fluid, it is ensured that each picowell holds no more than a predetermined number of living cell or holds a predetermined number of living cells.

In a preferred embodiment, the gellable fluid is chosen so that upon gelling a transparent gel is formed. In a preferred embodiment, the gellable fluid is chosen so that upon gelling a hydrogel is formed.

Depending on the nature of the gellable fluid used, preferred methods of gelling the gellable fluid include of heating the gellable fluid, cooling the gellable fluid, irradiating the gellable fluid, illuminating the gellable fluid, contacting the gellable fluid with a gelling reagent and waiting a period of time for the gellable fluid to gel. Gellable fluids suitable for use in in implementing the method of the present invention include but are not limited to agar gel solutions, agarose gel solutions, gelatin solutions, low melting temperature agarose gel solutions, alginate gel solutions, room-temperature $Ca^{2+}$-induced alginate gel solutions and polysaccharide gel solutions. Depending on the embodiment, a gellable fluid has a water content of greater than about 80% by weight, greater than about 92% by weight, greater than about 95% by weight, greater than about 97% by weight and even greater than about 98% by weight. A preferred gellable fluid is an alginate solution where gelling the gellable fluid includes contacting the gellable fluid with a gelling reagent, such as a gelling reagent including $Ca^{2+}$ ions. An additional preferred gellable fluid is a low melting temperature agarose solution and gelling the gellable fluid includes cooling the gellable fluid. In an embodiment of the present invention, the gellable fluid further comprises an active entity. A preferred active entity is an indicator, especially an indicator configured to indicate a cell response to a stimulus, such as the release of a second active entity.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 11A-11E are schematic depictions of steps of a method of the present invention for making a multiwell plate of the present invention by contacting a template bearing negatives of pluralities of picowells with a reversibly deformable precursor material followed by attachment of a separate well-wall component;

FIGS. 13A-13C are schematic depictions of steps of a method of the present invention for making a multiwell plate of the present invention by producing pluralities of picowells by photolithography inside wells of a preexisting multiwell plate;

FIGS. 14A-14C are schematic depictions of steps of a method of the present invention for making a multiwell plate of the present invention by attaching preexisting picowell-bearing carriers inside wells of a preexisting multiwell plate;

FIGS. 15A-15C are schematic depictions of steps of a method of the present invention for making a multiwell plate of the present invention by attaching preexisting picowell-bearing carriers to a substantially flat precursor plate followed by attachment of a separate well-wall component;

DETAILED DESCRIPTION OF THE INVENTION

Figure 1:
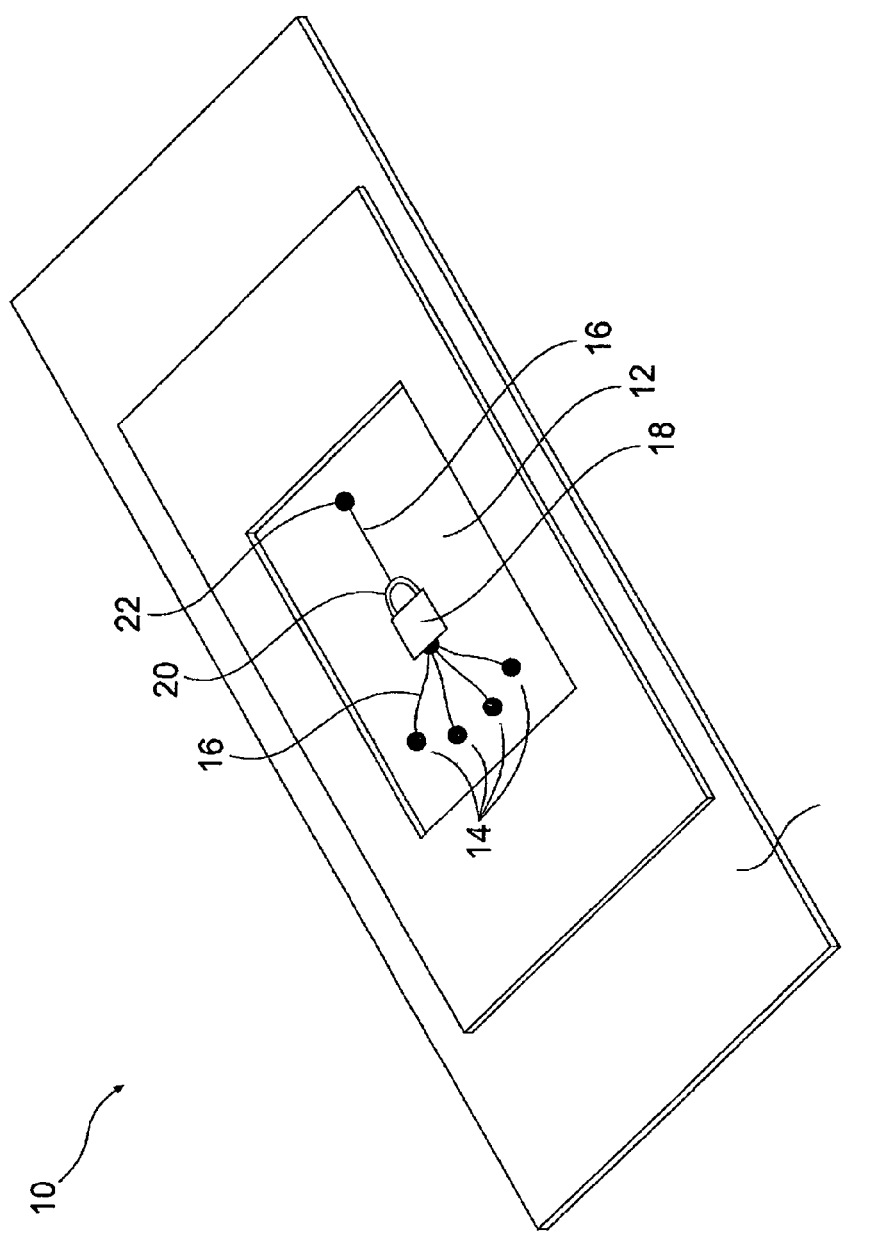
FIG. 1 (prior art) depicts a cell-chip device of PCT patent application IL01/00992 including a transparent carrier.

The present invention is of a mulitwell plate having a plurality of picowells on the bottom of the wells of the plate. The present invention is also of methods of producing a mulitwell plate of the present invention. The present invention is also of a device comprising an array of living cells held in a non-fluid matrix. The present invention is also of a method of handling living cells by providing an ordered array of living cells immobilized in a non-fluid matrix, contacting the living cells with a stimulus; and detecting a response to the stimulus. The present invention is also of a method of producing an ordered array of living cells.

The principles and uses of the teachings of the present invention may be better understood with reference to the accompanying description, figures and examples. In the figures, like reference numerals refer to like parts throughout.

Before explaining at least one embodiment of the invention in detail, it is to be understood that the invention is not limited in its application to the details set forth herein. The invention can be implemented with other embodiments and can be practiced or carried out in various ways. It is also understood that the phraseology and terminology employed herein is for descriptive purpose and should not be regarded as limiting.

Generally, the nomenclature used herein and the laboratory procedures utilized in the present invention include techniques from the fields of biology, chemistry and engineering. Such techniques are thoroughly explained in the literature. Unless otherwise defined, all technical and scientific terms used herein have the same meaning as commonly understood by one of ordinary skill in the art to which the invention belongs. In addition, the descriptions, materials, methods, and examples are illustrative only and not intended to be limiting. Methods and materials similar or equivalent to those described herein can be used in the practice or testing of the present invention. All publications, patent applications, patents and other references mentioned are incorporated by reference in their entirety as if fully set forth herein. In case of conflict, the specification herein, including definitions, will control.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Implementation of the methods of the present invention involves performing or completing selected tasks or steps manually, automatically, or a combination thereof.

Herein, the term "active entity" is understood to include chemical, biological or pharmaceutical entities including any natural or synthetic chemical or biological substance that influences a cell with which the entity is in contact. Typical active entities include but are not limited to active pharmaceutical ingredients, antibodies, antigens, biological materials, chemical materials, chromatogenic compounds, drugs, enzymes, fluorescent probes, immunogenes, indicators, ligands, nucleic acids, nutrients, peptides, physiological media, proteins, receptors, selective toxins and toxins.

Herein, by "indicator" is meant any active entity that upon interaction with some stimulus produces an observable effect. In the context of the present invention, by stimulus is meant, for example, a specific second active entity (such as a molecule) released by a cell and by observable effect is meant, for example, a visible effect, for example a change in color or emission of light.

Some embodiments of the present invention include components that are transparent or are made of a transparent material. By "transparent" is meant that the component or material is substantially transparent to radiation having a wavelength in at least part of the visible light spectrum, the ultraviolet light spectrum and/or of infrared radiation, preferably the visible light spectrum.

It is important to note that some embodiments of the present invention are related to embodiments of unpublished copending PCT patent application IL04/00571 of the Applicant filed 27 Jun. 2004. In IL04/00571 are taught picowell-bearing carriers having a variety of innovative features. One aspect of the teachings of PCT patent application IL04/00571 is of picowells configured to influence cell proliferation of cells held therein. In one embodiment, carriers having picowells of a changeable size is taught. In another embodiment, carriers configured to delay proliferation of cells held therein, for example by delaying or preventing cell adhesion, are taught. In another embodiment, carriers configured so as to allow cells to grow into or through the carrier are taught. The above-described embodiments are preferably implemented by making the picowells of or coating the picowells with a material with the desired properties. In some embodiments, the inner surface of a picowell with which a held cell makes contact is configured to have the desired property, influence or effect. Preferred materials from which to make carriers listed in PCT patent application IL04/00571 include polydimethylsiloxane, elastomers (such as silicon rubber), polymerized para-xylylene molecules, polymerized derivatives of para-xylylene molecules and gels (especially hydrogels). In some embodiments, the inner surface of a picowell with which a held cell makes contact is configured to have the desired property, influence or effect.

An additional aspect of PCT patent application IL04/00571 are the teachings of a gel cover for picowell bearing components. The gel cover is configured to prevent cells held in a picowell from exiting the picowell due to jostling, incidental fluid flows or during movement of the carrier.

The advantages of a picowell-bearing carrier made of a gel, of a picowell gel-cover or a gel carrier covered with a gel cover include, depending on the embodiment, that active entities may be integrated into the gel, that active entities may be contacted with the cell by diffusion through the gel, that diffusion of released compounds is slowed down allowing identification of which cell released a given compound, that proliferation of cells held therein is delayed but once cells begin to proliferate, that allows proliferation into and through the gel matrix.

Figure 4:
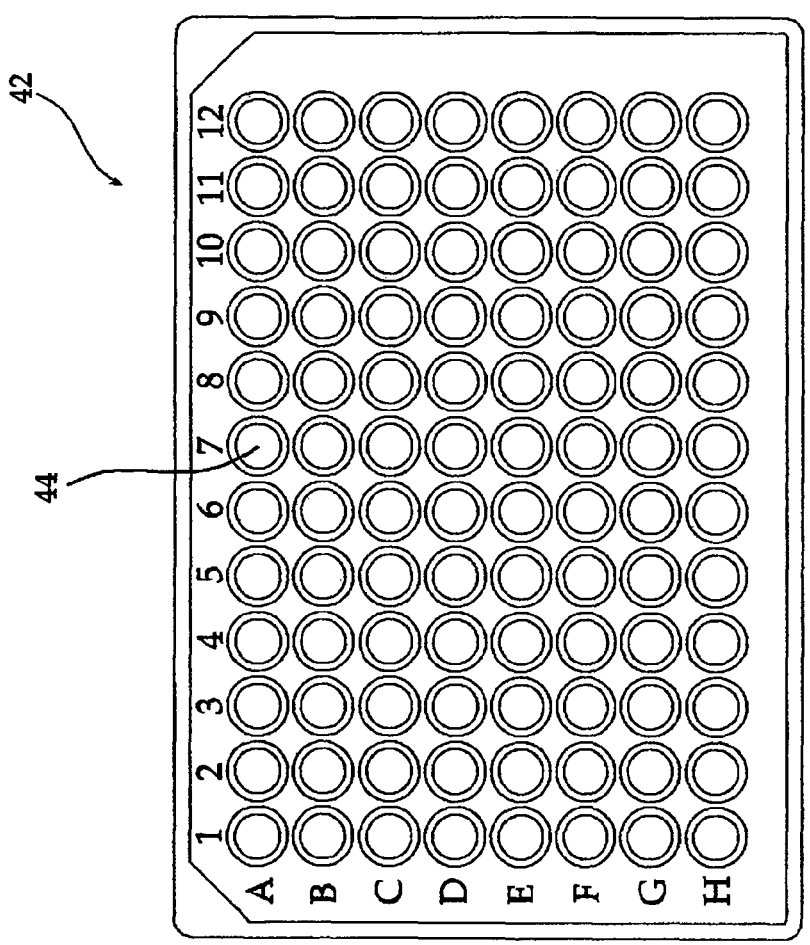
FIG. 4 (prior art) is a schematic depiction of a standard commercially available 96-well plate.

As discussed hereinabove, a prior art multiwell plate is substantially a planar device having an upper surface whereupon is found an array of wells configured to hold a fluid containing cells or other entities. As noted above, multiwell plates generally have a standard footprint of ca. 8.5 cm by ca. 12.5 cm. As noted above, the wells of a prior art multiwell plate are generally distributed in a standard 2n by 3n rectangular packed well-array, n being an integer. The standard multiwell plates have 6, 12, 48, 96, 384 or even 1536 standard sized wells. The volume of the wells depends on the number of wells and the depth thereof but is generally greater than $5 \times 10^{-6}$ liter (for a 1536 well plate). In FIG. 4 is depicted a top view of a prior art 96-well plate 42 from the top, comprising 96 wells 44 arranged in a 8 by 12 array.

Figure 5A:
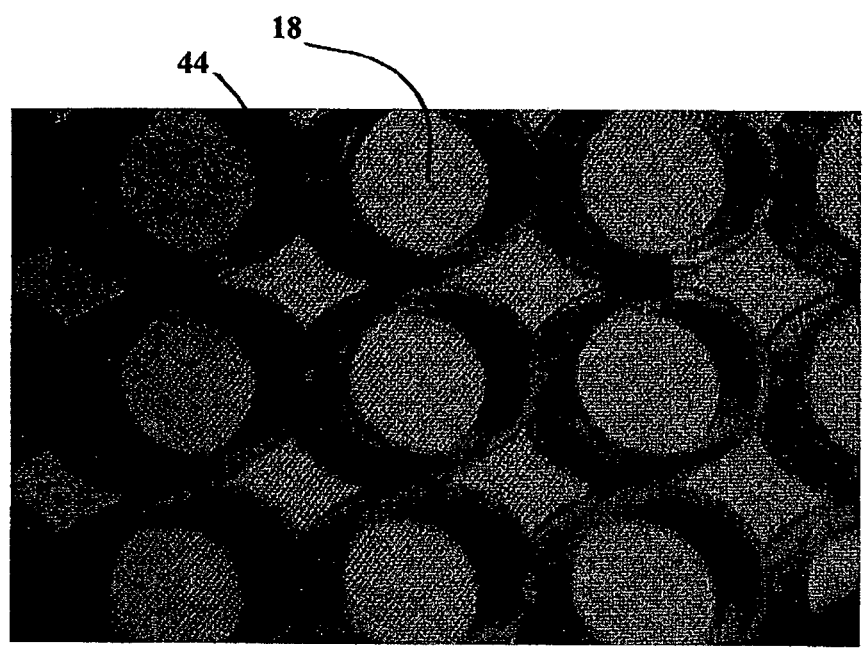
FIGS. 5A-5B are reproduction of photographs of a 96-well plate of the present invention showing wells and picowells.
Figure 5B:
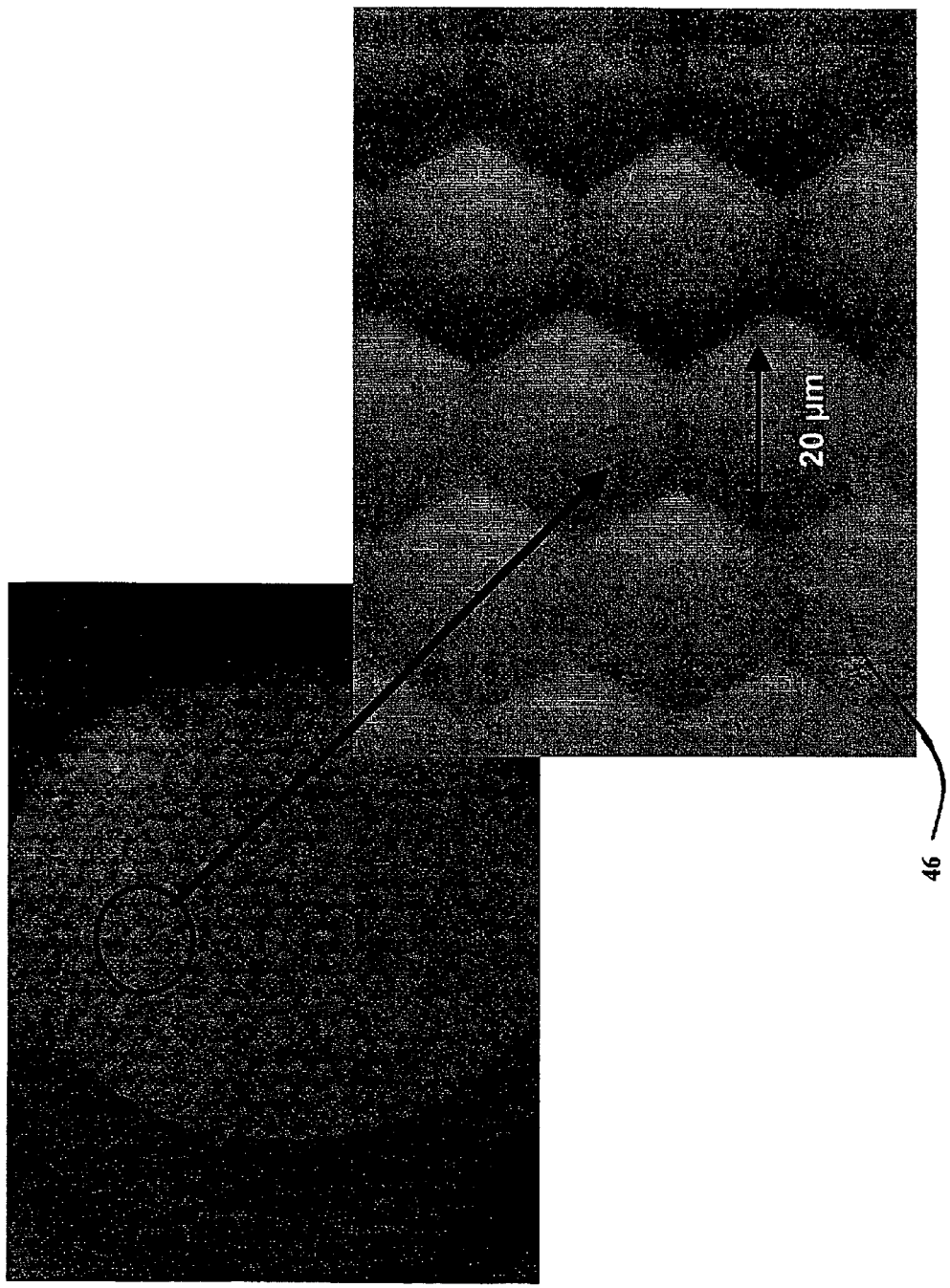

The present invention provides an improved multiwell plate where at the bottom surface of at least one of the wells (preferably substantially all of the wells) are a plurality of picowells. FIG. 5 are top views of a multiwell plate of the present invention. With no magnification, a plate of the present invention looks like prior art plate 42 depicted in FIG. 4. Magnification of a single well 44 of the 96 wells reveals that at the bottom of a well 44 is found an array 18 of hexagonally packed 20 micron hexagonal picowells 46, FIGS. 5A and 5B. In one embodiment, substantially the entire bottom surface of such a well comprises picowells (as depicted in FIG. 5A). In one embodiment of the multiwell plate of the present invention, the picowell-containing wells are homogenous, that is all have substantially the same size and arrangement of picowells (as depicted in FIG. 5A). In another embodiment of the multiwell plate of the present invention, the picowell-containing wells are heterogenous, that is there is variation between wells, for example variation in the size of the picowells, the arrangement of the picowells or the material from which the picowells are made or with which the picowells are coated.

The present invention also provides methods of making multiwell plates of the present invention. According to one embodiment of the method of the present invention, a preexisting multiwell plates is converted into a multiwell plates of the present invention. According to another embodiment of the method of the present invention, a multiwell plates of the present invention is fashioned in one piece, the wells and the picowells being integrally formed components of the multiwell plate. According to another embodiment of the method of the present invention, a multiwell plates of the present invention is fashioned by attaching a component or a plurality of components that is substantially the walls defining the wells to a second component, where the second component is substantially a plate bearing the picowells of the multiwell plate.

Multiwell Plate of the Present Invention

As stated hereinabove, a multiwell plate of the present invention is substantially a multiwell plate having a plurality of wells wherein at the bottom surface of at least one well of the plate is found a plurality of picowells. Preferably, such a plate has a footprint of a standard multiwell plate. Preferably, the wells of the plurality of wells of such a plate are arranged in a manner similar or substantially identical to the arrangement of wells of a standard multiwell plate, that is, a rectangular packing of 6n wells arranged in a 2n by 3n array, where n is an integer greater than 0. Preferred are the most common multiwell plate formats, that is, 6, 24, 96, 384 and 1536 wells, 96-wells and 384-wells being most preferred. Preferably, the individual picowells of the plurality of picowells are individually addressable. For ease of optical study and observation, it is preferred that the bottoms of all the picowells of a certain well or of the entire plate be substantially coplanar: coplanarity allows for optical observation of many cells (whether by scanning or simultaneously using a wide-angle observation component) without the need for time consuming and technically difficult to implement refocusing.

The use of a multiwell plate of the present invention allows efficient study of pluralities of living cells as individuals.

On the one hand, standard accessories available in the art for manipulating and using multiwell plates including robotic plate handlers, robotic fluid dispensers, multipipettes, multifilters and the like are useable with the multiwell plates of the present invention. Further, the format of the wells of prior art multiwell plates has proven to be convenient for the performance of many simultaneous experiments in the field of cellular biology, for example, during combinatorial studies.

On the other hand, cells placed in a well of a multiwell plate of the present invention are held in the picowells of a respective plurality of picowells. The effect is that a plurality of cells held in a multiwell plate of the present invention are arranged in a rationally ordered array. The rational arrangement of cells eases observation (especially when the bottoms of the picowells are coplanar) and makes the cells more easily observable as individuals (especially when the picowells are individually addressable). Held cells are isolated from direct physical contact with other cells, improving the quality of experimental results.

Figure 6:
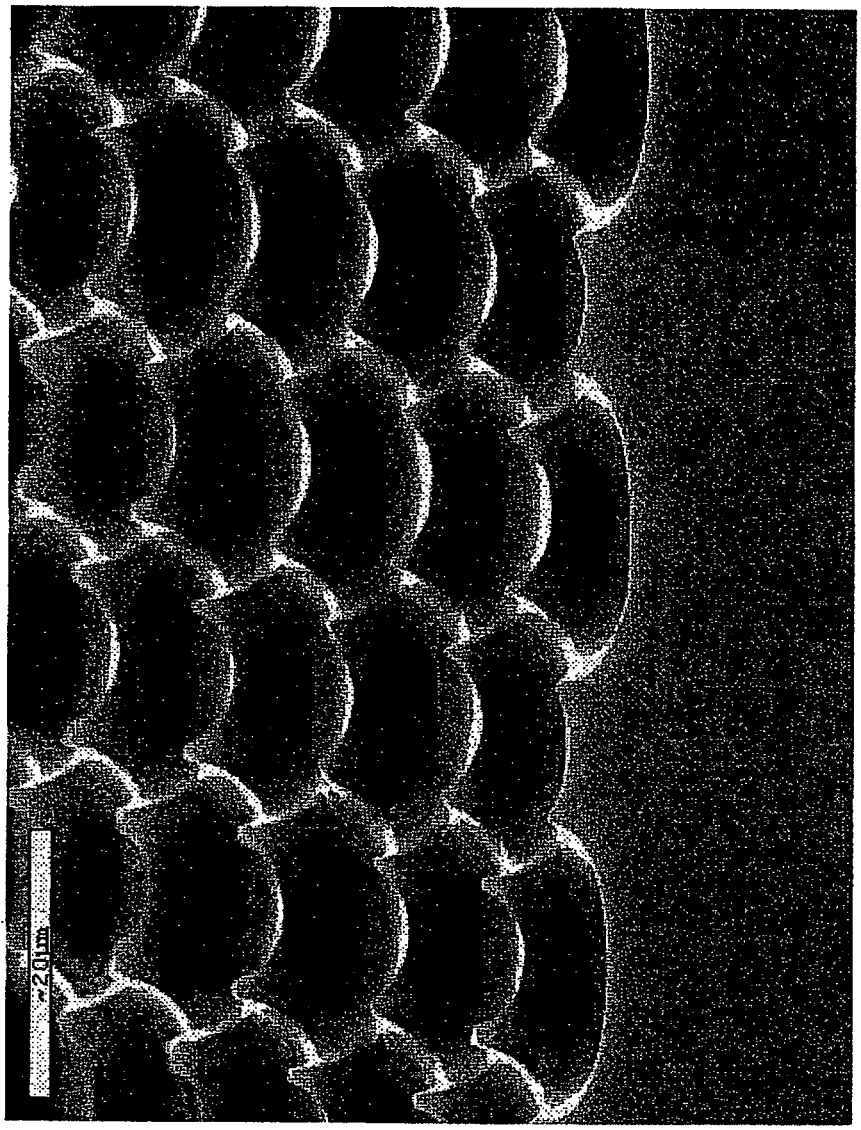
FIG. 6 is a reproduction of a scanning electron micrograph of an array of picowells of a multiwell plate of the present invention.

In an embodiment of the present invention, the picowells of the plurality of picowells of a well are juxtaposed. By juxtaposed is meant that in an area where picowells are found, most of the area is picowell area and little of the area is inter picowell area. For example, in embodiments of the present invention, the inter picowell area between two picowells is less than or equal to 0.35, 0.25, 0.15, 0.10 or even 0.06 of the sum of the areas of the two picowells. In a preferred embodiment, the inter picowell area is substantially nonexistent, for example when the rims of picowells are substantially knife-edged. A picowell-array having substantially no inter picowell area is seen in FIG. 5B. In FIG. 6, a reproduction of a scanning electron micrograph of a picowell-array of a multiwell plate of the present invention having knife-edged rims is shown. One advantage of juxtaposed picowells is that when cells are placed in a respective well, the cells settle into picowells and do not settle onto inter picowell areas.

Further, when a plurality of juxtaposed picowells is used, a near-tissue density planar array of cells is achieved. For example, an array of 10-micron wide hexagonal packed knife-edged picowells has a picowell density of about $1.5 \times 10^{6}$ picowells $cm^{-1}$.

Further, for reasons of a simple loading procedure and a high picowell density, in a preferred embodiment of the present invention, a plurality of picowells covers substantially the entire bottom surface of a respective well, as depicted in FIG. 5.

As the teachings of the present invention are directed to cellular biology, it is generally preferred that the picowells be small so as to avoid having a large number of cells held in any one picowell. Thus, generally, the dimensions of the picowells are generally less than about 200, 100, 50, 25 or even 10 microns. By dimensions is meant the usual meaning of the word and is dependent on the shape of the picowell. For example, for hexagonal or circular picowells, the term dimension refers to diameter. For square or triangular picowells is meant the longest dimension of the square or triangle, respectively. The exact dimensions of individual picowells depends on the type (and consequently size) of cells to be studied and the types of experiments and studies that are to be performed. Since different types of cells have different sizes, generally a multiwell plate of the present invention has picowells of a size to accommodate one or more cells of the type to be studied. In some embodiments it is preferred that an individual picowell be of a size so as to hold no more than one living cell of a certain size. In other embodiments it is preferred that the picowell be of a size so as to held no more than a predetermined number of cells of a certain size (e.g., two or three cells simultaneously).

Figure 7:
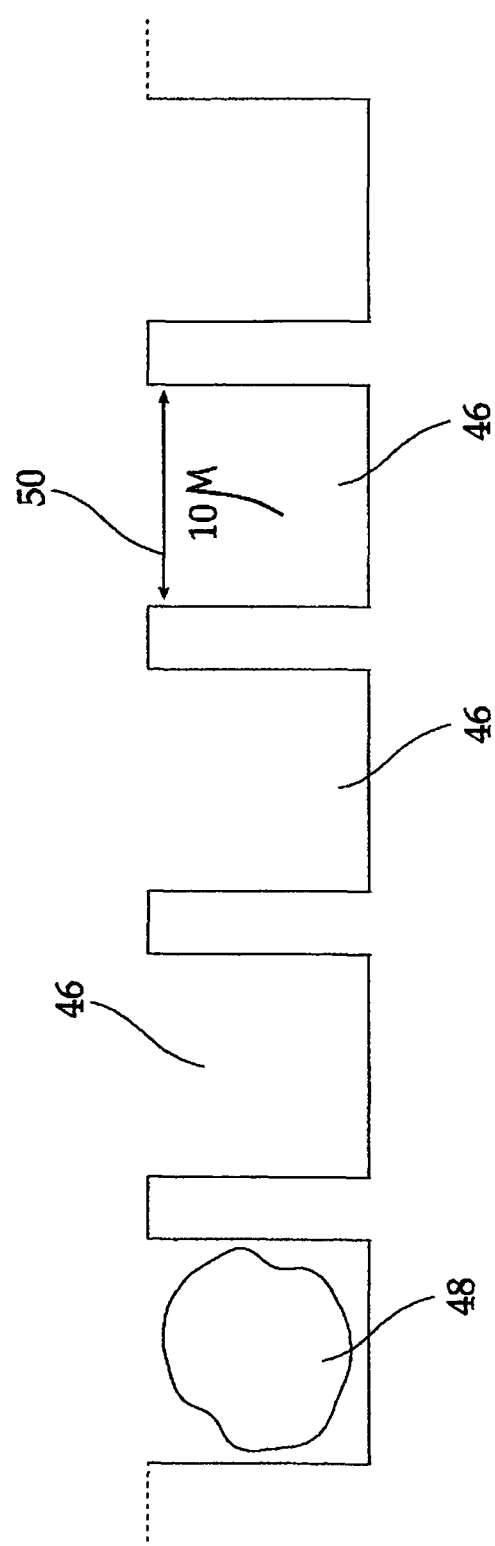
FIG. 7 is a schematic depiction of a side view of picowells of the present invention configured as enclosures.

In some embodiments of the present invention, picowells are dimples or depressions on the bottom surface of the inside of a well of a multiwell plate, as seen in FIG. 6. In other embodiments, depicted in side view in FIG. 7, picowells 46 are substantially enclosures of dimensions so that at least one cell 48 of a certain size is containable, substantially entirely, within the enclosure, each enclosure having an opening 50 at the surface, the opening defined by a first cross section of a size allowing passage of cell of the certain size 48. The exact dimensions of the individual enclosures depends on the type (and consequently size) of cells to be studied and the types of experiments and studies that are to be performed. The volume of such enclosure picowells is typically less than $1 \times 10^{-11}$ liter (corresponding to the volume of a 200 micron cube), less than $1 \times 10^{-12}$ liter (corresponding to the volume of a 100 micron cube), less than $1 \times 10^{-13}$ liter (corresponding to the volume of a 50 micron cube), less than $1 \times 10^{-14}$ liter (corresponding to the volume of a 25 micron cube) and even less than $1 \times 10^{-15}$ liter (corresponding to the volume of a 10 micron cube). The area of the first cross section, corresponding to the size of the opening of a respective enclosure is typically less than about 40000 micron$^2$ (corresponding to the area of a 200 micron square), 10000 micron$^2$ (corresponding to the area of a 100 micron square), 2500 micron$^2$ (corresponding to the area of a 50 micron square), 625 micron$^2$ (corresponding to the area of a 25 micron square) or even less than about 100 micron$^2$ (corresponding to the area of a 10 micron square).

In embodiments of the present invention, all the picowells of all the pluralities of picowells in all the wells of the multiwell plate of the present invention are substantially identical in size. In embodiments of the present invention, the plurality of picowells in one well is substantially different from the plurality of picowells in a second well. For example, in an embodiment of the present invention the size of the picowells of the plurality of picowells in one well is different from the size of the picowells of the plurality of picowells in a second well. In embodiments of the present invention, the plurality of picowells in one well includes picowells of different sizes or shapes. For example, in an embodiment of the present invention, one well includes 10 micron picowells together with 20 micron micron picowells.

A multiwell plate of the present invention is made of any suitable material. Suitable materials include but are not limited to ceramics, elastomers, epoxies, glasses, glass-ceramics, metals, plastics, polycarbonates, polydimethylsiloxane, polyurethane, polyethylenterephtalate glycol, polymers, polymethyl methacrylate, polystyrene, polyvinyl chloride, rubber, silicon, silicon oxide and silicon rubber. In an embodiment of the present invention, the bottom surface of the wells is made of any suitable material. Suitable materials include but are not limited to ceramics, elastomers, epoxies, glasses, glass-ceramics, metals, polymers, plastics, polycarbonates, polydimethylsiloxane, polyethylenterephtalate glycol, polymethyl methacrylate, polystyrene, polyurethane, polyvinyl chloride, rubber, silicon, silicon oxide and silicon rubber.

In embodiments of the present invention, an entire plate of the present invention and all components thereof are made of one material. In other embodiments, a plate of the present invention is made up of a number of different materials, for example, as a plurality of layers or as a coated structure.

In an embodiment of the present invention, the walls of wells are integrally formed with the bottom surface of the wells. In embodiments, a multiwell plate of the present invention comprises at least one distinct well-wall component attached to the bottom surface. Such a distinct well-wall component is made of any suitable material. Suitable materials include but are not limited to ceramics, elastomers, epoxies, glasses, glass-ceramics, metals, plastics, polycarbonates, polydimethylsiloxane, polyethylenterephtalate glycol, polymers, polyurethane, polymethyl methacrylate, polystyrene, polyvinyl chloride, rubber, silicon, silicon oxide and silicon rubber.

In embodiments of the present invention, a plurality of picowells is integrally formed with the bottom surface of a respective well.

In embodiments of the present invention, a multiwell plate of the present invention comprises at least one distinct picowell-bearing component bearing a plurality of picowells, the component resting in or attached to the bottom surface of a respective well. A suitable distinct picowell-bearing component is a carrier comprising a plurality of picowells disposed on a surface, such as a carrier described in PCT patent application IL01/00992 or in unpublished copending PCT patent application IL04/00571 of the Applicant filed 27 Jun. 2004. Picowell-bearing components are made of any suitable material, including reversibly deformable materials and irreversibly deformable materials. Suitable materials include but are not limited to gels, hydrogels, waxes, hydrocarbon waxes, crystalline waxes, paraffins, ceramics, elastomers, epoxies, glasses, glass-ceramics, metals, plastics, polycarbonates, polydimethylsiloxane, polyethylenterephtalate glycol, polymers, polymethyl methacrylate, polystyrene, polyurethane, polyvinyl chloride, rubber, silicon, silicon oxide and silicon rubber.

In an embodiment of the multiwell plate of the present invention, a picowell-bearing component comprises a gel, preferably a transparent gel, preferably a hydrogel. Gel picowell-bearing components are discussed in detail in PCT patent application IL04/00571. As will be discussed in detail hereinfurther, in general a gel picowell-bearing component of the present invention is advantageously produced by placing a gellable fluid in a well of an existing multiwell plate, contacting the gel with a template including, amongst others, negatives of the picowells, and then gelled. Gels suitable for use in making a picowell-bearing component of a plate of the present invention include but are not limited to agar gels, agarose gels, gelatins, low melting temperature agarose gels, alginate gels, room-temperature $Ca^{2+}$-induced alginate gels and polysaccharide gels. Depending on the embodiment, a suitable gel has a water content of greater than about 80% by weight, greater than about 92% by weight, greater than about 95% by weight, greater than about 97% by weight and even greater than about 98% by weight. Two exceptionally preferred types of hydrogels are alginates and low melting temperature agaroses.

Alginates are biologically compatible polysaccharide proteins that are fluid at low calcium ion concentrations (e.g., $[Ca^{2+}]<1$ μM) but gel upon exposure to higher concentrations of calcium ions (e.g., $[Ca^{2+}]=20$ mM). An exceptionally suitable alginate for implementing the teachings of the present invention is sodium alginate and may be purchased, for example, from Pronova Biopolymers (Drammen, Norway) as Protanal LF120 1% in water or Protanal LF200 1% in water.

Low melting temperature agaroses are biologically compatible gels that before gelling are fluid at temperatures that do not harm living cells (e.g., 20° C.), gel at low temperatures that do not harm living cells (e.g., 4° C.) and remain stable until well-above temperatures used for studying living cells (40° C.). An exceptionally suitable agarose for implementing the teachings of the present invention that may be purchased, for example, from Cambrex Bio Science Rockland Inc. (Rockland, Me., USA) is HGS-LMP Agarose (catalogue nr. 50221).

In an embodiment, the gel includes an active entity. Suitable active entities include, but are not limited to antibodies, antigens, biological materials, chemical materials, chromatogenic compounds, drugs, enzymes, fluorescent probes, immunogens, indicators, ligands, nucleic acids, nutrients, peptides, physiological media, proteins, receptors, selective toxins and toxins.

In an embodiment of the present invention, picowells have a bottom surface made of a first material and borders, such as the borders delineating the picowells, made of a second material, the second material being substantially different from the first material. In an embodiment of the present invention the first material is substantially the material from which the bottom of the well is made, for example when the bottom surface of the picowell is substantially the bottom surface of the well. In an embodiment of the present invention, the second material is a fixed photoresist material. As is detailed hereinbelow, such a picowell structure is achieved by fixing a photoresist material applied to a precursor plate. An advantage of such like plates is that features such as picowells having flat bottom surfaces are easily made.

In an embodiment of the multiwell plate of the present invention, picowells are configured with an inside surface configured to delay proliferation of cells held therein, for example by delaying adhesion of living cells thereto. Picowells configured to delay proliferation of living cells held therein are discussed in detail in PCT patent application IL04/00571. In an embodiment of the plate of the present invention, the inside of a picowell comprises a material that delays adhesion of living cells thereto, that is the picowell is substantially fashioned from the adhesion-delaying material or the inside of the picowell is coated with the adhesion-delaying material. A suitable material to coat the inside of a picowell or from which to make a picowell comprises polydimethylsiloxane, is substantially polydimethylsiloxane or is substantially pure polydimethylsiloxane. Suitable polydimethylsiloxane resins for coating picowells or to make picowells are commercially available and can be purchased, amongst others, under the trade names RTV615 PDMS (GE Silicones, Wilton, Conn., USA) and Sylgard 184 PDMS (Dow Corning Corporation, Midland, Mich., USA).

In an embodiment of the multiwell plate of the present invention, bottom surfaces of the picowells comprise a material having an index of refraction similar to that of water, that is an index of refraction of less than about 1.4, less than about 1.38, less than about 1.36, less than about 1.35, less than about 1.34 or substantially equal to that of water. Picowells having indicia of refraction similar to that of water are discussed in detail in PCT patent application IL04/00571. An advantage of such picowells is that observation of cells is simplified as the picowell walls are substantially invisible and there is little, if any, scattering, reflection and diffraction of light, that otherwise interferes with optical study of held cells, for example, during morphological studies using a microscope.

In an embodiment of the present invention, the plurality of picowells comprises picowells having an inner surface coated with a layer of a material. Suitable materials for coating an inner surface of a picowell of a plate of the present invention include but are not limited to gels, hydrogels, polydimethylsiloxane, elastomers, polymerized para-xylylene molecules, polymerized derivatives of para-xylylene molecules, rubber and silicon rubber. Picowells having coated inner surfaces are discussed in detail in PCT patent application IL04/00571.

In an embodiment of the present invention, a plate of the present invention further comprises a gel cover covering a plurality of the picowells, the cover made of a gel. Suitable gels are as described herein. Gel picowell covers are discussed in detail in PCT patent application IL04/00571.

In an embodiment of the present invention, a multiwell plate of the present invention further comprises at least one additional feature functionally associated with the plurality of picowells, especially a microfluidic feature. Suitable microfluidic features include but are not limited to channels, coupling elements, drains, fluid channels, fluid reservoirs, input ports, membranes, microreactors, microvalves, output ports, passages, plumbing routes, protruberances, pumps, transport channels and valves. Other suitable features include but are not limited to light sources, magnetizable elements, optical components, optical fibers, optical filters, protuberances, fiducial points and walls. Such an embodiment can be considered to be a multiwell plate of the present invention that holds a carriers such as described in PCT patent application IL01/00992 or in unpublished copending PCT patent application IL04/00571. Such an embodiment allows performance of many and varied experiments to study living cells, as described in the above references.

In an embodiment of the of the present invention, a multiwell plate further comprises a cover slip, the cover slip and a plurality of picowells in a well configured so as to allow the cover slip to rest above the plurality of picowells substantially in parallel to the bottom surface of the respective well. Such a cover slip can include microelectrodes to assist in manipulation of cells held in picowells, can be used in conjunction with other features so as to provide a microfluidics system for the picowells, or for other reasons as discussed in PCT patent application IL01/00992.

Methods of Manufacture of a Multiwell Plate of the Present Invention

A multiwell plate of the present invention is produced using any suitable method known in the art. Suitable methods include methods that employ one or more techniques including but not limited to casting, embossing, etching, free-form manufacture, injection-molding, microetching, micromachining, microplating, molding, spin coating, lithography or photo-lithography.

The preferred methods of producing a multiwell plate of the present invention are the methods of the present invention.

A first method of the present invention for making a multiwell plate of the present invention is substantially by contacting a precursor material with a template, the template having a negative of some of the features of the plate (especially the picowells) thus creating the features in the precursor material. The features are subsequently fixed in the precursor material making an incipient plate. After any further processing of the incipient plate required (which may be limited to simply separating the template from the incipient plate), the multiwell plate of the present invention is fashioned.

Depending on the precursor material, fixing includes, but is not limited to, methods such as heating the precursor material, cooling the precursor material, curing the precursor material, polymerizing the precursor material, cross-linking the precursor material, irradiating the precursor material, illuminating the precursor material, gelling the precursor material, exposing the precursor material to a fixative and waiting a period of time. By fixative is meant an agent that causes the precursor material to change to the fixed state and is used herein as a general term for such materials as fixatives, hardeners, polymerization/crosslinking/curing initiators, catalysts and agents. It is important to note that in some cases a precursor material is produced by mixing two or more components which thereafter change to a fixed state, for example, by simply waiting a period of time.

In one preferred embodiment of the present invention, the precursor material is a irreversibly deformable precursor material. Herein by irreversibly deformable precursor material is meant a material that does not recover a shape after deformation and so there is usually no need for a separate action to fix the features in the precursor material beyond separating the produced multiwell plate from the template. In such cases, the precursor material does not substantially chemically change subsequent to contact with the template. Examples of suitable irreversibly deformable precursor materials include waxes, paraffins, plastics, polymers and the like. In such an embodiment, a preferred template is a stamp, and the contacting of the template with the precursor material is substantially stamping the features of the multiwell plate into the precursor material, preferably under controlled thermal conditions.

In another preferred embodiment of the present invention, the precursor material is a reversibly deformable precursor material. Herein by reversibly deformable precursor material is meant a material that is capable of recovering shape after deformation and includes gellable fluids, polymerizable materials, powders, fluids and thermoplastic materials.

In a preferred embodiment, the reversibly deformable precursor material is a thermoplastic material at a pliable temperature. Subsequent to the contacting of the template but before the contact is finished, the thermoplastic material is cooled, thus fixing the desired features in the incipient multiwell plate.

In another preferred embodiment, the reversibly deformable precursor material is a polymerizable material (e.g., a monomer solution, a crosslinkable polymer, a vulcanizable polymers, a polymerizable fluids or a thermosetting resin). Subsequent to the contacting of the template but before the contact is finished, the polymerizable material is polymerized, thus fixing the desired features in the incipient multiwell plate. In such cases, the precursor material and the material from which the multiwell plate is made are chemically dissimilar (for example, have the relationship of monomer to polymer).

One preferred polymerizable precursor material is a non-cured polydimethylsiloxane precursor mixture. A mixture of two polydimethylsiloxane components (the prepolymer and curing agent) are mixed together in the desired ratio (preferably about 10:1, but ratios between about 5:1 and about 20:1 are generally suitable) to give a polydimethylsiloxane precursor mixture, the mixture degassed and contacted with the template. The features are fixed by the curing of the mixture. Curing of polydimethylsiloxane precursor generally takes place at room temperature for about 24 hours and, when desired, is accelerated by heating. For example it has been found that multiwell plates of the present invention made of polydimethylsiloxane are ready for further processing within 2 hours when cured at 60° C. or within 15 minutes when cured at 150° C. A detailed review of methods for the production of micronic features such as picowells from polydimethylsiloxane suitable for implementing the teachings of the present invention are known in the art and discussed, for example, in Ng et al., *Electrophoresis* 2002, 23, 3461-3473 and Duffy et al., *Anal. Chem.* 1998, 70, 4974-4984.

Another preferred polymerizable precursor material is urethane that is polymerized to yield polyurethane.

Another preferred reversibly deformable precursor material is a gellable fluid. After the gellable fluid is brought in contact with the template, the features are fixed by gelling the gellable fluid to yield a gel. Most preferred are gellable fluids that produce a hydrogel.

Gellable fluids known in the art include fluids that gel upon heating, fluids that gel upon cooling, fluids that gel upon irradiation or illumination, fluids that gel as a result of contact with a gelling reagent and fluids that gel after a period of time. Preferred gellable fluids for implementing the teachings of the present invention include solutions of agars, agaroses, gelatins, low melting temperature agaroses, alginates, proteins, protein polysaccharides, $Ca^{2+}$-inducable alginates (especially those that gel at room temperature) and polysaccharides.

One preferred gellable fluid is a low-melting temperature agarose solution. Such a solution is fluid at temperatures that do not harm living cells (e.g., 20° C.) and gel at low temperatures that do not harm living cells (e.g., 4° C.). An exceptionally suitable agarose for implementing the teachings of the present invention that may be purchased, for example, from Cambrex Bio Science Rockland Inc. (Rockland, Me., USA) is HGS-LMP Agarose 0.5% in PBS (catalogue nr. 50221).

Another preferred gellable fluid is an alginate solution which gels upon contact with a gelling reagent, the preferred gelling reagent being a solution having a $Ca^{2+}$ ion concentration of greater than about $1 \times 10^{-6}$ M. An exceptionally useful gelling agent is a $20 \times 10^{-3}$ M calcium gluconate solution. Suitable alginate solutions can be purchased from Pronova Biopolymers (Drammen, Norway) and include, for example, Protanal LF120 1% in water and Protanal LF200 1% in water.

The template having a negative of the features is, for example, a stamp or a mold, and is generally made of any suitable material that is more rigid than a respective precursor material. Suitable materials include but are not limited to reversibly deformable materials, irreversibly deformable materials, ceramics, epoxies, glasses, glass-ceramics, metals, plastics, polycarbonates, polydimethylsiloxane, polyethylenterephtalate glycol, polymers, polymethyl methacrylate, paraffins, polystyrene, polyurethanes, polyvinyl chloride, silicon, silicon oxide, silicon rubbers and wax.

The template is made, for example, using methods with which one skilled in the art is acquainted such as casting, embossing, etching, free-form manufacture, injection-molding, microetching, micromachining, microplating, molding, lithography or photo-lithography.

Figure 8:
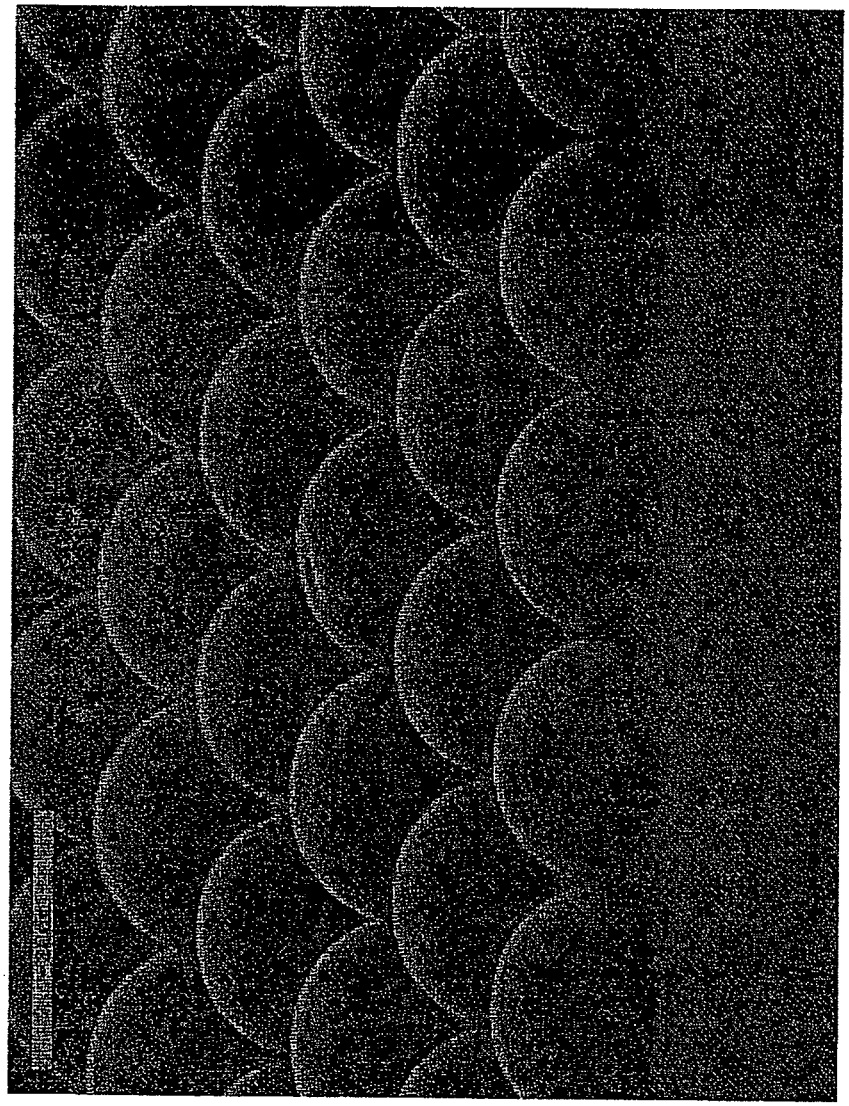
FIG. 8 is a reproduction of a scanning electron micrograph of the domes on a nickel template used for the production of a plurality of picowells of the present invention.

In FIG. 8, is shown a reproduction of a scanning electron micrograph of the domes on a nickel stamp used as a template for the production of a multiwell plate of the present invention. Seen is an array of hexagonally-packed domes that are the negative of a hexagonal array of knife-edged picowells, such as seen in FIG. 6. The diameter of the domes at the intersection with the nickel surface is approximately 20 microns.

In some embodiments, other features created in the precursor material by the contact of the template include features such as drains, channels, coupling elements, drains, fiducial points, fluid channels, fluid reservoirs, input ports, microreactors, microvalves, passages, optical components, optical filters, output ports, plumbing routes, protruberances, protruberances for supporting a cover slip, pumps, transport channels, valves, walls and partial walls.

Figure 9C:
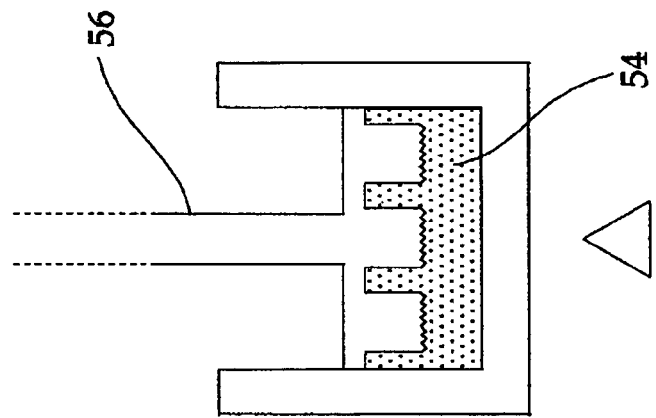
FIGS. 9A-9F are schematic depictions of steps of a method of the present invention for making a multiwell plate of the present invention by contacting a template bearing negatives of wells and a pluralities of picowells with a reversibly deformable precursor material.
Figure 9B:
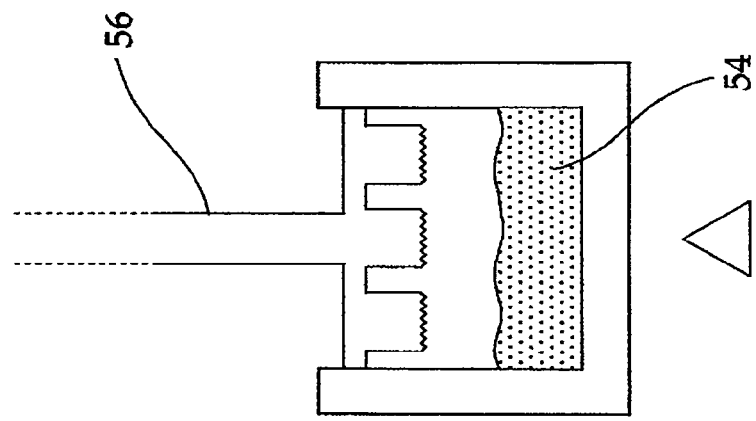
Figure 9A:
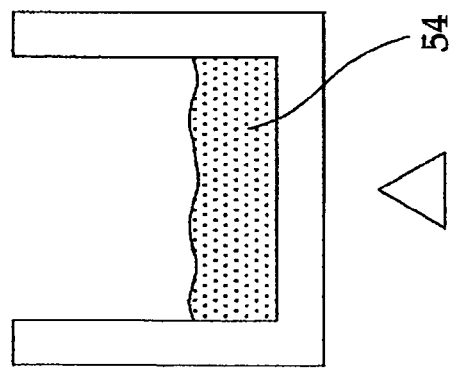
Figure 9F:
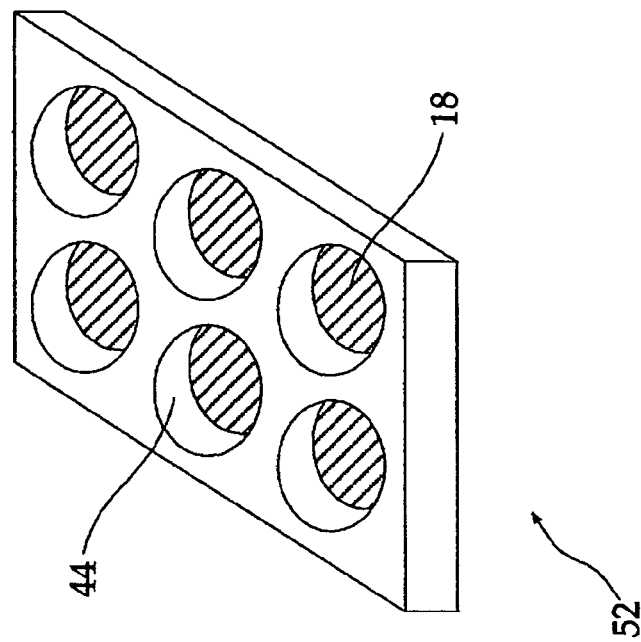
Figure 9E:
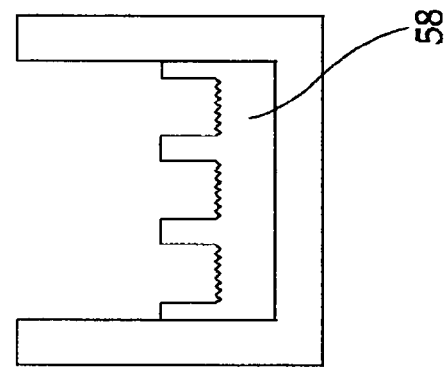
Figure 9D:
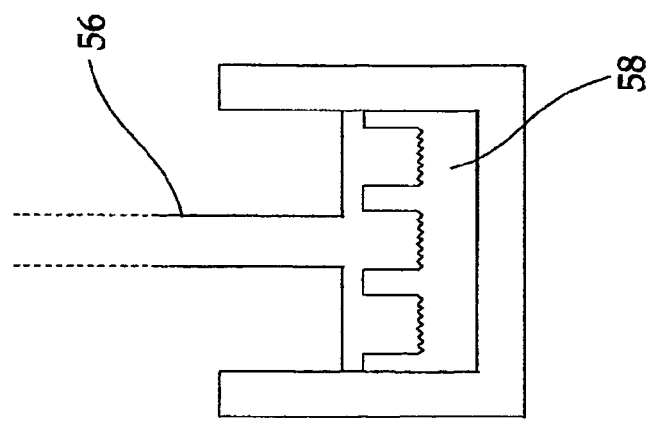

In some embodiments of the present invention, the wells of a multiwell plate of the present invention are made by contacting a precursor material with a template. Steps for producing a six-well plate of the present invention 52 according to a method of the present invention are schematically depicted in FIG. 9. In FIG. 9A, a fluid and therefore reversibly deformable precursor material 54 is provided. Precursor material 54 is a molten thermoplastic material. In FIG. 9B, a template 56 substantially a nickel stamp having features that are negatives of features of plate 52 including wells and picowells is provided. In FIG. 9C, template 56 is brought in contact with precursor material 54 so as to form the features of plate 52 in precursor material 54. In FIG. 9D, the features of plate 52 are fixed in precursor material 54 by cooling so as to make incipient plate 58. After sufficient cooling, template 56 is separated from incipient plate 58, FIG. 9E. Incipient plate 58 undergoes whatever further processing is necessary to ultimately yield plate 52 of the present invention, having pluralities of picowells 18 in each one of six wells 44, FIG. 9F.

In a preferred embodiment, a multiwell plate of the present invention is made by making picowells (and other desired features) as described above inside the wells of a preexisting multiwell plate. Suitable multiwell plates include but are not limited to plates made of reversibly deformable materials, irreversibly deformable materials, ceramics, epoxies, glasses, glass-ceramics, metals, plastics, polycarbonates, polydimethylsiloxane, polyethylenterephtalate glycol, polymers, polymethyl methacrylate, polystyrene, polyurethanes, polyvinyl chloride, silicon, silicon oxide and silicon rubbers. In such a case, the precursor material is placed into each desired well of the preexisting multiwell plate. A template is then placed inside the well so as to make contact with the precursor material and the precursor material is fixed as described above. Such an embodiment has the advantage that a commercially available multiwell plate of any format (e.g., 6, 24, 96, 384 and 1536 wells) and of virtually any material can be converted into a multiwell plate of the present invention. In such an embodiment a template can be made and used for fixing picowells and other features in any number of wells including for each well separately or for all wells simultaneously. In this way, a single multiwell plate of the present invention having different features (e.g., different sized picowells) in different wells is easily made.

Figures 10A, 10B, 10C:
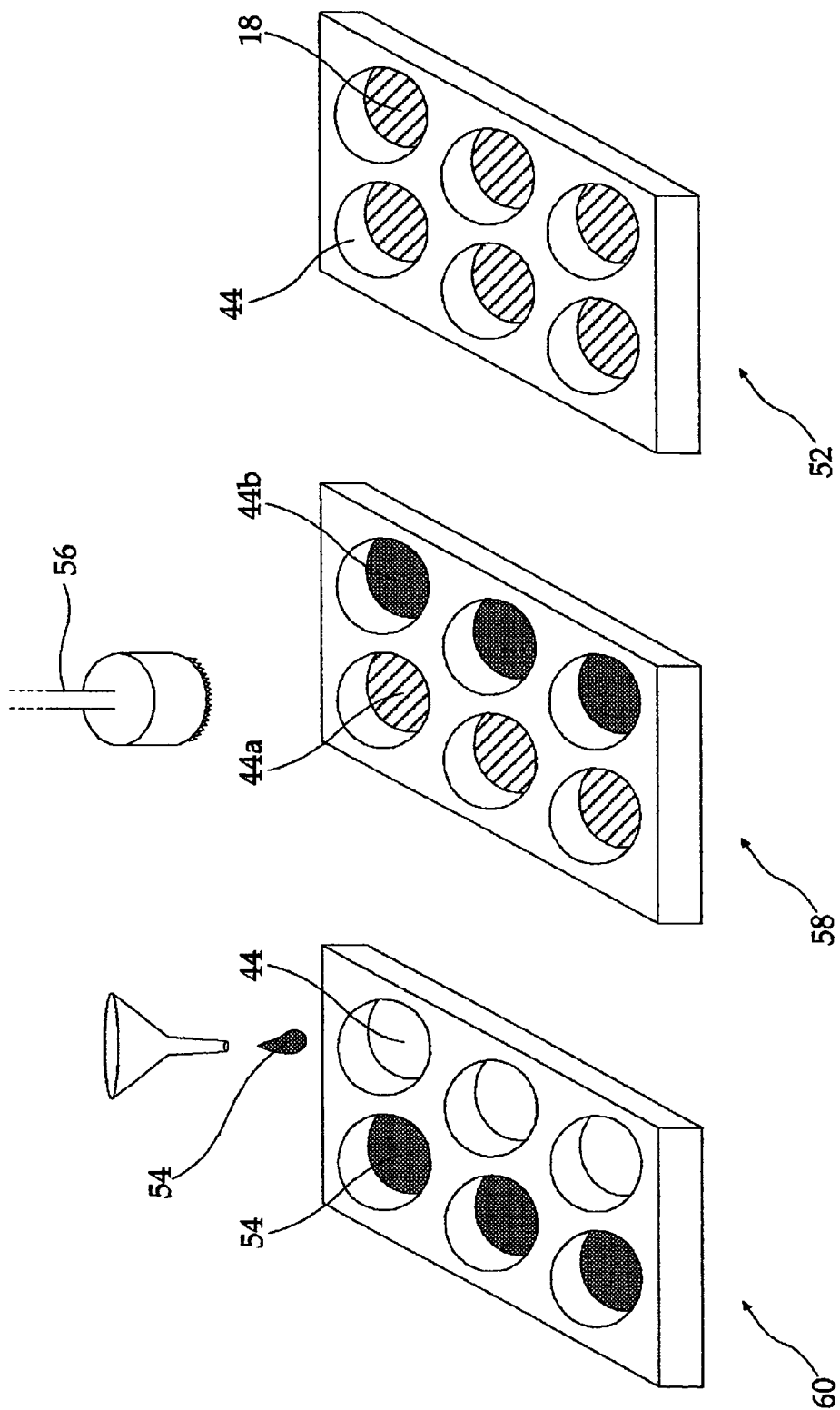
FIGS. 10A-10C are schematic depictions of steps of a method of the present invention for making a multiwell plate of the present invention by contacting a template bearing negatives of a plurality of picowells with a reversibly deformable precursor material inside a well of preexisting multiwell plate.

Steps for producing a six-well plate of the present invention 52 according to a method of the present invention are schematically depicted in FIG. 10. In FIG. 10A, a fluid and therefore reversibly deformable precursor material 54 is placed in a preexisting 6-well plate 60 having six wells 44. Precursor material 54 is a non-cured polydimethylsiloxane precursor mixture (comprising a mixture of a prepolymer and a curing agent). In FIG. 10B, a template 56 substantially a nickel stamp having features that are negatives of features of plate 52 found in wells 44 such as picowells and having a size and shape to precisely fit in a well 44 is contacted with precursor material 54 in each one of wells 44 sequentially so as to form the features of plate 52 in precursor material 54 in each one of wells 44 sequentially. Template 56 is maintained in contact with precursor material 54 in a given well 44 for so long as required for the desired features to be fixed in precursor material 54 by solidification to be polydimethylsiloxane. In FIG. 10B it is seen that at the bottom surfaces of each one of three wells 44a are found a plurality of nanowells 18 while at the bottom of each one of three wells 44b is found non-fixed precursor material 54. Incipient plate 58 undergoes whatever further processing is necessary to ultimately yield plate 52 of the present invention, having pluralities of picowells 18 in each one of six wells 44, FIG. 10C.

In another preferred embodiment, the template includes the negative of the desired features such as picowells but not of the wells. The template is contacted with the precursor material so as to form a substantially planar incipient plate having the features the negatives of which are found on the template. Subsequently, a grid-like component, being substantially the walls of the wells of the multiwell plate of the present invention, is attached using an appropriate method, for example, adhesives (for example, light curable adhesives, such as light curing adhesive 3051 or 3341 manufactured by Henkel Loctite Deutschland GmbH, München, Germany) or surface treatments such as anodic bonding, fusion bonding or plasma treatment such as plasma discharge (exceptionally suitable for attaching polydimethylsiloxane, see Duffy et al., *Anal. Chem.* 1998, 70, 4974-4984).

Figure 11B:
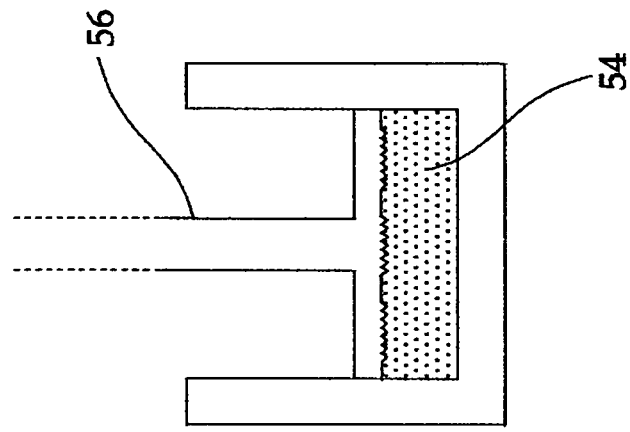
Figure 11A:
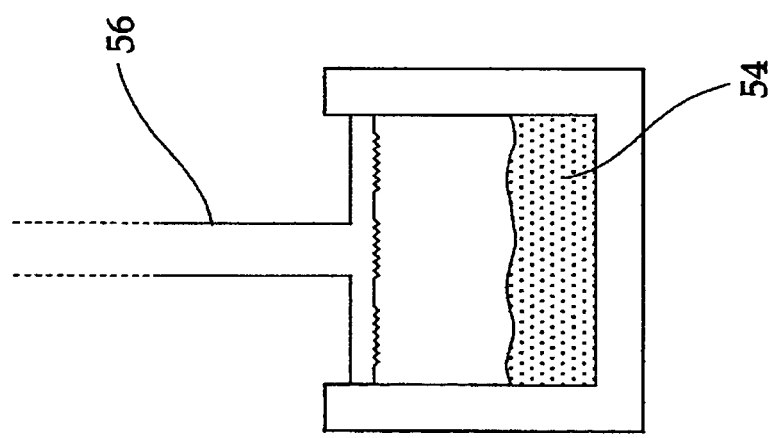
Figure 12A:
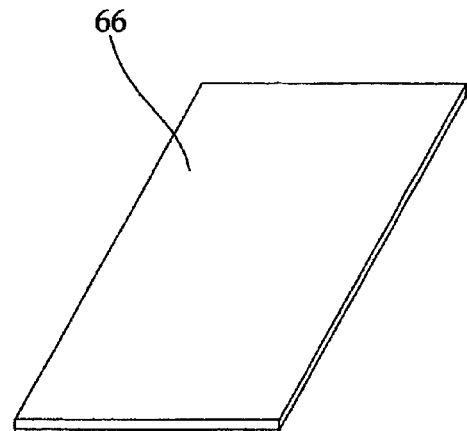
FIGS. 12A-12D are schematic depictions of steps of a method of the present invention for making a multiwell plate of the present invention by producing picowells on a flat precursor plate using photolithography followed by attachment of a separate well-wall component.
Figure 12B:
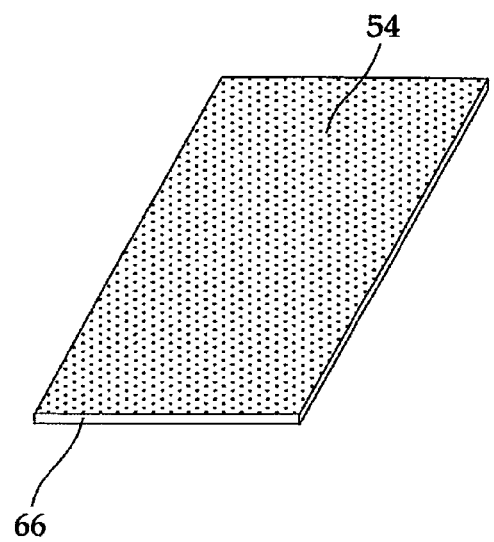
Figure 12C:
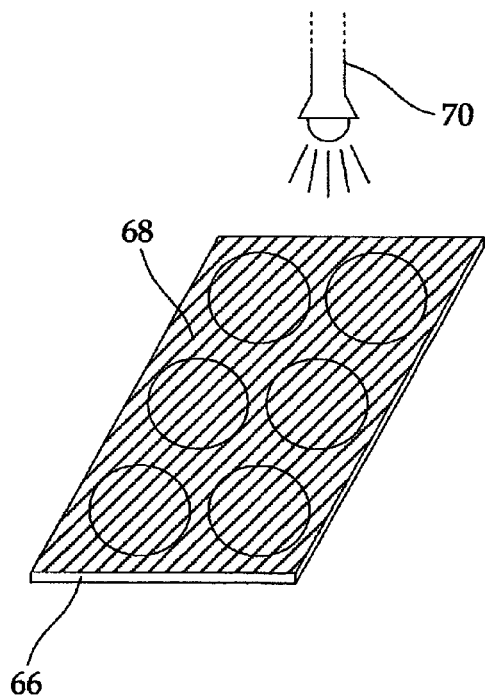
Figure 12D:
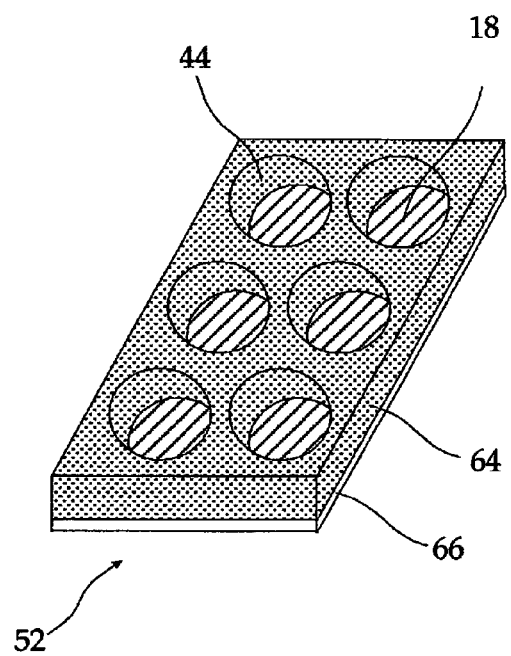

Steps for producing a six-well plate of the present invention 52 according to a method of the present invention are schematically depicted in FIG. 11. In FIG. 11A, a fluid and therefore reversibly deformable precursor material 54 is provided. Precursor material 54 is a non-cured polydimethylsiloxane precursor mixture (comprising a mixture of a prepolymer and a curing agent). In FIG. 11A, a template 56 substantially a nickel stamp having features that are negatives of features of plate 52 such as picowells, but not wells is also provided. In FIG. 11B, template 56 is brought in contact with precursor material 54 so as to form the features of plate 52 in precursor material 54. Template 56 is maintained in contact with precursor material 54 for so long as required for the desired features to be fixed in precursor material 54 by solidification to be polydimethylsiloxane and thus to produce a substantially planar incipient plate 58 having, amongst other features, six pluralities of nanowells 18, FIG. 11C. In FIG. 11D, a grid-like component 64, being substantially the walls of wells 44 of plate 52 of the present invention is provided. Attachment of grid-like component 64 to substantially planar incipient plate 62 using adhesive (e.g., light curing adhesive 3051 manufactured by Henkel Loctite Deutschland GmbH, München, Germany) and whatever further processing is necessary ultimately yields plate 52 of the present invention, having pluralities of picowells 18 in each one of six wells 44, FIG. 11E.

Another preferred method of making a multiwell plate of the present invention includes photolithography of a photoresist material placed on a substrate, a commercially available process (for example, from Micro Resist Technology GmbH, Berlin, Germany) with which one skilled in the art is well-acquainted.

In brief, a high aspect ratio photoresist material (e.g., SU-8 thick photoresist fluid, MicroChem Corporation, Newton Mass., USA) is placed on a precursor plate as a uniformly thick film. A preferred method of achieving a uniformly thin film of a photoresist fluid on a precursor plate is by spin coating, that is, the photoresist fluid is placed on a surface of the precursor plate and the precursor plate is rotated about an axis that is perpendicular to the surface of the substrate on which the photoresist fluid was placed. As a result of the rotation the photoresist fluid forms a uniformly thick film on the precursor plate, typically between about 5 microns and about 20 microns thick. Once a film of uniform thickness of photoresist material is achieved, the photoresist material is illuminated through a mask, the mask being substantially a template or master of the features which are desired to be fixed in the photoresist material including the desired picowells. Developing of the precursor with the selectively fixed film removes the non-fixed areas of the film. In such a way features of a multiwell plate of the present invention are made up of a fixed photoresist layer resting on a precursor plate where the features of the multiwell plate are carved into the photoresist layer and the bottom of the features (such as picowells) is the surface of the precursor plate. Using a photolithography method, picowells and other features are easily produced, including features having a flat-bottom surface.

It is important to note that in addition to picowells, any suitable feature known in the art and discussed herein for multiwell plates of the present invention or for picowell-bearing carriers described in PCT patent application IL 01/00992 or PCT patent application IL 04/00571 can also be added using the photoresist method. Such features include but are not limited to channels, coupling elements, drains, fluid channels, fluid reservoirs, input ports, microreactors, microvalves, passages, output ports, plumbing routes, protruberances, pumps, transport channels, valves, walls and fiducial points.

The material from which the precursor plate is made can be any suitable material. Suitable materials include but are not limited to ceramics, epoxies, glasses, glass-ceramics, metals, plastics, polycarbonates, polydimethylsiloxane, polymers, polyethylenterephtalate glycol, polymethyl methacrylate, polystyrene, polyurethanes, polyvinyl chloride, silicon and silicon oxide.

Steps for producing a six-well plate of the present invention 52 according to a method of the present invention are schematically depicted in FIG. 12. In FIG. 12A, a flat precursor plate 66 is provided. In FIG. 12B, the upper surface of flat precursor plate 66 is coated with a uniformly thin film of a precursor material 54, precursor material 54 being a photoresist fluid (e.g., SU-8 thick photoresist fluid, MicroChem Corporation, Newton Mass., USA). In FIG. 12C, precursor material 54 is illuminated through mask 68 using light source 70 so that features such as picowells are fixed in precursor material 54. After the features are fixed, incipient plate 58 is developed so as to remove non fixed photoresist material and undergoes any further processing necessary including attachment of a grid-like component 64 to ultimately yield plate 52 of the present invention, having pluralities of picowells 18 in each one of six wells 44, FIG. 12D.

In a preferred embodiment, the precursor plate comprises a multiwell plate. In such a case, the photoresist material (preferably a photoresist fluid) is placed into each desired well of the precursor plate and the photoresist material fixed by illumination as described above. Such an embodiment has the advantage that a commercially available multiwell plate of any format (e.g., 6, 24, 96, 384 and 1536 wells) and of virtually any material can be converted into a multiwell plate of the present invention. In such an embodiment a mask can be made and used for fixing picowells and other features in any number of wells including for each well separately or for all wells simultaneously. In this way, a single multiwell plate of the present invention having different features (e.g., different sized picowells) in different wells is easily made.

Steps for producing a six-well plate of the present invention 52 according to a method of the present invention are schematically depicted in FIG. 13. In FIG. 13A, a precursor material 54 is placed in an existing six-well plate 60 having six wells 44. Precursor material 54 is a photoresist fluid (e.g., SU-8 thick photoresist fluid, MicroChem Corporation, Newton Mass., USA). In FIG. 13B, a probe 72 tipped with a mask 74 and provided with a light source 70 having a size and shape to precisely fit in a well 44 is brought in proximity with precursor material 54 in each one of wells 44 sequentially. During the time that mask 74 is in proximity with precursor material 54, light source 70 is activated so that features such as picowells are fixed in precursor material 54 in a respective well 44. In FIG. 13B it is seen that at the bottom surfaces of each one of three wells 44a are found a fixed plurality of nanowells 18 while at the bottom of each one of three wells 44b is found non-fixed precursor material 54. After features are fixed in all desired wells 44, incipient plate 58 is developed so as to remove non fixed photoresist material and undergoes any further processing necessary. Ultimately a plate 52 of the present invention is formed having pluralities of picowells 18 in each one of six wells 44, FIG. 13C.

A preferred method for producing a multiwell plate of the present invention is by producing a substantially planar incipient plate where substantially the entire upper surface is provided with an array of picowells, whether by contact with a temple, by photoresist or other methods. Subsequently a well-wall component or plurality of components is attached to the upper surface. The well-wall component thereby defines the plurality of wells and the upper surface of the precursor plate is substantially the bottom surface of the wells whereupon the picowells are found.

Another preferred method of making a multiwell plate of the present invention comprises attaching one or more picowell-bearing components to a precursor plate using an appropriate method, for example, using an adhesive or a surface treatment such as a plasma treatment, for example as described above. A preferred picowell-bearing component is a carrier comprising a plurality of picowells disposed on a surface. Preferred carriers include those described in PCT patent application IL 01/00992 or PCT patent application IL 04/00571.

In a preferred embodiment, the precursor plate comprises a multiwell plate. In such a case, one or more picowell-bearing components are placed into one or more wells of the precursor plate and attached using a suitable method. Such an embodiment has the advantage that a commercially available multiwell plate of any format (e.g., 6, 24, 96, 384 and 1536 wells) and of virtually any material can be converted into a multiwell plate of the present invention. In such a way many picowell-bearing components of different types are prefabricated, for example by mass production and placed as desired in as many wells of the precursor plate as desired. In this way, a single multiwell plate of the present invention having different features (e.g., different sized picowells) in different wells is easily made.

Figure 2:
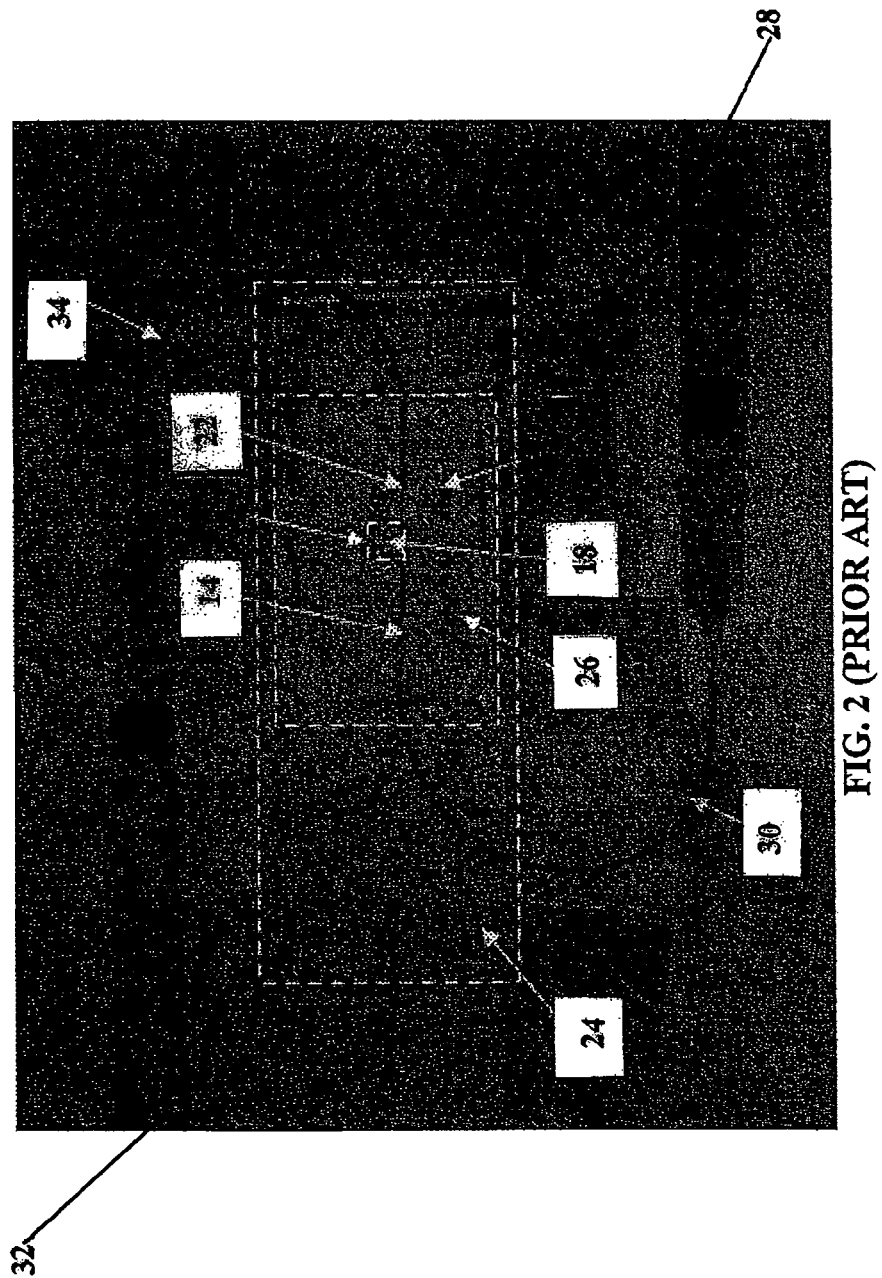
FIG. 2 (prior art) is a reproduction of a photograph of a cell-chip device of PCT patent application IL01/00992.
Figure 3:
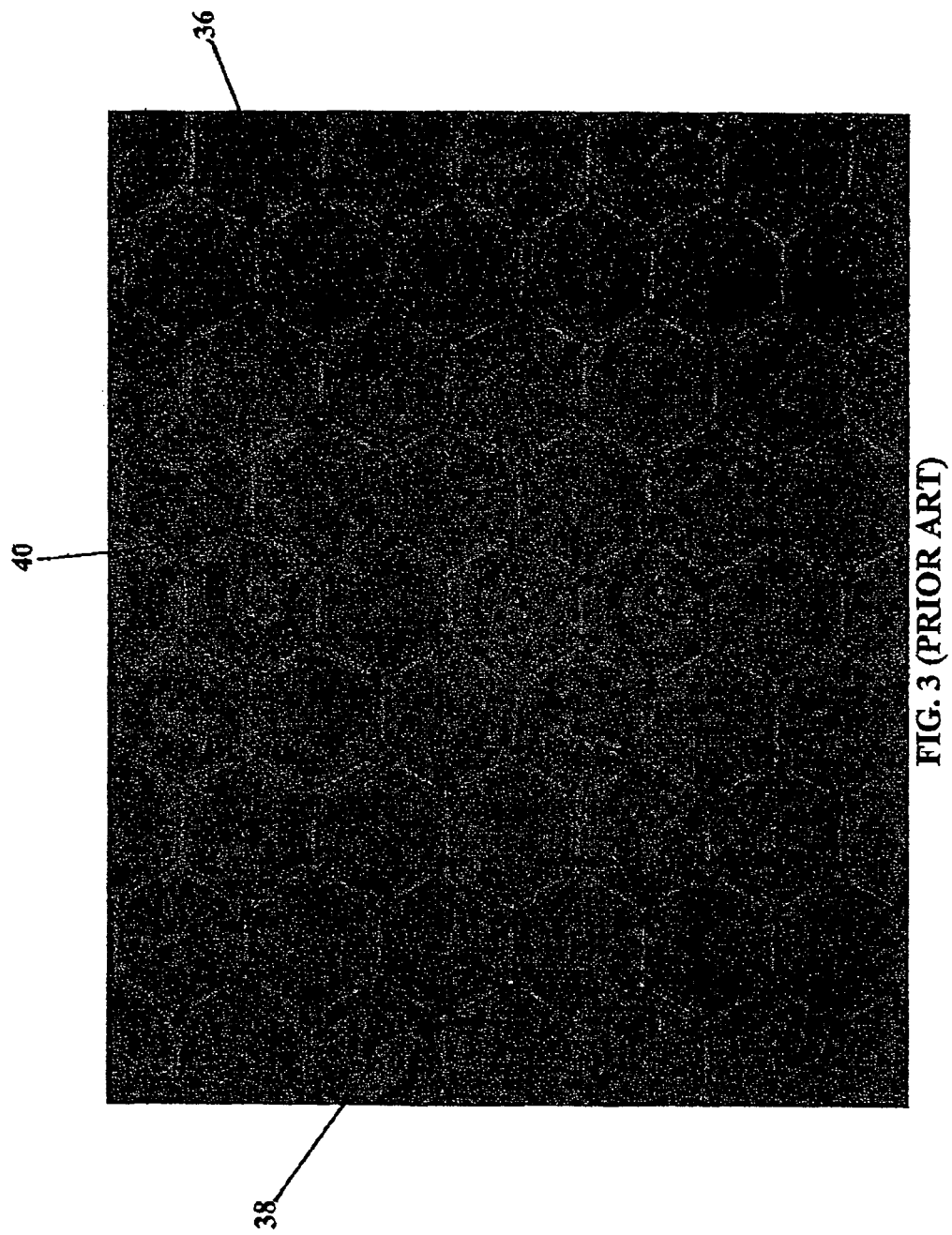
FIG. 3 (prior art) is a reproduction of a photograph of a cell-populated well-array of a carrier of a cell-chip device of PCT patent application IL01/00992.

Steps for producing a six-well plate of the present invention 52 according to a method of the present invention are schematically depicted in FIG. 14. In FIG. 14A, an adhesive 76 (e.g., light curing adhesive 3051 manufactured by Henkel Loctite Deutschland GmbH, München, Germany) is placed in wells 44 of an existing six-well plate 60 having six wells 44. In FIG. 14B, carriers 26, such as carrier 26 depicted in FIG. 2, are placed in each one of six wells 44 and illuminated with light source 70. Adhesive 76 is cured by exposure to light produced by light source 70, attaching each one of six carriers 26 inside a respective well 44, producing a plate 52 of the present invention, having pluralities of picowells 18 in each one of six wells 44, FIG. 14C.

In another preferred embodiment, the precursor plate comprises a substantially planar plate, preferably having the same footprint of a multiwell plate (ca. 8.5 cm by ca. 12.5 cm). The picowell-bearing components are placed in appropriate locations on the precursor plate corresponding to the locations of one or more wells of the ultimately made multiwell plate and attached using a suitable method. Subsequently, a grid-like component, being substantially the walls of the wells of the multiwell plate of the present invention, is attached using an appropriate method, for example, using an adhesive or a surface treatment such as a plasma treatment.

Steps for producing a six-well plate of the present invention 52 according to a method of the present invention are schematically depicted in FIG. 15. In FIG. 15A, a flat precursor plate 66 is provided. In FIG. 15B, carriers 26, such as carrier 26 depicted in FIG. 2, are attached to flat precursor plate 66, for example using an adhesive. Attachment of grid-like component 64 to incipient plate 58 and whatever further processing is necessary ultimately yields plate 52 of the present invention, having pluralities of picowells 18 in each one of six wells 44, FIG. 15C.

It is important to note that in embodiments of the method of making a multiwell plate of the present invention by placing (and optionally attaching) preformed picowell-bearing components to a precursor plate, it is often advantageous that a given picowell-bearing component have dimensions similar or substantially identical to that of a well in which the picowell-bearing component is attached. Such dimensions allow more exact placement of the picowell-bearing component in the well.

Some embodiments of the multiwell plate of the present invention comprise picowells where the inside surface of the picowells (with which held cells potentially make physical contact) is coated with a layer of some desired coating material, for example a coating material that influences the proliferation of living cells as described in PCT patent application IL04/00571.

One skilled in the art is acquainted with many ways and many coating materials with which to coat an inside surfaces of picowells of a multiwell plate of the present invention.

One preferred method of coating inside surfaces of picowells of a multiwell plate of the present invention, applicable to virtually any multiwell plate produced by virtually any method, comprises contacting a precursor fluid with the inside surface of the picowells and subsequently solidifying the precursor fluid, forming the layer of the coating material. Depending on the nature of the precursor fluid, solidifying is performed by any number of methods including but not limited to heating the precursor fluid, cooling the precursor fluid, polymerizing the precursor fluid, cross-linking the precursor fluid, curing the precursor fluid, irradiating the precursor fluid, illuminating the precursor fluid, gelling the precursor fluid, exposing the precursor fluid to a fixative or waiting a period of time.

One preferred method of coating the inside surfaces of picowells of a multiwell plate of the present invention, applicable to virtually any multiwell plate produced by virtually any method, is by vapor deposition. Vapor deposition involves the deposition of materials such as molecules or atoms onto a surface at low pressures and is characterized by the production of evenly thin coatings on a surface, such as the inner surface of a picowell of a multiwell plate of the present invention.

In one embodiment of vapor deposition to the inside surfaces of picowells of a multiwell plate of the present invention, the atoms or molecules that make up the coating material are deposited. In another embodiment of vapor deposition, the atoms or molecules that comprise a precursor of the coating material are deposited on the inside surfaces of the picowells, followed by solidifying the coating precursor material thereby forming the layer of coating material. Solidifying of the coating precursor material to form the layer of coating material is performed by any number of methods including but not limited to heating the coating precursor material, cooling the coating precursor material, polymerizing the coating precursor material, cross-linking the coating precursor material, curing the coating precursor material, irradiating the coating precursor material, illuminating the coating precursor material, gelling the coating precursor material, exposing the coating precursor material to a fixative and waiting a period of time.

A preferred coating material for coating the inside surfaces of picowells of a multiwell plate of the present invention is made of polymerized para-xylylene molecules (or derivatives thereof, specifically where one or more hydrogens, especially aromatic hydrogens of either or both aromatic rings are substituted) deposited by vapor deposition, a coating commercially known as Parylene® (available for example from V&P Scientific, Inc., San Diego, Calif., USA). Parylene® is preferred not only for cell proliferation influencing properties but also for the fact that Parylene® coatings are bacteria resistant, fungus resistant, transparent, have a low permeability, acid and base resistant, uniform, thin (typically 0.1-1 micron) and without voids even when a coated surface includes configurations with sharp edges, points, flat surfaces, crevices or exposed internal surfaces.

The teachings of the present invention provide the possibility of providing a device useful in the field of cellular biology. A device of the present invention comprises an array of living cells held in a non-fluid matrix, the matrix configured to maintain cell viability. Generally, the matrix of a device of the present is configured to maintain cell viability. To maintain cell viability, a matrix is generally non-cytotoxic and allows transport of molecules necessary for cell survival and metabolism, such as nutrients, gases, ions and waste to and from a living cell held therein. A suitable matrix is a matrix comprising a gel, preferably a hydrogel. Preferably, the living cells are physically held in pockets in the matrix, especially free-floating in a physiological fluid in the pockets. To reduce any influence on the reactions of the cells, there is preferably substantially no bond (e.g., chemical bond) between the living cells and the matrix.

Figure 16:
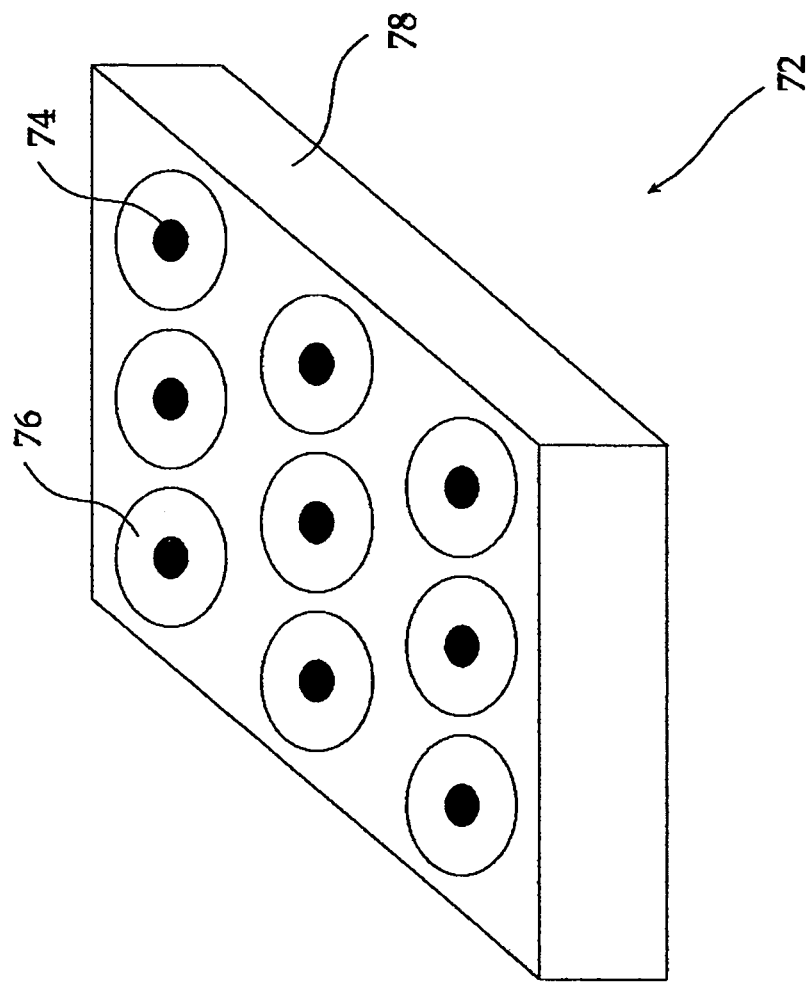
FIG. 16 is a schematic depiction of a device of the present invention being substantially a 3 by 3 array of living cells held in a non-fluid matrix.

In FIG. 16 is depicted a device of the present invention 72, being substantially nine living cells 74 floating inside pockets 76 inside a hydrogel matrix 78.

In a preferred embodiment, to simplify use of the device, the array is substantially planar having an upper surface and a lower surface. In a preferred embodiment of the present invention, by substantially planar is meant that substantially all living cells of the array are arranged in a single unique plane. In another preferred embodiment of the present invention, by substantially planar is meant that substantially all the living cells are arranged in two or more planes.

To ease observation of the cells or detection of signals associated with the cells, in a preferred embodiment of the device of the present invention, one or both of the two surfaces of the device is transparent to at least one wavelength of light, including a wavelength of light of the ultraviolet spectrum, the visible spectrum or the infrared spectrum. Further, to ease observation of the cells or detection of signals associated with the cells, in a preferred embodiment of the present invention, the matrix comprises a material having an index of refraction substantially similar to that of water. By substantially similar is meant an index of refraction of less than about 1.4, less than about 1.38, less than about 1.36, less than about 1.35 or even less than about 1.34.

In a preferred embodiment of the present invention, the matrix is configured to substantially delay proliferation of living cells held therein. Configuration of a matrix so as to substantially delay proliferation of the living cells is taught in PCT IL04/00571. A preferred method of configuring a matrix to substantially delay proliferation is to make at least part of the matrix from a material that has proliferation delaying properties. A preferred such material is a gel, especially a hydrogel.

In a preferred embodiment of the present invention, the matrix comprises an active entity, especially an indicator. By indicator is meant an active entity configured to indicate a cell response to a stimulus, for example a molecule that is chromatogenic or fluorogenic upon exposure to some compound released by a given living cell held in the device upon exposure to some stimulus.

The unique characteristics of a device of the present invention are better understood by comparing the device to living tissue on the one hand and prior art arrays of living cells on the other hand.

As is known to one skilled in the art, living tissue can be considered to comprise living cells held within a matrix. Further living tissue can be maintained living for an extended period of time. It is therefore known in the art to use devices incorporating living tissues in a device for assaying cell response to stimuli. However, in living tissue the cells are not in an array; the cells are not distinct from each other making identification of individual cell response difficult if not impossible especially under high throughput conditions; cells are not individually addressable so a cell of interest must be maintained under continuous observation; cells are not coplanar making visual study time-consuming due to the need for refocusing; cells are in contact with each other so that one cell may influence other neighboring cells; living tissue cannot be engineered as desired to hold specific different cells in a desired spatial relationship to each other; cells in living tissue proliferate, meaning that the properties of a device including living tissue are not well-defined and change over time. Depending on the embodiment, a device of the present invention provides overcomes some or all of these disadvantages.

As discussed in the introduction, prior art arrays of cells all have a number of critical disadvantages. In some prior art arrays, the cells are bound to some object, whether by native adhesion or by some non-native chemical bond or attraction. Binding a cell necessarily compromises the response of cell to stimuli. In other prior art cell arrays, there is nothing keeping cells from moving from a designated location so that there is no way to ensure that array integrity is maintained. This is exceptionally significant when cell apoptosis or other death processes occurs or when the cell array is moved. The device of the present invention provides, in contrast to prior art devices, a cell array that is robust during any cell process including cell death and during movement of the device itself.

The device of the present invention is exceptionally useful for implementing certain manipulations of living cells. For example, a device of the present invention, being substantially an ordered array of selected cells, is made in a first location such as a laboratory. The device is transported to a remote location, for example to a second laboratory, in a space vehicle or to the location of a suspected environmental disaster. A sample is contacted with the array of living cells of the device (for example, by diffusion through the matrix). The reaction of the cells is observed indicating something about the nature of the sample or of the living cells. As is clear to one skilled in the art, the device of the present invention is useful for transporting ordered cell arrays. As is clear to one skilled in the art, the device of the present invention is also useful as an indicator or assay device.

The method of the present invention comprises providing an ordered array of living cells immobilized in a matrix, the matrix configured to maintain cell viability; (b) contacting the living cells with a stimulus; and (c) detecting the response of the living cells to the stimulus.

To simplify detection or observation of the response, in a preferred embodiment of the present invention, the matrix comprises an active entity, especially an indicator, as described above. In another preferred embodiment (alone or together with an active entity of the matrix), the matrix is contacted with an active entity, preferably an active entity in solution. Generally, subsequent to contacting an active entity with the matrix, it is necessary to wait a period of time in order to allow the active entity to reach the proximity of the cells, for example by diffusion.

Although there are many methods for detecting the response of the living cells to a stimulus, the preferred method involves the detection of light. By detection of light is meant detection of emitted light (for example, light emitted by an indicator or light emitted by a given cell). By detection of light is also meant detection of light that has interacted with a given cell, the vicinity of a given cell, or an indicator in the vicinity of a given cell where the light is indicative of the cell response. Clearly such detecting includes detection of fluorescence, differential polarization and optical inspection of a cell.

A device of the present invention is a preferred device for implementing the method of the present invention. That said, the present invention also provides a general method for producing an ordered array of living cells useful, for example, in implementing the method of the present invention using a multiwell plate of the present invention. The method of producing an ordered array of living cells, comprises: (a) providing a multiwell plate of the present invention, (b) placing a suspension of a plurality of living cells in a gellable fluid in at least one well provided with picowells; (c) causing the living cells to settle into the picowells so as to be held in respective picowells; and (d) gelling the gellable fluid so as to make a gel cover, trapping the living cells between the picowells and the gel cover. In a preferred embodiment, the picowells are made of a material comprising a gel, preferably a hydrogel.

Generally, causing the cells to settle into the wells includes applying a force to the cells, typical forces including gravitation, centrifugal forces, forces resulting from the impact of photons on the cells (e.g., laser tweezers, application of a non-focussed laser (see, for example, P.A.L.M. Microlaser Technologies AG, Bernried, Germany)), or forces resulting from a pressure wave (such as produced by an ultrasonic transponder). Most preferred is the application of centrifugal force, vide infra.

As stated above, once the cells have settled in a respective picowell, it is preferred to gel the gellable fluid so as to form a cover on the picowells. As a result, the cells are held snugly, without excessive physical stress, between the inside of a respective picowell and the surrounding gel cover. An appropriate method of gelling a gellable fluid is dependent on the nature of the gellable fluid and includes methods such as heating the gellable fluid, cooling the gellable fluid, irradiating the gellable fluid, illuminating the gellable fluid, contacting the gellable fluid with a gelling reagent and waiting a period of time for the gellable fluid to gel.

It is generally preferred to use a gellable fluid that forms a hydrogel upon gelling. Exceptionally suitable gellable fluids are fluids that comprise a material selected from the group consisting of agars, agaroses, gelatins, low melting temperature agaroses, alginates, room-temperature $Ca^{2+}$-inducable alginates and polysaccharides.

It is preferred that a gellable fluid that gels under conditions that are conducive for cell survival be used for implementing the teachings of the present invention. One preferred gellable fluid is an alginate solution. Alginates are biologically compatible polysaccharide proteins that are fluid at low calcium ion concentrations (e.g., $[Ca^{2+}]<1$ μM) but gel upon exposure to higher concentrations of calcium ions (e.g., $[Ca^{2+}]=20$ mM). An exceptionally suitable alginate for implementing the teachings of the present invention is sodium alginate and may be purchased, for example, from Pronova Biopolymers (Drammen, Norway) as Protanal LF120 1% in water or Protanal LF200 1% in water.

Another preferred gellable solution is a solution of low melting temperature agarose. Low melting temperature agaroses are biologically compatible gels that before gelling are fluid at temperatures that do not harm living cells (e.g., 20° C.), gel at low temperatures that do not harm living cells (e.g., 4° C.) and remain stable until well-above temperatures used for studying living cells (40° C.). An exceptionally suitable agarose for implementing the teachings of the present invention that may be purchased, for example, from Cambrex Bio Science Rockland Inc. (Rockland, Me., USA) is HGS-LMP Agarose (catalogue nr. 50221).

It is important to note that for maximal utility of a produced device, it is desirable to ensure that substantially each pocket holds no more than one living cell or no more than a predetermined number of cells. This is most easily achieved by ensuring that the picowells of the picowell array are juxtaposed and that a given picowell is of a size to accommodate no more than one living cell (or the predetermined number of cells). Generally when a suspension of cells with a number of cells greater than the number of picowells is placed in proximity of juxtaposed picowells and the cells allowed to settle, all picowells will be filled but there will be excess cells "stacked" on top of cells held in picowells. A preferred method for preventing such "stacking" is that the suspension brought in proximity of the picowells has approximately a predetermined number of cells. It has been found that when the number of cells in the suspension is approximately equal to the number of picowells (or the product of the number of picowells and the number of cells desired to be held in each picowell), there is substantially the desired number of cells per picowell, with only minimal stacking of cells on top of already fully occupied picowells.

In a preferred embodiment of the method of the present invention, the gellable fluid includes an active entity, especially an indicator, as described above. In such a way, the active entity becomes an integral part of the matrix of a device produced according to the method of the present invention.

In some embodiments of the method of the present invention, some or all of the wells of a multiwell plate are provided with picowells. In some embodiments, all of the picowells of the multiwell plate are substantially the same. In some embodiments, all of the picowells in one well are substantially the same, but are different from picowells in other wells. In some embodiments, in a given well, there are found two different types of picowells. By different is meant, for example, have a different size or comprise different active ingredients.

Figure 17:
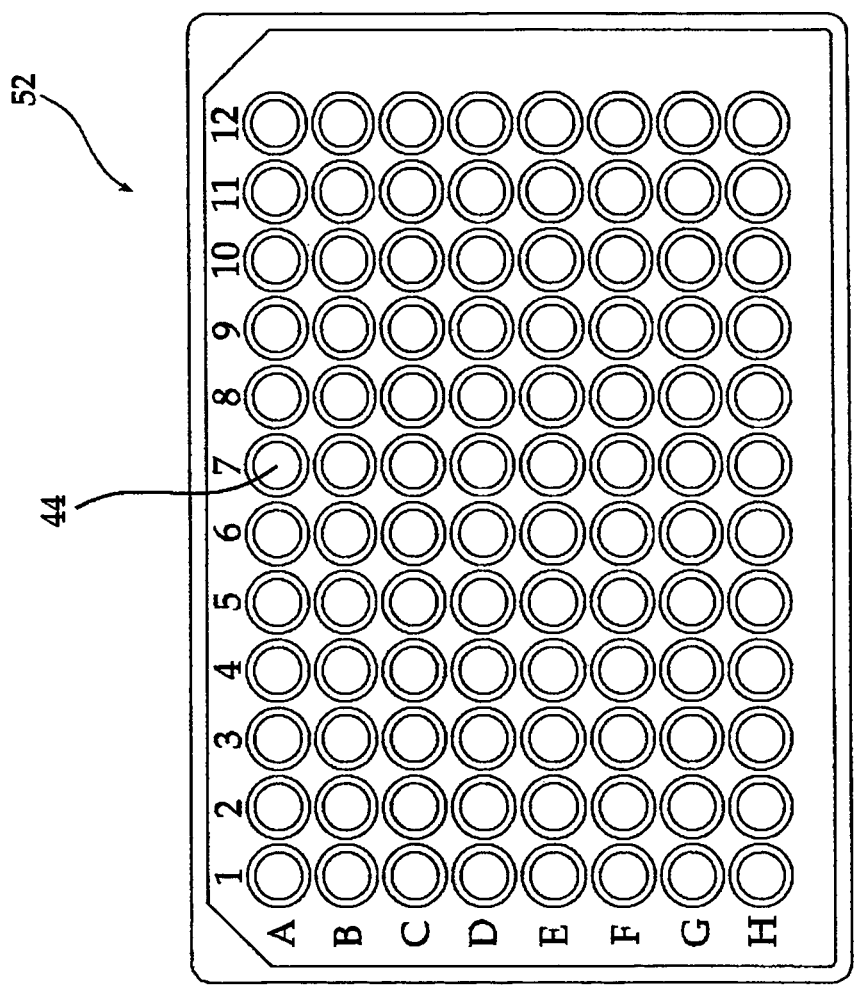
FIG. 17 is a schematic depiction of a 96-well plate of the present invention comprising arrays of living cells in a non-fluid matrix.

In a specific example, a 96-well glass plate 52 of the present invention is provided, FIG. 17. In plate 52, all wells 44 are provided with a plurality of integrally formed hexagonally-packed knife-edged hexagonal picowells. The picowells in each one of wells 44 of rows A, B, C and D have a diameter of 10 micron while the plurality of picowells 18 in each one of wells 44 of rows in rows E, F, G and H have a diameter of 20 micron.

Using an automatic liquid dispensing robot (Automated Microplate Pipetting Systems—Precision™ XS Microplate Sample Processor, Bio-Tek Instruments, Vinooski, Vt., USA) different suspensions of living cells in liquid solutions of a gellable solution, comprising a low melting temperature agarose (e.g., HGS-LMP Agarose of Cambrex Bio Science Rockland Inc., Rockland, Me., USA) are added to the wells of each row. The cells suspended in the solution dispensed in rows A, B, C and D are peripheral lymphocytes having a diameter of about 5 to 7 microns. The cells suspended in the solution dispensed in rows E, F, G and H are Jurkat T cell line cells having a diameter of about 15-20. The number of cells dispensed in each well 44 is about 95% of the number of picowells in that well. In addition, the solutions dispensed into a given well 44 also include active reagents:

a. in the solutions dispensed in rows A, B, E and F a first indicator for measuring mitochondrial membrane potential is dispensed (100 nM tetramethyl rhodamine methyl ester);

b. in the solutions dispense in rows C, D, G and H a second indicator for measuring intracellular levels of reactive oxygen species is dispensed (10 μM dichlorodihydro fluorescein diacetate);

Once all cell suspensions are dispensed, 96-well plate 52 is transferred to a centrifuge provided with a cooling unit and centrifuged so as to cause dispensed cells to settle into picowells. After sufficient time for cell settling, centrifugation is stopped and the cooling unit is activated so as to bring the temperature of the gel to about 4° C. and thus initiate gelling. When sufficient time has passed for complete gelling of the gellable fluid, the multiwell plate is used for examining metabolism during cell death. To rows B, D, F and H a third active agent (50 μM solution of hydrogen peroxide as apoptosis inducer) is added to each one of wells 44 of rows B, D, F and H. During the time it takes for the third active agent to diffuse through the gel cover, plate 52 is transferred to an observation unit configured to detect the intensity of color developed in each picowell. Comparison of the development of color in wells of row B (with A as control) shows the development of mitochondrial membrane potential as a result of apoptosis of peripheral lymphocytes. Comparison of the development of color in wells of row C (with D as control) shows the development of intracellular levels of reactive oxygen species as a result of apoptosis of peripheral lymphocytes. Comparison of the development of color in wells of row F (with E as control) shows the development of mitochondrial membrane potential as a result of apoptosis of Jurkat T cells. Comparison of the development of color in wells of row H (with G as control) shows the development of intracellular levels of reactive oxygen species as a result of apoptosis of Jurkat T cells.

Since each of the cells is held in a respective picowell, no cell is lost during the apoptosis process. Since the cells are held in a substantially planar array of cells, the exact number of cells and distribution of reactions is accurately monitored.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. Although the invention has been described in conjunction with specific embodiments thereof, it is evident that many alternatives, modifications and variations will be apparent to those skilled in the art. Accordingly, the present invention is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A multiwell plate comprising a unitary structure including a plurality of wells wherein the bottom surface of at least one well of said plurality of wells includes a plurality of picowells, wherein said picowells are unitary structures each comprised of a bottom and a side wall integrally formed with said bottom, and the bottoms and side walls of said picowells include a coating of a material that inhibits or delays adherence of cells in said picowells.

2. The plate of claim 1, having a footprint of a standard multiwell plate.

3. The plate of claim 1, wherein said plurality of wells comprises 6n wells arranged in a 2n×3n array, where n is an integer greater than 0.

4. The plate of claim 3, wherein said plurality of wells is selected from the group consisting of 6, 24, 96, 384 and 1536 wells.

5. The plate of claim 1, wherein picowells of said plurality of picowells are juxtaposed.

6. The plate of claim 5, wherein the interwell area between two said picowells is less than about 0.35 times the sum of the areas of said two picowells.

7. The plate of claim 5, wherein a rim of a said picowell is substantially knife-edged.

8. The plate of claim 1, wherein said plurality of picowells comprises picowells having dimensions of less than about 200 microns.

9. The plate of claim 1, wherein all picowells of the plate are substantially identical in size.

10. The plate of claim 1, wherein a first well includes a first plurality of picowells and a second well includes a second plurality of picowells, wherein said first plurality of picowells and said second plurality of picowells are substantially different.

11. The plate of claim 1, further including at least one distinct picowell-bearing component, said picowell-bearing component being attached to said bottom surface of said one well as part of said unitary structure.

12. The plate of claim 11, wherein said picowell-bearing component comprises a gel.

13. The device of claim 12, wherein the water content of said gel is greater than about 80% by weight.

14. The device of claim 12, wherein said gel comprises an active entity.

15. The plate of claim 1, wherein the bottoms of said picowells have an index of refraction similar to that of water.

16. The plate of claim 15, wherein said index of refraction is less than about 1.4.

17. The plate of claim 1, further comprising a gel cover covering said plurality of picowells.

18. The plate of claim 1, wherein said plurality of picowells covers substantially the entire said bottom surface of said well.

19. The device of claim 1, wherein a cross-section of said picowells is hexagonal, rectangular, triangular, or circular.

20. The device of claim 1, wherein the volume of said picowells is in the range of less than about $10^{-12}$ to about $10^{-15}$ liters.

21. The device of claim 1, wherein the volume of said picowells is in the range of about $10^{-11}$ to about $10^{-12}$ liters.

22. A multiwell plate comprising a unitary structure including a plurality of wells wherein at the bottom surface of at least one well of said plurality of wells is includes a plurality of picowells, wherein said picowells are unitary structures each comprised of a bottom and a side wall integrally formed with said bottom, and wherein the bottoms and side walls of said picowells include a coating of a material that affects proliferation of cells in said picowells.

23. The device of claim 22, wherein the bottom surfaces of said plurality of wells is formed substantially of a material having an index of refraction between that of water and about 1.4.

24. The device of claim 22, further comprising a gel covering said plurality of picowells.

25. The device of claim 22, wherein the inter picowell area between two picowells is less than or equal to about 0.35 times the sum of the areas of the two picowells.

26. The device of claim 22, wherein rims of a said picowells are substantially knife-edged.

27. The device of claim 22, wherein the dimensions of said picowells are less than about 200 microns.

28. The device of claim 22, wherein the volume of said picowells is in the range of less than about $10^{-12}$ to less than about $10^{-15}$ liters.

29. A device according to claim 22, wherein the multi-well plate has a footprint of a standard multi-well plate.

30. A device according to claim 22, wherein picowells of said plurality of picowells are juxtaposed.

31. A device according to claim 22, wherein said plurality of picowells comprise enclosures of dimensions such that substantially an entire cell of a certain size can be held within a said enclosure, each said enclosure having an opening, said opening defined by a first cross section of a size allowing passage of a cell of a certain size.

32. A device according to claim 22, further including at least one distinct picowell-bearing component, said picowell-bearing component being attached to said bottom surface of said one well as part of said unitary; structure.

33. The plate of claim 32, wherein said plurality of picowells comprise enclosures of dimensions such that substantially an entire cell of a certain size can be held within a said enclosure, each said enclosure having an opening, said opening defined by a first cross section of a size allowing passage of a cell of a certain size.

34. The device of claim 32, wherein said picowell bearing component is formed of a gel.

35. The device of claim 34, wherein the gel contains water, the water content of said gel being greater than about 80% by weight of said gel.

36. The device of claim 34, wherein said gel includes an active entity.

37. A device according to claim 32, wherein said wells are configured to hold a single cell of a certain type or a predetermined maximum number of cells of said certain type.

38. A device according to claim 22, wherein a cross-section of said picowells is hexagonal, rectangular, triangular, or circular.

39. A device according to claim 38, wherein the rims of said picowells are substantially knife-edged.

40. A device according to claim 22, wherein the volume of said picowells is in the range of about $10^{-11}$ to about $10^{-12}$ liters.

41. A device according to claim 22, wherein said picowells are configured to hold a single cell of a certain type or a predetermined maximum number of cells of said certain type.

42. A device according to claim 22, wherein said coating is of a material that inhibits or delays proliferation of cells in said picowells.

43. A method of making a multiwell plate comprised of an integral structure formed of a plurality of wells and a plurality of picowells on the bottom of at least one of said wells, the method comprising:
   (a) placing a precursor material on a substrate;
   (b) contacting said precursor material with a template including a negative of one or more features of said plate including said picowells;
   (b) fixing said one or more features in said precursor material so as to fashion an incipient plate; and
   (c) processing said incipient plate so as to fashion said unitary structure of said plurality of wells and said plurality of picowells with said picowells attached to a bottom surface of at least one of said wells as part of said unitary structure; and
   (d) coating the bottoms and side walls of said picowells with a material that affects proliferation of cells in said picowells.

44. The method of claim 43, further comprising:
   (e) prior to contacting the precursor material with the template, placing said precursor material in a well of a multiwell plate.

45. The method of claim 43, further comprising:
   (f) subsequent to fixing said one or more features in said precursor material, attaching walls of said plurality of wells to said incipient plate to form part of said integral structure.

46. The method of claim 43, wherein said precursor material comprises an irreversibly deformable precursor material and said fixing said features comprises separating said template from said precursor material.

47. The method of claim 43, wherein said precursor material comprises a reversibly deformable precursor material and the features are fixed while said template is in contact with the precursor material.

48. The method of claim 43, wherein said template contains a negative of said plurality of picowells.

49. The method of claim 43, wherein said precursor material is plastically deformable and said features are fixed by separating said template from said precursor material.

50. The method of claim 43, wherein said precursor material is an elastic material.

51. The method of claim 43, wherein said precursor material is a gel, and said features are fixed by gelling said gellable fluid.

52. The method of claim 51, wherein the water content of said gel is greater than about 80% by weight.

53. The method of claim 51, wherein said gel comprises an active entity.

54. The method of claim 43, wherein said precursor material is irreversibly deformable and said features are fixed by separating said template from said precursor material.

55. The method of claim 43, wherein said precursor is a photoresist material; and said picowells are fixed in said photoresist material.

56. The method of claim 43 wherein the coating material delays or inhibits adherence of cells in said wells.

57. The method of claim 43 wherein the coating material delays or inhibits proliferation of cells in said picowells.

58. The method of claim 43, further comprising:
   (g) providing a gel cover configured to cover said plurality of picowells.

* * * * *